United States Patent
Appleby et al.

(10) Patent No.: US 7,410,606 B2
(45) Date of Patent: Aug. 12, 2008

(54) METHODS FOR MANUFACTURING THREE-DIMENSIONAL DEVICES AND DEVICES CREATED THEREBY

(76) Inventors: Michael P. Appleby, 2268 Stargate La., Charlottesville, VA (US) 22911; Iain Fraser, 337 Deer Dr., Ruckersville, VA (US) 22968; James E. Atkinson, 3546 Stoney Point Rd., Charlottesville, VA (US) 22911

( * ) Notice: Subject to any disclaimer, the term of this patent is extended or adjusted under 35 U.S.C. 154(b) by 664 days.

(21) Appl. No.: 10/479,335

(22) PCT Filed: Jun. 5, 2002

(86) PCT No.: PCT/US02/17936

§ 371 (c)(1),
(2), (4) Date: Dec. 1, 2003

(87) PCT Pub. No.: WO02/098624

PCT Pub. Date: Dec. 12, 2002

(65) Prior Publication Data

US 2004/0156478 A1    Aug. 12, 2004

Related U.S. Application Data

(60) Provisional application No. 60/295,564, filed on Jun. 5, 2001, provisional application No. 60/339,773, filed on Dec. 17, 2001.

(51) Int. Cl.
 *B29C 33/40* (2006.01)
(52) U.S. Cl. ............... 264/219; 249/117; 249/134; 249/135; 264/318

(58) Field of Classification Search ........... 264/219, 264/318; 249/117, 134, 135
See application file for complete search history.

(56) References Cited

U.S. PATENT DOCUMENTS

| | | | |
|---|---|---|---|
| 408,677 | A | 8/1889 | Tabor |
| 460,377 | A | 9/1891 | Lake |
| 1,164,987 | A | 12/1915 | Bucky |
| 3,379,812 | A | 4/1968 | Yakovou |
| 3,676,541 | A | 7/1972 | Nishi |
| 3,829,536 | A | 8/1974 | Alvarez |

(Continued)

FOREIGN PATENT DOCUMENTS

JP    02099260 A2    4/1990

OTHER PUBLICATIONS

Desai, Upendra, "New Fabrication Methodology for Fine Feature-High Aspect Ratio Structures Made from High Z Materials", Part of the SPIE Conference on Micromachining and Microfabrication Process Technology, Sep. 22, 1999, 7 pages, SPIE vol. 3874, US.

(Continued)

*Primary Examiner*—Leo B Tentoni
(74) *Attorney, Agent, or Firm*—Michael Haynes PLC; Michael N. Haynes; Dale R. Jensen

(57) ABSTRACT

A process of making a casting includes the steps of designing a mold (1010), fabricating the layers (or laminations) of the mold (1020), stacking and assembling the laminations into a mold (1030), producing a casting (1060) and demolding the casting (1070). If necessary, a derived mold can be made (1040, 1050) prior to producing the casing (1060).

63 Claims, 35 Drawing Sheets

U.S. PATENT DOCUMENTS

| | | | |
|---|---|---|---|
| 3,964,534 A | 6/1976 | Rabinowitz | |
| 4,288,697 A | 9/1981 | Albert | |
| 4,355,400 A | 10/1982 | Doemer et al. | |
| 4,356,400 A | 10/1982 | Polizzi | |
| 4,465,540 A | 8/1984 | Albert | |
| 4,748,328 A | 5/1988 | Chang et al. | |
| 4,801,379 A | 1/1989 | Ehrsam et al. | |
| 4,812,236 A | 3/1989 | Ehrsam | |
| 4,825,646 A | 5/1989 | Challoner et al. | |
| 4,856,043 A | 8/1989 | Zola | |
| 4,915,757 A | 4/1990 | Rando | |
| 4,951,305 A | 8/1990 | Moore et al. | |
| 5,002,889 A | 3/1991 | Klein | |
| 5,017,317 A | 5/1991 | Marcus | |
| 5,043,043 A | 8/1991 | Howe et al. | |
| 5,088,047 A | 2/1992 | Bynum | |
| 5,126,529 A | 6/1992 | Weiss | |
| 5,127,037 A | 6/1992 | Bynum | |
| 5,147,761 A | 9/1992 | Wessells et al. | |
| 5,150,183 A | 9/1992 | Mikosch | |
| 5,183,598 A | 2/1993 | Hellé | |
| 5,190,637 A | 3/1993 | Guckel | |
| 5,192,559 A | 3/1993 | Hull | |
| 5,203,944 A | 4/1993 | Prinz | |
| 5,206,983 A | 5/1993 | Guckel et al. | |
| 5,207,371 A | 5/1993 | Prinz | |
| 5,208,431 A | 5/1993 | Uchiyama | |
| 5,216,616 A | 6/1993 | Masters | |
| 5,252,881 A | 10/1993 | Muller et al. | |
| 5,286,573 A | 2/1994 | Prinz | |
| 5,301,863 A | 4/1994 | Prinz | |
| 5,306,447 A | 4/1994 | Marcus | |
| 5,348,693 A | 9/1994 | Taylor | |
| 5,378,583 A | 1/1995 | Guckel | |
| 5,398,193 A | 3/1995 | deAngelis | |
| 5,447,068 A | 9/1995 | Tang | |
| 5,450,183 A | 9/1995 | O'Leary | |
| 5,450,751 A | 9/1995 | Putty et al. | |
| 5,459,320 A | 10/1995 | Danet et al. | |
| 5,483,387 A | 1/1996 | Bauhahn et al. | |
| 5,514,232 A | 5/1996 | Burns | |
| 5,551,904 A | 9/1996 | Hedges et al. | |
| 5,555,481 A | 9/1996 | Rock | |
| 5,559,708 A | 9/1996 | Turnbull | |
| 5,576,147 A | 11/1996 | Guckel et al. | |
| 5,596,504 A | 1/1997 | Tata | |
| 5,606,589 A | 2/1997 | Pellegrino | |
| 5,620,854 A | 4/1997 | Holzrichter et al. | |
| 5,637,169 A | 6/1997 | Hull | |
| 5,638,212 A | 6/1997 | Meyers et al. | |
| 5,644,177 A | 7/1997 | Guckel et al. | |
| 5,681,661 A | 10/1997 | Kelly | |
| 5,692,507 A | 12/1997 | Seppi et al. | |
| 5,702,384 A | 12/1997 | Umeyama et al. | |
| 5,718,618 A | 2/1998 | Guckel et al. | |
| 5,721,687 A | 2/1998 | Lamartine et al. | |
| 5,729,585 A | 3/1998 | Pellegrino | |
| 5,763,318 A | 6/1998 | Bertin et al. | |
| 5,773,116 A | 6/1998 | Lamartine et al. | |
| 5,778,468 A | 7/1998 | Saarela et al. | |
| 5,786,597 A | 7/1998 | Lingren et al. | |
| 5,795,748 A | 8/1998 | Cottingham | |
| 5,814,235 A | 9/1998 | Pellegrino | |
| 5,814,807 A | 9/1998 | Musha et al. | |
| 5,836,150 A | 11/1998 | Garcia | |
| 5,849,229 A | 12/1998 | Holtzberg | |
| 5,851,897 A | 12/1998 | Wu | |
| 5,855,718 A | 1/1999 | Nguyen | |
| 5,879,489 A | 3/1999 | Burns | |
| 5,902,538 A | 5/1999 | Kruger | |
| 5,924,277 A | 7/1999 | Beattie et al. | |
| 5,925,308 A | 7/1999 | Fewkes et al. | |
| 5,929,446 A | 7/1999 | Plummer et al. | |
| 5,932,940 A | 8/1999 | Epstein et al. | |
| 5,949,850 A | 9/1999 | Tang | |
| 5,955,801 A | 9/1999 | Romero et al. | |
| 5,955,818 A | 9/1999 | Bertin et al. | |
| 5,962,949 A | 10/1999 | Dhuler et al. | |
| 5,963,788 A | 10/1999 | Barron et al. | |
| 5,985,204 A | 11/1999 | Otsuka | |
| 5,994,801 A | 11/1999 | Garcia | |
| 5,994,816 A | 11/1999 | Dhuler et al. | |
| 5,998,260 A | 12/1999 | Lin | |
| 6,004,500 A | 12/1999 | Safari | |
| 6,007,765 A | 12/1999 | Oversberg | |
| 6,011,265 A | 1/2000 | Sauli | |
| 6,014,419 A | 1/2000 | Hu | |
| 6,017,410 A | 1/2000 | Baccini | |
| 6,018,422 A | 1/2000 | Feldman | |
| 6,018,566 A | 1/2000 | Eberhard et al. | |
| 6,018,680 A | 1/2000 | Flower | |
| 6,021,358 A | 2/2000 | Sachs | |
| 6,055,899 A | 5/2000 | Feit et al. | |
| 6,068,684 A | 5/2000 | Overton | |
| 6,075,840 A | 6/2000 | Pellegrino | |
| 6,084,626 A | 7/2000 | Ramanujan et al. | |
| 6,084,980 A | 7/2000 | Nguyen | |
| 6,088,102 A | 7/2000 | Manhart | |
| 6,124,663 A | 9/2000 | Haake et al. | |
| 6,126,775 A | 10/2000 | Cullen | |
| 6,133,670 A | 10/2000 | Rodgers et al. | |
| 6,134,294 A | 10/2000 | Gibbs | |
| 6,149,160 A | 11/2000 | Stephens et al. | |
| 6,152,181 A | 11/2000 | Wapner | |
| 6,155,634 A | 12/2000 | Oehlerking et al. | |
| 6,159,407 A * | 12/2000 | Krinke et al. | 264/219 |
| 6,165,406 A | 12/2000 | Jang | |
| 6,175,615 B1 | 1/2001 | Guru et al. | |
| 6,179,601 B1 | 1/2001 | Kruger | |
| 6,185,278 B1 | 2/2001 | Appleby | |
| 6,188,743 B1 | 2/2001 | Tybinkowski et al. | |
| 6,190,594 B1 * | 2/2001 | Gorman et al. | 264/167 |
| 6,193,923 B1 | 2/2001 | Leyden | |
| 6,197,180 B1 | 3/2001 | Kelly | |
| 6,210,644 B1 | 4/2001 | Trokhan | |
| 6,219,015 B1 | 4/2001 | Bloom et al. | |
| 6,226,120 B1 | 5/2001 | Feldman | |
| 6,230,408 B1 | 5/2001 | Ehrfeld et al. | |
| 6,241,934 B1 | 6/2001 | Everett et al. | |
| 6,242,163 B1 | 6/2001 | Stampfl | |
| 6,245,184 B1 | 6/2001 | Riedner | |
| 6,245,249 B1 | 6/2001 | Yamada | |
| 6,245,487 B1 | 6/2001 | Randall | |
| 6,245,849 B1 | 6/2001 | Morales et al. | |
| 6,250,070 B1 | 6/2001 | Kreiner et al. | |
| 6,252,938 B1 | 6/2001 | Tang | |
| 6,261,066 B1 | 7/2001 | Linnemann et al. | |
| 6,261,506 B1 | 7/2001 | Nguyen | |
| 6,270,335 B2 | 8/2001 | Leyden | |
| 6,276,313 B1 | 8/2001 | Yang et al. | |
| 6,280,090 B1 | 8/2001 | Stephens et al. | |
| 6,299,300 B1 | 10/2001 | Silverbrook | |
| 6,307,815 B1 | 10/2001 | Polosky et al. | |
| 6,310,419 B1 | 10/2001 | Wood | |
| 6,314,887 B1 | 11/2001 | Robinson | |
| 6,318,069 B1 | 11/2001 | Falce et al. | |
| 6,318,849 B1 | 11/2001 | Silverbrook | |
| 6,324,748 B1 | 12/2001 | Dhuler et al. | |
| 6,328,903 B1 | 12/2001 | Vernon | |
| 6,333,584 B1 | 12/2001 | Jerman et al. | |
| 6,336,318 B1 | 1/2002 | Falce et al. | |
| 6,338,199 B1 | 1/2002 | Chigira et al. | |
| 6,338,249 B1 | 1/2002 | Pai | |
| 6,340,222 B1 | 1/2002 | Silverbrook | |

| | | | | | | |
|---|---|---|---|---|---|---|
| 6,344,392 | B1 | 2/2002 | Liaw | 6,471,471 B1 | 10/2002 | Bouyer |
| 6,346,030 | B1 | 2/2002 | Morales | 6,471,800 B2 | 10/2002 | Jang |
| 6,350,983 | B1 | 2/2002 | Kaldor et al. | 6,472,459 B2 * | 10/2002 | Morales et al. ............. 524/439 |
| 6,352,656 | B1 | 3/2002 | Kimura et al. | 6,480,320 B2 | 11/2002 | Nasiri |
| 6,360,424 | B1 | 3/2002 | Mehregany et al. | 6,490,496 B1 | 12/2002 | Dacey |
| 6,363,712 | B1 | 4/2002 | Sniegowski et al. | 6,505,089 B1 | 1/2003 | Yang |
| 6,363,843 | B1 | 4/2002 | Daniel et al. | 6,508,971 B2 | 1/2003 | Leyden et al. |
| 6,367,911 | B1 | 4/2002 | Windel et al. | 6,519,500 B1 | 2/2003 | White |
| 6,373,158 | B1 | 4/2002 | Hsu et al. | 6,557,607 B2 | 5/2003 | Yamada |
| 6,375,871 | B1 | 4/2002 | Bentsen et al. | 6,575,218 B1 | 6/2003 | Burns |
| 6,376,148 | B1 | 4/2002 | Liu | 6,611,731 B2 | 8/2003 | Duffin |
| 6,381,846 | B2 | 5/2002 | Insley et al. | 6,627,030 B2 | 9/2003 | Yang |
| 6,382,588 | B1 | 5/2002 | Hierold | 6,627,835 B1 | 9/2003 | Chung |
| 6,386,015 | B1 | 5/2002 | Rader et al. | 6,660,209 B2 | 12/2003 | Leyden |
| 6,387,713 | B2 | 5/2002 | Hara | 6,682,688 B1 | 1/2004 | Higashi et al. |
| 6,392,187 | B1 | 5/2002 | Johnson | 6,713,199 B2 | 3/2004 | Girardie |
| 6,392,313 | B1 | 5/2002 | Epstein et al. | 6,731,438 B2 | 5/2004 | Stern |
| 6,392,524 | B1 | 5/2002 | Biegelsen et al. | 6,745,446 B1 | 6/2004 | Barlier |
| 6,393,685 | B1 | 5/2002 | Collins | 6,780,368 B2 | 8/2004 | Liu |
| 6,395,126 | B1 | 5/2002 | Cullen et al. | 6,812,061 B1 | 11/2004 | Feierabend et al. |
| 6,396,677 | B1 | 5/2002 | Chua et al. | 6,829,536 B2 | 12/2004 | Moore |
| 6,397,677 | B1 | 6/2002 | Kinsley et al. | 6,881,950 B2 | 4/2005 | Schlaf |
| 6,397,793 | B2 | 6/2002 | Yang et al. | 7,057,245 B2 | 6/2006 | Feierabend et al. |
| 6,398,490 | B1 | 6/2002 | Antonsson | 7,077,638 B2 | 7/2006 | Leyden |
| 6,399,010 | B1 | 6/2002 | Guertin et al. | 7,141,080 B2 | 11/2006 | Feierabend et al. |
| 6,401,004 | B1 | 6/2002 | Yamazaki | 7,170,140 B2 | 1/2007 | Dutoit et al. |
| 6,404,942 | B1 | 6/2002 | Edwards et al. | 7,203,569 B2 | 4/2007 | Liang |
| 6,406,658 | B1 | 6/2002 | Manners et al. | 7,235,166 B2 | 6/2007 | Cohen |
| 6,408,884 | B1 | 6/2002 | Kamholz et al. | 7,252,861 B2 | 8/2007 | Smalley |
| 6,409,072 | B1 | 6/2002 | Breuer et al. | 2001/0031531 A1 | 10/2001 | Liaw |
| 6,410,213 | B1 | 6/2002 | Raguin et al. | 2001/0034114 A1 | 10/2001 | Liaw |
| 6,415,860 | B1 | 7/2002 | Kelly et al. | 2002/0093115 A1 | 7/2002 | Jang |
| 6,416,168 | B1 | 7/2002 | Silverbrook | 2002/0149137 A1 | 10/2002 | Jang |
| 6,433,657 | B1 | 8/2002 | Chen | 2002/0181647 A1 | 12/2002 | Venkataramani et al. |
| 6,438,210 | B1 | 8/2002 | Castleberry | 2003/0128812 A1 | 7/2003 | Appleby et al. |
| 6,440,284 | B1 | 8/2002 | Dubrow | 2003/0128813 A1 | 7/2003 | Appleby et al. |
| 6,445,840 | B1 | 9/2002 | Fernandez et al. | 2004/0006405 A1 | 1/2004 | Chen |
| 6,447,727 | B1 | 9/2002 | Parce et al. | 2004/0128016 A1 | 7/2004 | Stewart |
| 6,450,047 | B2 | 9/2002 | Swedberg et al. | 2005/0206048 A1 | 9/2005 | Ryu |
| 6,453,083 | B1 | 9/2002 | Husain et al. | 2007/0036844 A1 | 2/2007 | Ma |
| 6,454,945 | B1 | 9/2002 | Weigl et al. | 2007/0158014 A1 | 7/2007 | Schwenn |
| 6,457,629 | B1 | 10/2002 | White | | | |
| 6,458,263 | B1 | 10/2002 | Morales et al. | | | |
| 6,462,858 | B1 | 10/2002 | MacDonald et al. | | | |
| 6,463,349 | B2 | 10/2002 | White | | | |
| 6,467,138 | B1 | 10/2002 | Aime | | | |
| 6,468,309 | B1 | 10/2002 | Lieberman | | | |

OTHER PUBLICATIONS

Hexcel Corporation, "Hex Web Honeycomb Attributes and Properties", Nov. 1, 1999, 39 pages.

* cited by examiner

3000
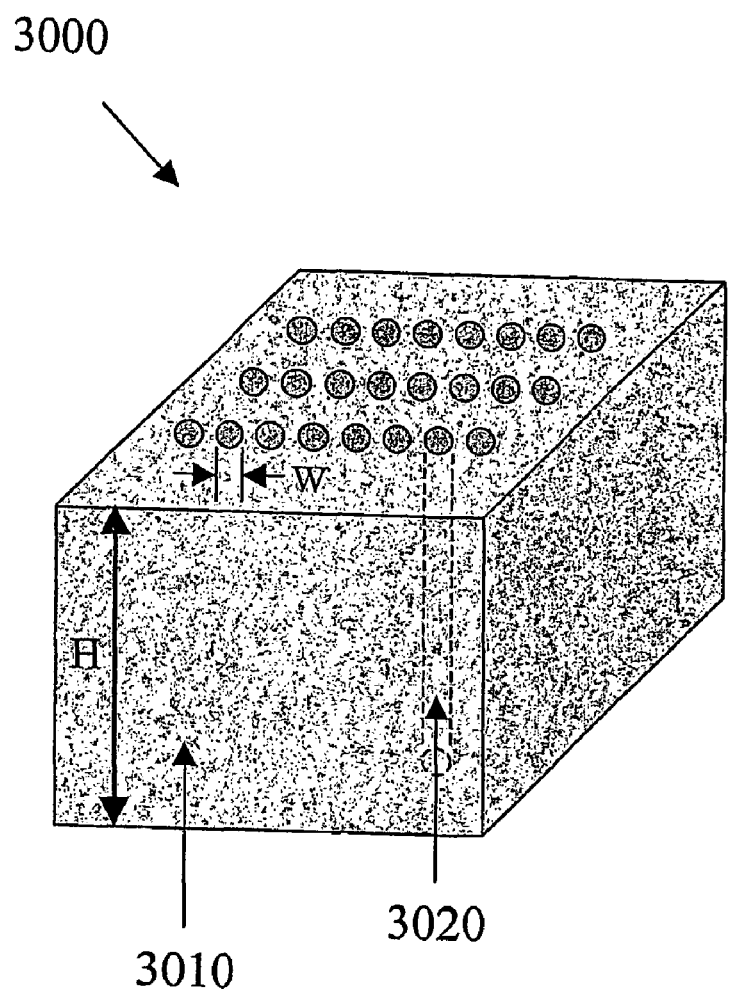
3010
3020
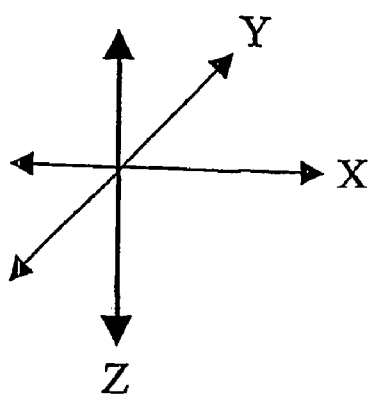
FIG. 3

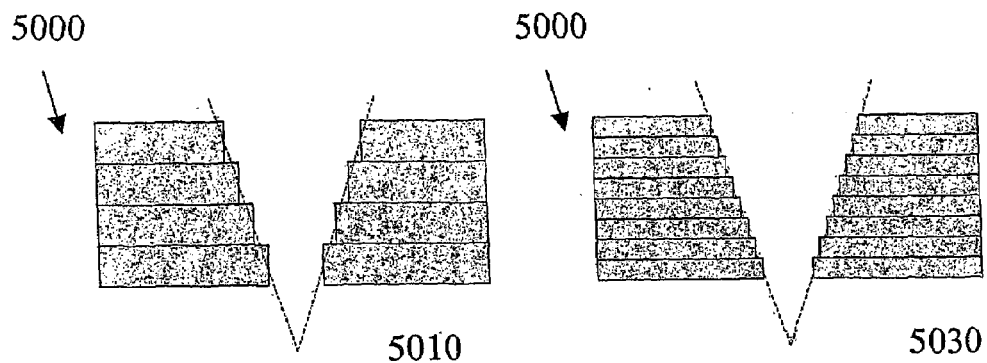
FIG. 5B  FIG. 5C
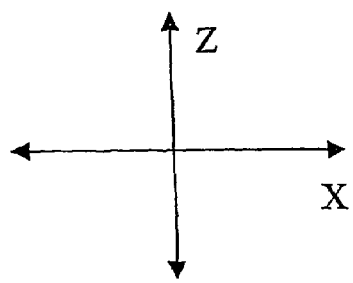
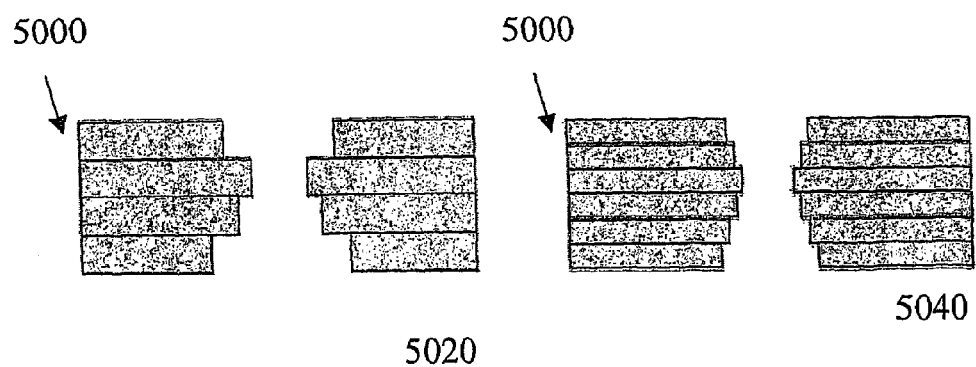
FIG. 5D  FIG. 5E

10010

10020

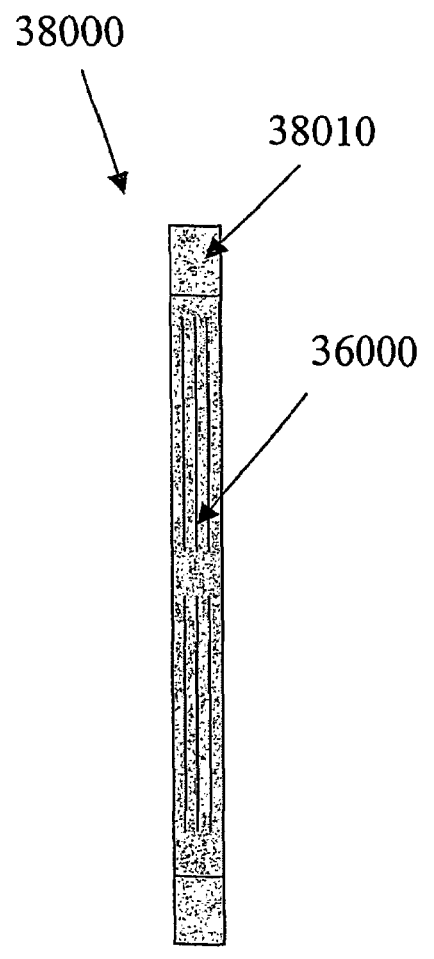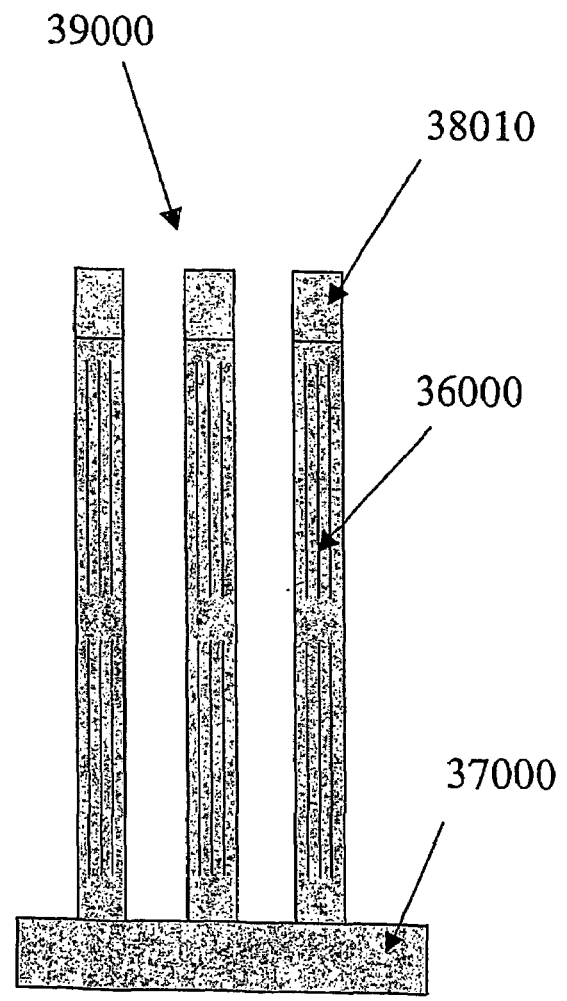
FIG. 38  FIG. 39

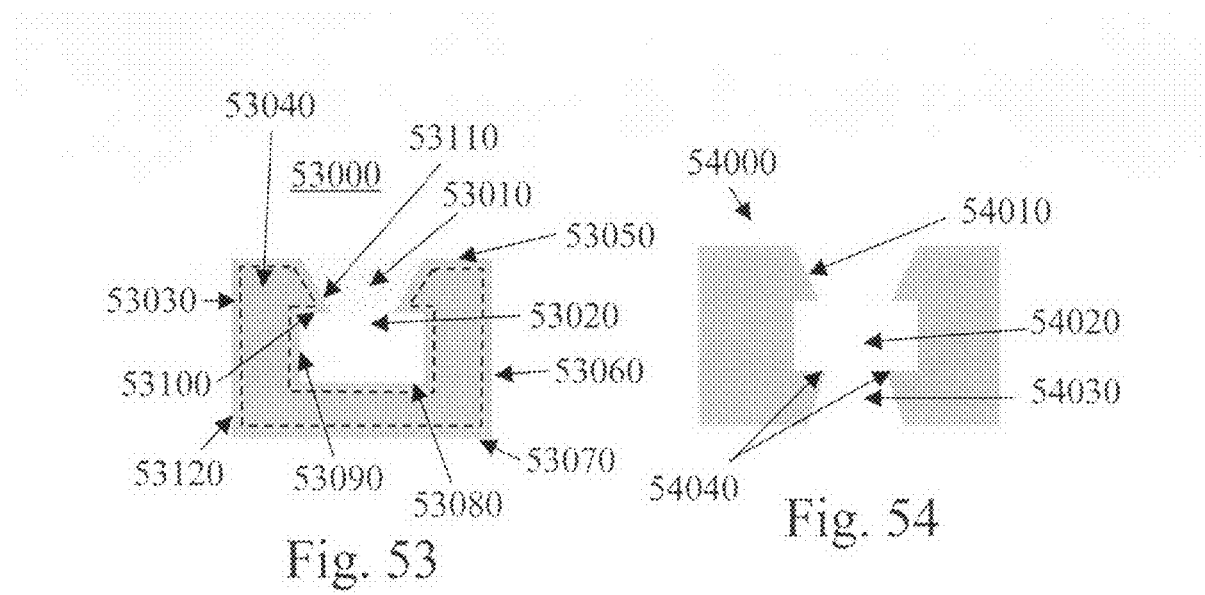
Fig. 53
Fig. 54
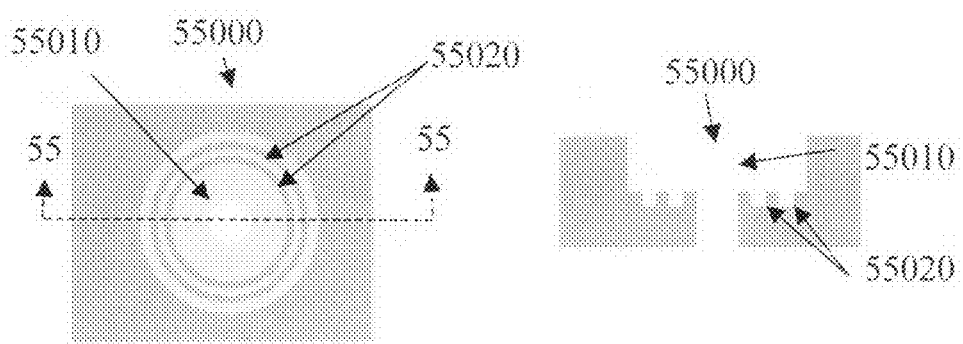
Fig. 55
Fig. 56

METHODS FOR MANUFACTURING THREE-DIMENSIONAL DEVICES AND DEVICES CREATED THEREBY

CROSS REFERENCE TO RELATED APPLICATIONS

This application claims priority to, and incorporates by reference in their entirety, each of: pending U.S. Application Ser. No. 60/295,564, filed 5 Jun. 2001, and pending U.S. Application Ser. No. 60/339,773, filed 17 Dec. 2001.

BRIEF DESCRIPTION OF THE DRAWINGS

The invention and its wide variety of potential embodiments will be more readily understood through the following detailed description, with reference to the accompanying drawings in which:

FIG. 3 is a perspective view of an exemplary casting of the present invention that illustrates aspect ratio.

FIGS. 5B-5E are exemplary alternative cross-sectional views of an exemplary stack lamination mold of the present invention taken at section lines 5-5 of FIG. 5A.

FIG. 38 is a front view of a single exemplary flexible cavity insert assembly of the present invention.

FIG. 39 is a front view of flexible cavity inserts of the present invention.

FIG. 50 is a cross-sectional view of an alternative exemplary microdevice of the present invention, taken at section lines 48-48 of FIG. 48A, and shown with an inlet valve open.

FIG. 51 is a cross-sectional view of the alternative exemplary microdevice of

FIG. 50, taken at section lines 48-48 of FIG. 48A, and shown with an outlet valve open.

FIG. 53 is a cross-sectional view taken at lines 52-52 of FIG. 52 of an exemplary microwell of the present invention.

FIG. 54 is a cross-sectional view taken at lines 52-52 of FIG. 52 of an alternative exemplary microwell of the present invention.

FIG. 55 is a top view of exemplary microwell of the present invention.

FIG. 56 is a cross-sectional view of an exemplary microwell of the present invention, taken at lines 55-55 of FIG. 55.

DETAILED DESCRIPTION

Certain exemplary embodiments of the present invention can combine certain techniques of stack lamination with certain molding processes to manufacture a final product. As a result of the stack lamination techniques, precision microscale cavities of predetermined shapes can be engineered into the stack lamination. Rather than have the stack lamination embody the final product, however, the stack lamination can be used as an intermediate in a casting or molding process.

In certain exemplary embodiments of the present invention, the stack lamination ("laminated mold") can be made up of layers comprising metallic, polymeric, and/or ceramic material. The mold can be a positive replication of a predetermined end product or a negative replication thereof. The mold can be filled with a first cast material and allowed to solidify. A first cast product can be demolded from the mold. The first cast material can comprise a flexible polymer such as silicone rubber.

Certain exemplary embodiments of a method of the present invention can further include surrounding the first cast product with a second casting material and allowing the second cast material to solidify. Still further, a second cast product can be demolded from the first cast product.

Some exemplary embodiments of the present invention can further include positioning an insert into the cavity prior to filling the mold with the first cast material, wherein the insert occupies only a portion of the space defined by the cavity. The second cast product can be nonplanar. The end product and/or the mold cavity can have an aspect ratio greater that 100:1. The end product can be attached to the substrate or it can be a free-standing structure.

Figure 1:
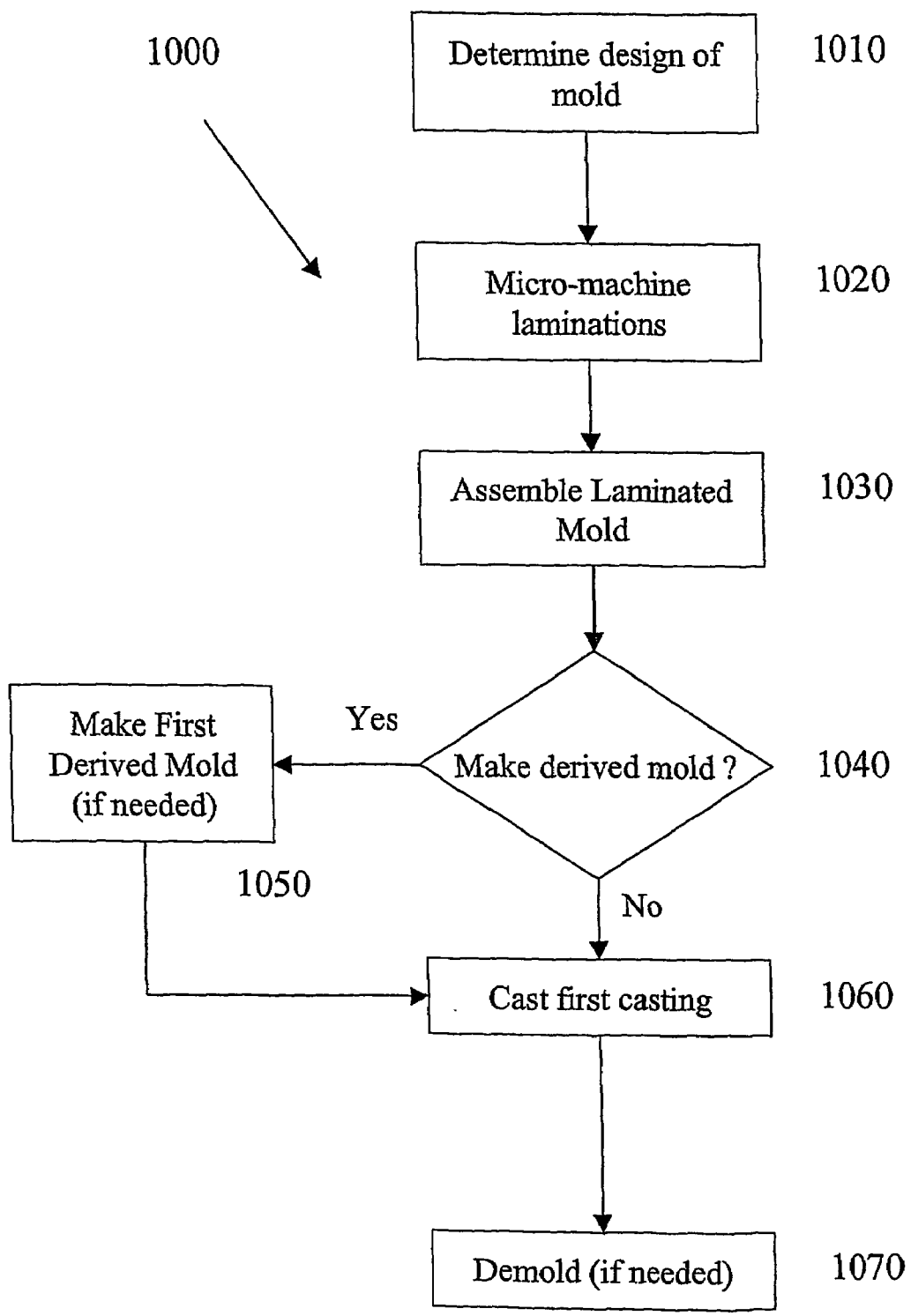
FIG. 1 is a flowchart of an exemplary embodiment of a method of the present invention.

FIG. 1 is a flowchart of an exemplary embodiment of a method 1000 of the present invention. At activity 1010, a mold design is determined. At activity 1020, the layers of the mold ("laminations") are fabricated. At activity 1030, the laminations are stacked and assembled into a mold (a derived mold could be produced at this point as shown in FIG. 1). At activity 1060, a first casting is cast. At activity 1070, the first casting is demolded.

Figure 2:
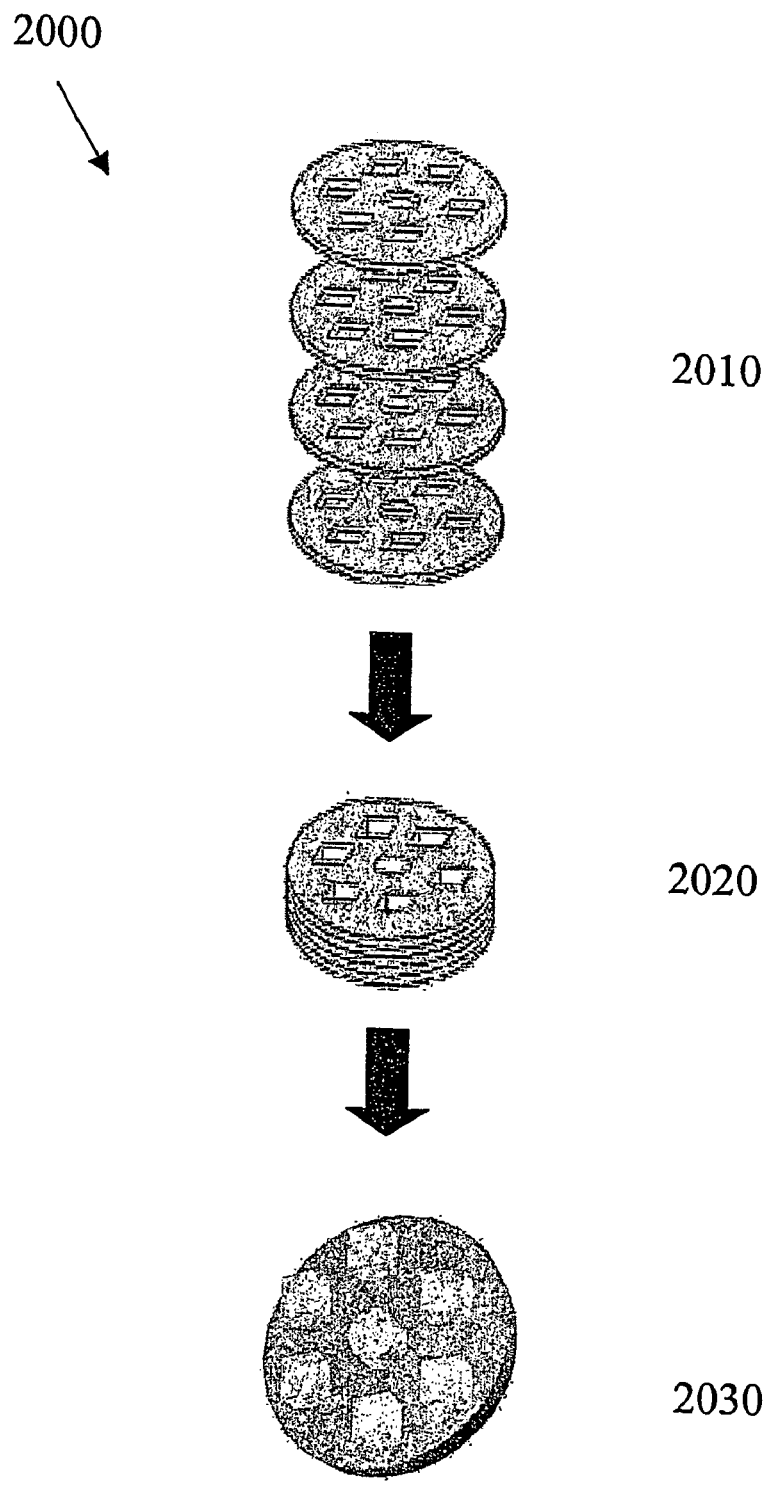
FIG. 2 is a flow diagram of exemplary items fabricated using a method of the present invention.

FIG. 2 is a flow diagram of exemplary items fabricated during a method 2000 of the present invention. Layers 2010 can be stacked to form a mold or stacked lamination 2020. A molding or casting material can be applied to mold 2020 to create a molding or casting 2030, that can be demolded from mold 2020.

FIG. 3 is a perspective view of an exemplary molding 3000 of the present invention that demonstrates a parameter referred to herein as "aspect ratio" which is described below. Molded block 3010 has numerous through-holes 3020, each having a height H and a diameter or width W. For the purposes of this application, aspect ratio is defined as the ratio of height to width or H/W of a feature, and can apply to any "negative" structural feature, such as a space, channel, through-hole, cavity, etc., and can apply to a "positive" feature, such as a wall, projection, protrusion, etc., with the height of the feature measured along the Z-axis. Note that all features can be "bordered" by at least one "wall". For a positive feature, the wall is part of the feature. For a negative feature, the wall at least partially defines the feature.

FIG. 3 also demonstrates the X-, Y-, and Z-directions or axes. For the purposes of this application, the dimensions measured in the X- and Y-directions define a top surface of a structure (such as a layer, a stack lamination mold, or negative and/or positive replications thereof) when viewed from the top of the structure. The Z-direction is the third dimension perpendicular to the X-Y plane, and corresponds to the line of sight when viewing a point on a top surface of a structure from directly above that point.

Certain embodiments of a method of the present invention can control aspect ratios for some or all features in a laminated mold, derived mold, and/or cast item (casting). The ability to attain relatively high aspect ratios can be affected by a feature's geometric shape, size, material, and/or proximity to another feature. This ability can be enhanced using certain embodiments of the present invention. For example, through-features of a mold, derived mold, and/or final part, having a width or diameter of approximately 5 microns, can have a dimension along the Z axis (height) of approximately 100 microns, or approximately 500 microns, or any value in the range there between (implying an aspect ratio of approximately 20:1, 100:1, or any value in the range therebetween, including, for example:

20:1 to 30:1, 20:1 to 40:1, 20:1 to 50:1, 20:1 to 60:1, 20:1 to 70:1, 20:1 to 80:1, 20:1 to 90:1, 20:1 to 100:1,

30:1 to 40:1, 30:1 to 50:1, 30:1 to 60:1, 30:1 to 70:1, 30:1 to 80:1, 30:1 to 90:1, 30:1 to 100:1,

40:1 to 50:1, 40:1 to 60:1, 40:1 to 70:1, 40:1 to 80:1, 40:1 to 90:1, 40:1 to 100:1,

50:1 to 60:1, 50:1 to 70:1, 50:1 to 80:1, 50:1 to 90:1, 50:1 to 100:1,

60:1 to 70:1, 60:1 to 80:1, 60:1 to 90:1, 60:1 to 100:1,

70:1 to 80:1, 70:1 to 90:1, 70:1 to 100:1,

80:1 to 90:1, 80:1 to 100:1, etc).

As another example, a through slit having a width of approximately 20 microns can have a height of approximately 800 microns, or approximately 1600 microns, or any value in the range therebetween (implying an aspect ratio of approximately 40:1, 80:1, or any value in the range therebetween, including, for example:

40:1 to 50:1, 40:1 to 60:1, 40:1 to 70:1, 40:1 to 80:1,

50:1 to 60:1, 50:1 to 70:1, 50:1 to 80:1,

60:1 to 70:1, 60:1 to 80:1,

70:1 to 80:1, etc).

As yet another example, the same approximately 20 micron slit can be separated by an approximately 15 micron wide wall in an array, where the wall can have a dimension along the Z axis (height) of approximately 800 microns, or approximately 1600 microns, or any value in the range therebetween (implying an aspect ratio of approximately 53:1, 114:1, or any value in the range therebetween, including, for example:

53:1 to 60:1, 53:1 to 70:1, 53:1 to 80:1, 53:1 to 90:1, 53:1 to 100:1, 53:1 to 110:1, 53:1 to 114:1,

60:1 to 70:1, 60:1 to 80:1, 60:1 to 90:1, 60:1 to 100:1, 60:1 to 110:1, 60:1 to 114:1,

70:1 to 80:1, 70:1 to 90:1, 70:1 to 100:1, 70:1 to 110:1, 70:1 to 114:1,

80:1 to 90:1, 80:1 to 100:1, 90:1 to 110:1, 90:1 to 114:1,

90:1 to 100:1, 90:1 to 110:1, 90:1 to 114:1,

100:1 to 110:1, 100:1 to 114:1, etc.).

Still another example is an array of square-shaped openings having sides that are approximately 0.850 millimeters wide, each opening separated by approximately 0.150 millimeter walls, with a dimension along the Z axis of approximately 30 centimeters. In this example the approximately 0.850 square openings have an aspect ratio of approximately 353:1, and the approximately 0.150 walls have an aspect ratio of approximately 2000:1, with lesser aspect ratios possible. Thus, the aspect ratio of the openings can be approximately 10:1, or approximately 350:1, or any value in the range therebetween, including for example:

10:1 to 20:1, 10:1 to 30:1, 10:1 to40:1, 10:1 to 50:1, 10:1 to 60:1, 10:1 to 70:1, 10:1 to 80:1, 10:1 to 90:1, 10:1 to 100:1, 10:1 to 150:1, 10:1 to 200:1, 10:1 to 250:1, 10:1 to 300:1, 10:1 to 350:1,

20:1 to 30:1, 20:1 to 40:1, 20:1 to 50:1, 20:1 to 60:1, 20:1 to 70:1, 20:1 to 80:1, 20:1 to 90:1, 20:1 to 100:1, 20:1 to 150:1, 20:1 to 200:1, 20:1 to 250:1, 20:1 to 300:1, 20:1 to 350:1,

30:1 to 40:1, 30:1 to 50:1, 30:1 to 60:1, 30:1 to 70:1, 30:1 to 80:1,30:1 to 90:1, 30:1 to 100:1, 30:1 to 150:1, 30:1 to 200:1, 30:1 to 250:1, 30:1 to 300:1, 30:1 to 350:1,

40:1 to 50:1, 40:1 to 60:1, 40:1 to 70:1, 40:1 to 80:1,40:1 to 90:1,40:1 to 100:1, 40:1 to 150:1, 40:1 to 200:1, 40:1 to 250:1, 40:1 to 300:1, 40:1 to 350:1,

50:1 to 60:1, 50:1 to 70:1, 50:1 to 80:1, 50:1 to 90:1, 50:1 to 100:1, 50:1 to 150:1, 50:1 to 200:1, 50:1 to 250:1, 50:1 to 300:1, 50:1 to 350:1,

75:1 to 80:1, 75:1 to 90:1, 75:1 to 100:1, 75:1 to 150:1, 75:1 to 200:1, 75:1 to 250:1, 75:1 to 300:1, 75:1 to 350:1,

100:1 to 150:1, 100:1 to 200:1, 100:1 to 250:1, 100:1 to 300:1, 100:1 to 350:1,

150:1 to 200:1, 150:1 to 250:1, 150:1 to 300:1, 150:1 to 350:1,

200:1 to 250:1, 200:1 to 300:1, 200:1 to 350:1,

250:1 to 300:1, 250:1 to 350:1,

300:1 to 350:1, etc.

Moreover, the aspect ratio of the walls can be approximately 10:1, or approximately 2000:1, or any value in the range therebetween, including for example:

10:1 to 20:1, 10:1 to 30:1, 10:1 to 40:1, 10:1 to 50:1, 10:1 to 100:1, 10:1 to 10 200:1, 10:1 to 500:1, 10:1 to 1000:1, 10:1 to 2000:1,

20:1 to 30:1, 20:1 to 40:1, 20:1 to 50:1, 20:1 to 100:1, 20:1 to 200:1, 20:1 to 500:1, 20:1 to 1000:1, 20:1 to 2000:1,

30:1 to 40:1, 30:1 to 50:1, 30:1 to 100:1, 30:1 to 200:1, 30:1 to 500:1, 30:1 to 1000:1, 30:1 to 2000:1,

40:1 to 50:1, 40:1 to 100:1, 40:1 to 200:1, 40:1 to 500:1, 40:1 to 1000:1, 40:1 to 2000:1,

50:1 to 100:1, 50:1 to 200:1, 50:1 to 500:1, 50:1 to 1000:1, 50:1 to2000:1,

100:1 to 200:1, 100:1 to 500:1, 100:1 to 1000:1, 100:1 to 2000:1,

200:1 to 500:1, 200:1 to 1000:1, 200:1 to 2000:1,

500:1 to 1000:1, 500:1 to 2000:1,

1000:1 to 2000:1, etc.

Another example of aspect ratio is the space between solid (positive) features of a mold, derived mold, and/or casting. For example, as viewed from the top, a casting can have two or more solid rectangles measuring approximately 50 microns wide by approximately 100 microns deep with an approximately 5 micron space therebetween (either widthwise or depth-wise). The rectangles can have a height of 100 microns, or 500 microns, or any value in the range therebetween (implying an aspect ratio of 20:1, or 100:1, or any value therebetween, including, for example:

20:1 to 30:1, 20:1 to 40:1, 20:1 to 50:1, 20:1 to 60:1, 20:1 to 70:1,20:1 to 80:1, 20:1 to 90:1, 20:1 to 100:1,

30:1 to 40:1, 30:1 to 50:1, 30:1 to 60:1, 30:1 to 70:1, 30:1 to 80:1,30:1 to 90:1, 30:1 to 100:1,

40:1 to 50:1, 40:1 to 60:1, 40:1 to 70:1, 40:1 to 80:1, 40:1 to 90:1, 40:1 to 100:1,

50:1 to 60:1, 50:1 to 70:1, 50:1 to 80:1, 50:1 to 90:1, 50:1 to 100:1,

60:1 to 70:1, 60:1 to 80:1, 60:1 to 90:1, 60:1 to 100:1,

70:1 to 80:1, 70:1 to 90:1, 70:1 to 100:1,

80:1 to 90:1, 80:1 to 100:1, etc).

In another example the same rectangles can have a space there between of approximately 20 microns, and the rectangles can have dimensions along the Z axis of approximately 800 microns, or approximately 5000 microns, or any value therebetween (implying an aspect ratio of approximately 40:1, or 250:1, or any value therebetween, including, for example:

40:1 to 50:1, 40:1 to 75:1, 40:1 to 100:1, 40:1 to 150:1, 40:1 to 200:1, 40:1 to 15 250:1,

75:1 to 100:1, 75:1 to 150:1, 75:1 to 200:1, 75:1 to 250:1,

100:1 to 150:1, 100:1 to 200:1, 100:1 to 250:1,

150:1 to 200:1, 150:1 to 250:1,

200:1 to 250:1, etc).

Figure 4:
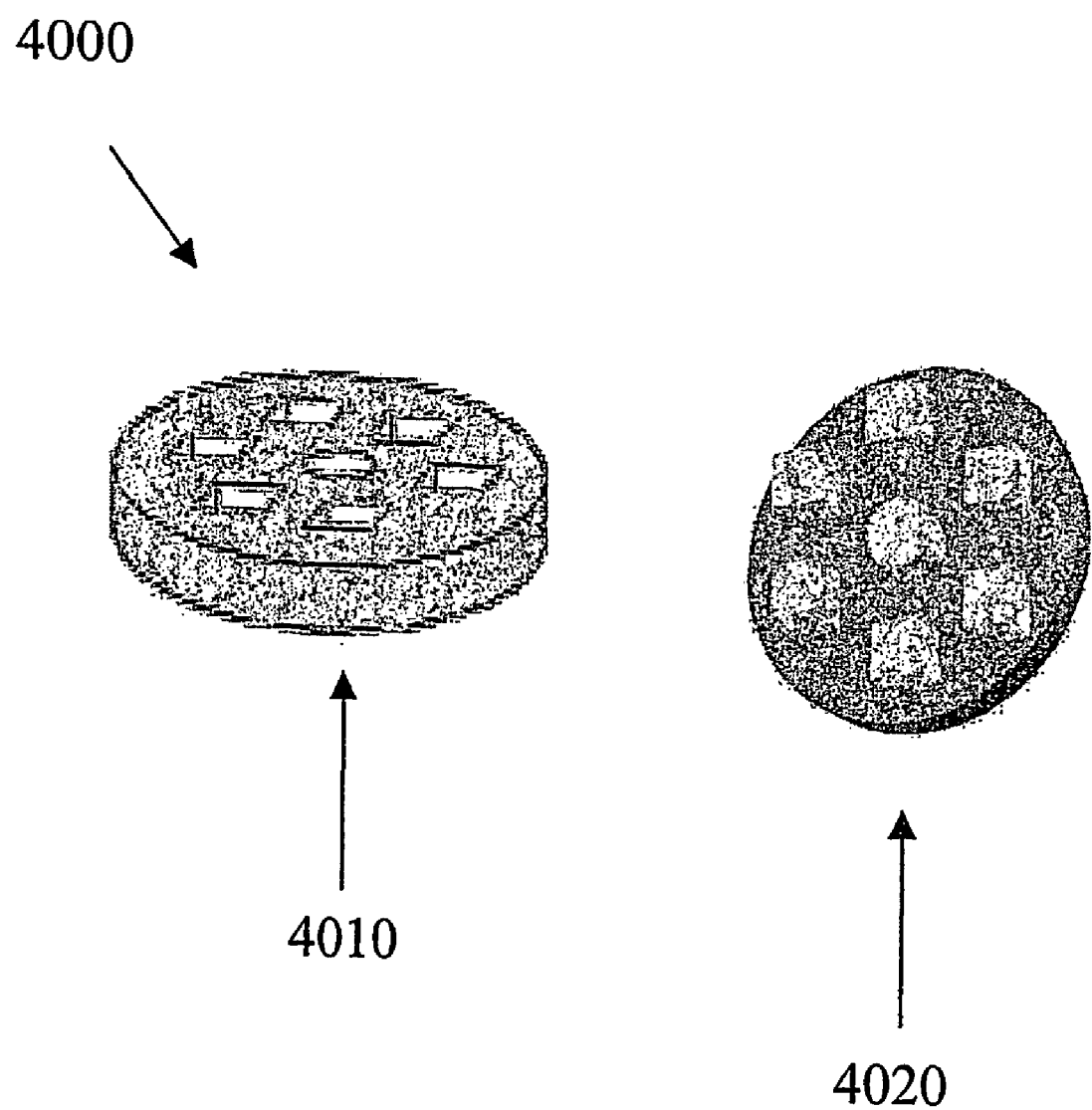
FIG. 4 is an assembly view of an exemplary assembly of the present invention.

FIG. 4 is an assembly view of an exemplary assembly 4000 of the present invention that includes mold 4010 and cast part 4020 formed from mold 4010. Because certain exemplary embodiments of the present invention can utilize lithographically-derived micro-machining techniques (or in some cases, non-lithographically-derived micro-machining techniques, such as laser machining) combined with molding and/or casting, laminated molds can be conceived as negatives 4010 or positives 4020 of the desired end product. The terms "negative" or "positive" replications can be subjective terms assigned to different stages of reaching an end product. For certain embodiments, any intermediate or the end product can be considered a negative or positive replication depending on a subject's point of view. For the purpose of this application, a "positive" replication is an object (whether an intermediate or an end product) that geometrically resembles at least a portion of the spatial form of the end product. Conversely, a "negative" replication is a mold that geometrically defines at least a portion of the spatial form of the end product. The following parameters are described for the purpose of demonstrating some of the potential design parameters of certain embodiments of a method of the present invention.

Layer Thickness

Figure 5A:
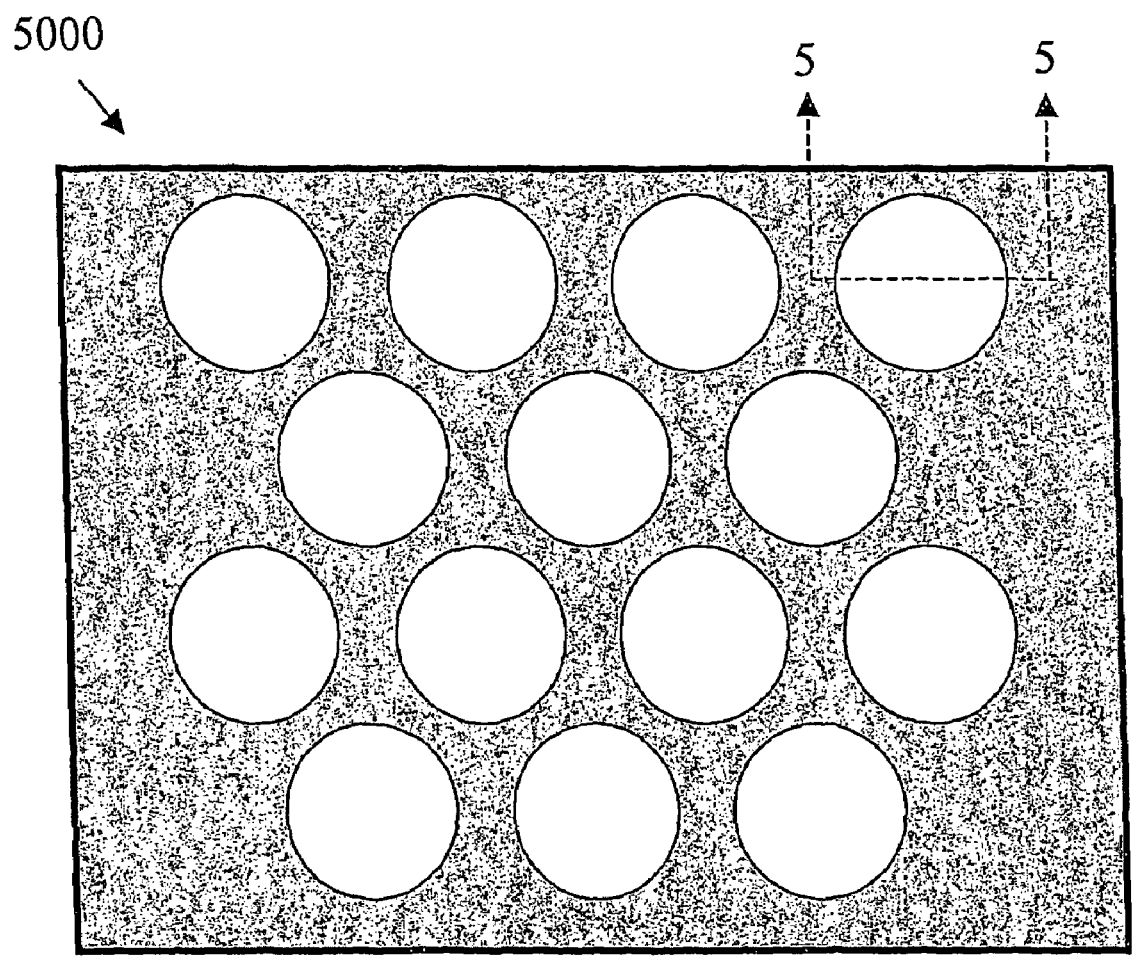
FIG. 5A is a top view of an exemplary stack lamination mold of the present invention.

One design parameter can be the thickness of the micromachined layers of the stack lamination mold. According to certain exemplary embodiments of the present invention, to achieve high-aspect ratios, multiple micro-machined foils or layers can be stacked in succession and bonded together. In certain exemplary embodiments of the present invention, the layer thickness can have a dimensional role in creating the desired shape in the third dimension. FIG. 5A is a top view of an exemplary stack lamination mold 5000. FIGS. 5B-5E are exemplary alternative cross-sectional views of exemplary stack lamination mold 5000 taken at section lines 5-5 of FIG. 5A. As shown in FIG. 5B and FIG. 5D, respectively, stacks 5010 and 5020 utilize relatively thick layers. As shown in FIG. 5C and FIG. 5E, respectively, stacks 5030 and 5040 utilize relatively thinner layers in succession to smooth out resolution along the z-axis. Specific layers can have multiple functions that can be achieved through their thickness or other incorporated features described herein.

Cross-sectional Shape of Layer

Figure 6:
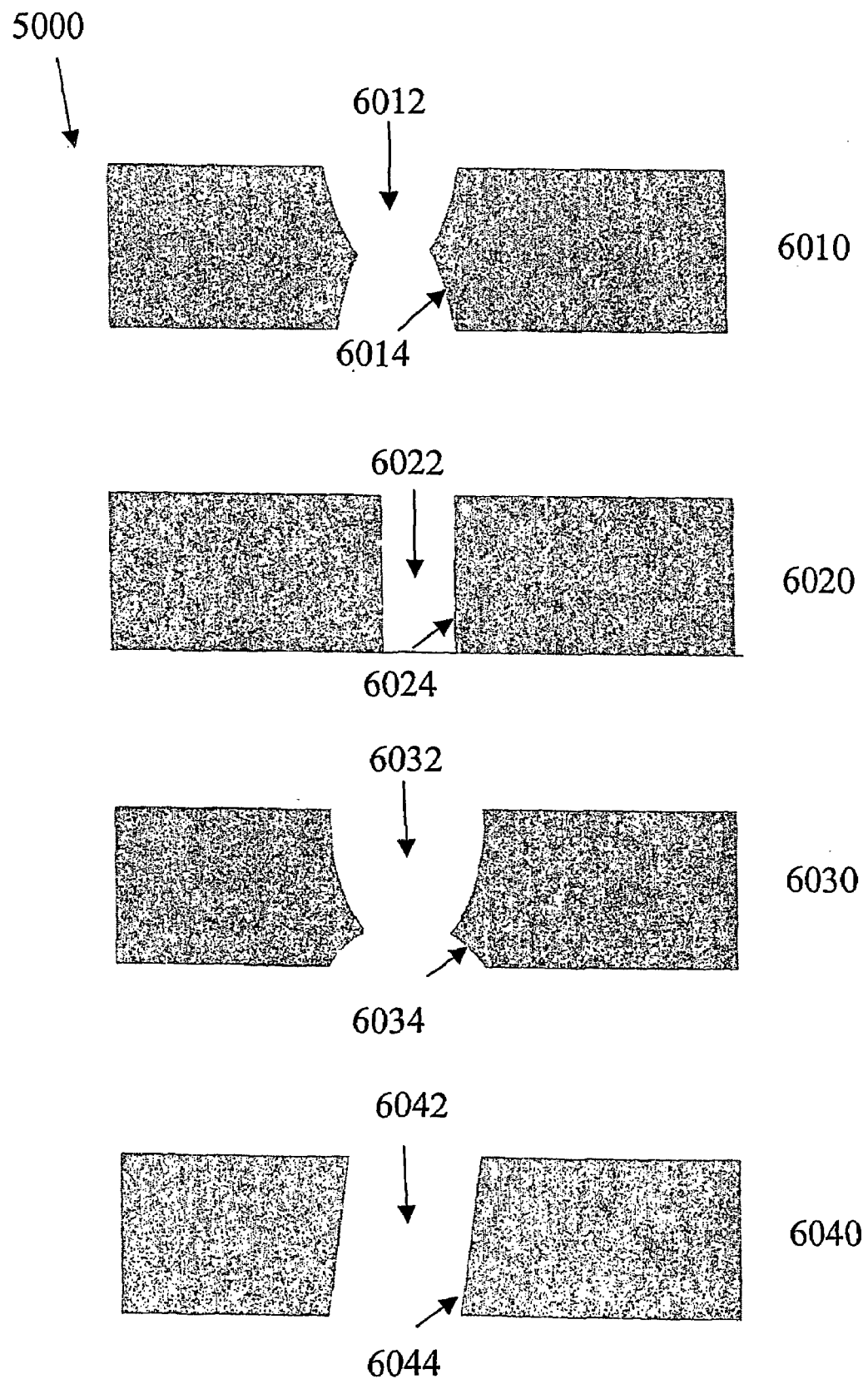
FIG. 6 is an unassembled cross-sectional view of an alternative exemplary stack lamination mold taken of the present invention at section lines 5-5 of FIG. 5A.

One design parameter can be the cross sectional shape of a given layer in the mold. Through the use of etching and/or deposition techniques, many cross sectional shapes can be obtained. FIG. 6 is an unassembled cross-sectional view of an alternative exemplary stack lamination mold 5000 taken at section lines 5-5 of FIG. 5A. Each of exemplary layers 6010, 6020, 6030, and 6040 of FIG. 6 define an exemplary through-feature 6012, 6022, 6032, 6042, respectively, each having a different shape, orientation, and/or configuration. These through-features 6012, 6022, 6032, 6042 are bordered by one or more "sidewalls" 6014, 6024, 6034, and 6044, respectively, as they are commonly referred to in the field of lithographic micro-machining.

Etching disciplines that can be utilized for a layer of the mold can be broadly categorized as isotropic (non-linear) or anisotropic (linear), depending on the shape of the remaining sidewalls. Isotropic often refers to those techniques that produce one or more radial or hour glassed shaped sidewalls, such as those shown in layer 6010. Anisotropic techniques produce one or more sidewalls that are more vertically straight, such as those shown in layer 6020.

Additionally, the shape of a feature that can be etched through a foil of the mold can be controlled by the depth of etching on each surface and/or the configuration of the photo-mask. In the case of photo-chemical-machining, a term such as 90/10 etching is typically used to describe the practice of etching 90% through the foil thickness, from one side of the foil, and finishing the etching through the remaining 10% from the other side, such as shown on layer 6030. Other etch ratios can be obtained, such as 80/20, 70/30, and/or 65/35, etc., for various foils and/or various features on a given foil.

Also, the practice of displacing the positional alignment of features from the top mask to the bottom mask can be used to alter the sidewall conditions for a layer of the mold, such as shown in layer 6040.

Figure 7:
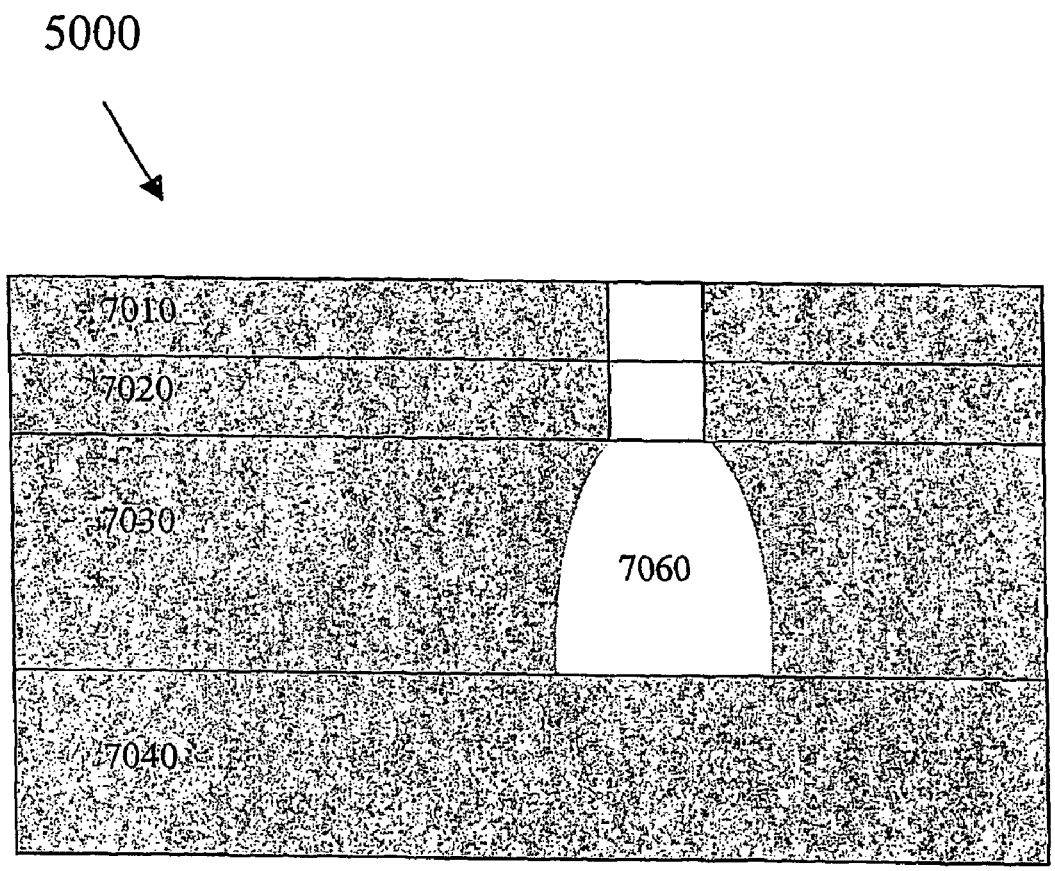
FIG. 7 is a cross-sectional view of an exemplary alternative stack lamination mold of the present invention taken at section lines 5-5 of FIG. 5A.

By using these and/or other specific conditions as design parameters, layers can be placed to contribute to the net shape of the 3-dimensional structure, and/or provide specific function to that region of the device. For example, an hourglass sidewall could be used as a fluid channel and/or to provide structural features to the device. FIG. 7 is a cross-sectional view of an alternative exemplary stack lamination mold taken at section line 5-5 of FIG. 5A. FIG. 7 shows a laminated mold 5000 having layers 7010, 7020, 7030, 7040 that define cavity 7060. To achieve this, layers 7010, 7020 are etched anisotropically to have straight sidewalls, while layer 7030 is thicker than the other layers and is etched isotropically to form the complex shaped cross-section shown.

Cross-sectional Surface Condition of Layer

Figure 8:
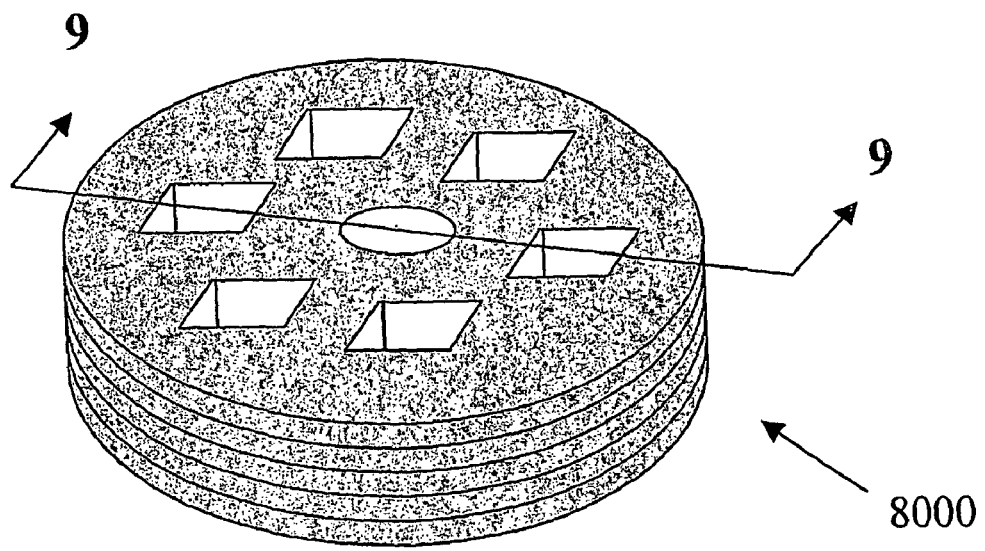
FIG. 8 is a perspective view of an exemplary laminated mold.
Figure 9:
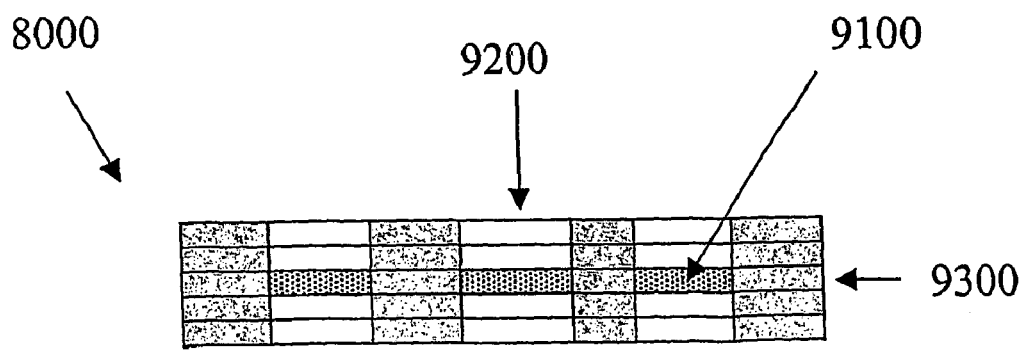
FIG. 9 is a cross-section of an exemplary mold of the present invention taken along lines 9-9 of FIG. 8.

Another design parameter when creating advanced three-dimensional structures can be the cross-sectional surface condition of the layers used to create a laminated mold. As is the case with sidewall shape, surface condition can be used to provide additional function to a structure or a particular region of the structure. FIG. 8 is a perspective view of a generic laminated mold 8000. FIG. 9 is a cross-section of mold 8000 taken at lines 9-9 of FIG. 8. Any sidewall surface, top or bottom surface can be created with one or more specific finish conditions on all layers or on selected layers, such as for example, forming a relatively rough surface on at least a portion of a sidewall 9100 of certain through-features 9200 of layer 9300. As another example, chemical and/or ion etching can be used to produce very smooth, polished surfaces through the use of selected materials and/or processing techniques. Similarly, these etching methods can also be manipulated to produce very rough surfaces.

Secondary techniques, such as electroplating and/or passive chemical treatments can also be applied to micromachined surfaces (such as a layer of the mold) to alter the finish. Certain secondary techniques (for example, lapping or super-finishing) can also be applied to non-micromachined surfaces, such as the top or bottom surfaces of a layer. In any event, using standard profile measuring techniques, described as "roughness average" ($R_a$) or "arithmetic average" (AA), the following approximate ranges for surface finish (or surface conditions) are attainable using micromachining and/or one or more secondary techniques according to certain embodiments of the present invention (units in microns):

50 to any of: 25, 12.5, 6.3, 3.2, 1.6, 0.80, 0.40, 0.20, 0.10, 0.050, 0.025,
25 to any of: 12.5, 6.3, 3.2, 1.6, 0.80, 0.40, 0.20, 0.10, 0.050, 0.025,
12.5 to any of: 6.3, 3.2, 1.6, 0.80, 0.40, 0.20, 0.10, 0.050, 0.025,
6.3 to any of: 3.2, 1.6, 0.80, 0.40, 0.20, 0.10, 0.050, 0.025,
3.2 to any of: 1.6, 0.80, 0.40, 0.20, 0.10, 0.050, 0.025,
1.6 to any of: 0.80, 0.40, 0.20, 0.10, 0.050, 0.025,
0.80 to any of: 0.40, 0.20, 0.10, 0.050, 0.025,
0.40 to any of: 0.20, 0.10, 0.050, 0.025,
0.20 to any of: 0.10, 0.050, 0.025,
0.10 to any of: 0.050, 0.025,
0.050 to any of: 0.025, etc.

Additional Layer Features

Certain exemplary embodiments of the present invention can include layer features that can be created through the use of lithographic etching and/or deposition.

Figure 10A:
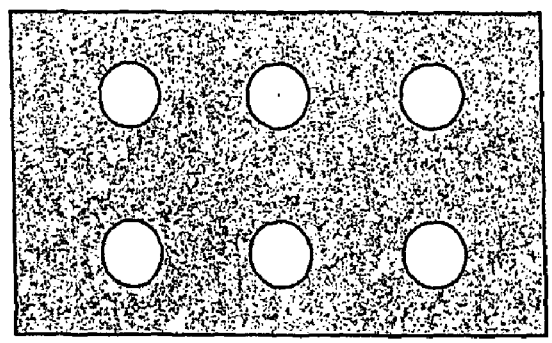
FIG. 10A is a top view an exemplary layer of the present invention having a redundant array of shapes.
Figure 10B:
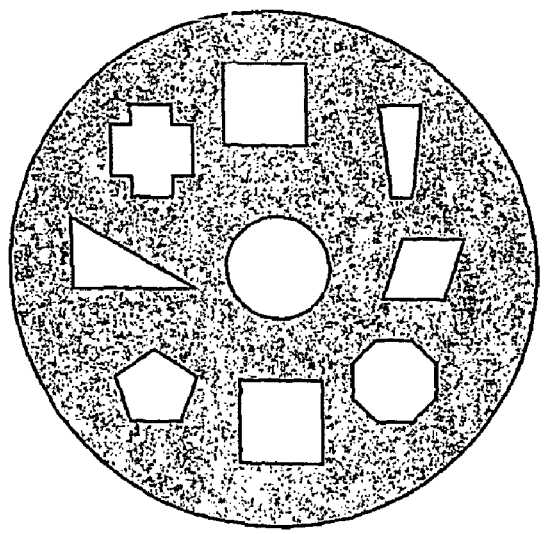
FIG. 10B is a top view of an exemplary layer of the present invention having a non-redundant collection of shapes.

These embodiments can include the size, shape, and/or positional orientation of features relative to the X- and/or Y-axes of a layer and/or their relationship to features on neighboring layers along the Z-axis of the assembled laminated mold. These parameters can define certain geometric aspects of the structure. For example, FIG. 10A is a top view of a layer 10010 having a pattern of repeating features (a redundant array of shapes), and FIG. 10B is a top view of a layer 10020 having a variety of differently shaped features (a non-redundant collection of shapes). Although not shown, a layer can have both redundant and non-redundant features. The terms "redundant" and/or "non-redundant" can refer to either positive or negative features.

Thus, these parameters also can define the shapes and/or spatial forms of features, the number of features in a given area, secondary structures and/or spaces incorporated on or around a feature, and/or the spaces between features. The control of spacing between features can provide additional functionality and, for instance, allow integration of devices with micro-electronics. For example, conductive micro features could be arrayed (redundantly or non-redundantly) to align accurately with application specific integrated circuits (ASIC) to control features. Also, features could be arrayed for applications where non-linear spacing between features could enhance device functionality. For example, filtration elements could be arrayed in such a way as to match the flow and pressure profile of a fluid passing over or through a filtration media The spacing of the filtration elements could be arrayed to compensate for the non-linear movement of the fluid.

Cavity Definition Using Lithography

A cavity formed in accordance with certain exemplary embodiments of the present invention can assume a shape and/or spatial form that includes one or more predetermined "protruding undercuts". Imaginarily rotating the X-Y plane about its origin to any particular fixed orientation, a cavity is defined as having a "protruding undercut" when a first section of the cavity taken perpendicular to the Z-axis (i.e., parallel to the X-Y plane) has a predetermined dimension in the X- and/or Y-direction greater than the corresponding dimension in the X- and/or Y-direction of a second section of the cavity taken perpendicular to the Z-axis, the second section further along in the direction of eventual demolding of a cast part relative to the mold (assuming the demolding operation involves pulling the cast part free from the mold). That is, the X-dimension of the first section is intentionally greater than the X-dimension of the second section by a predetermined amount, or the Y-dimension of the first section is intentionally greater than the Y-dimension of the second section by a pre-determined amount, or both. In still other words, for the purposes of this patent application, the term protruding undercut has a directional component to its definition.

Figure 11:
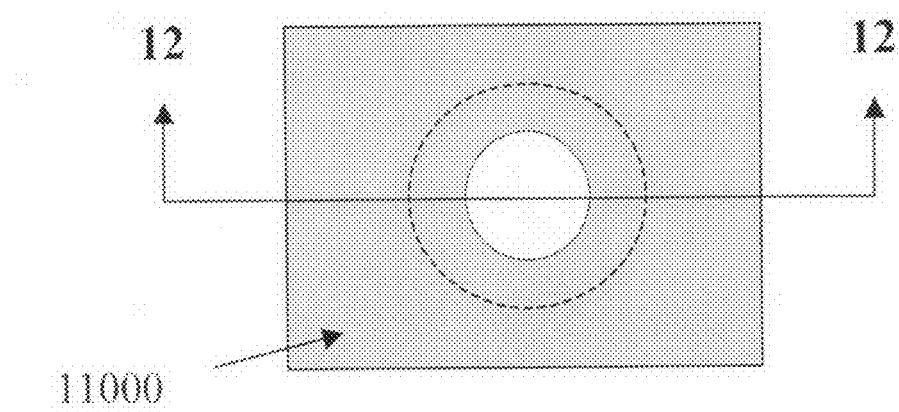
FIG. 11 is a top view of an exemplary stacked lamination mold of the present invention.
Figure 12:
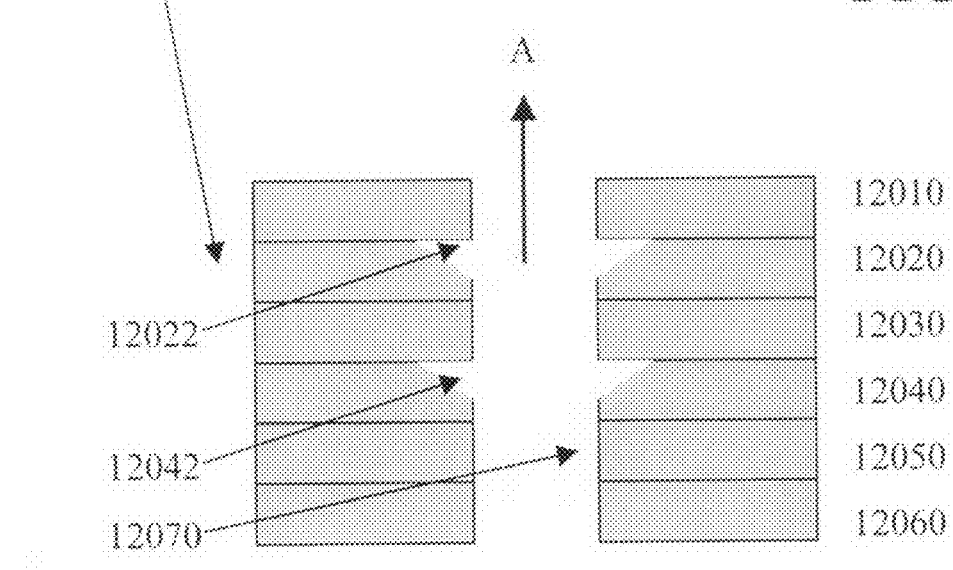
FIG. 12 is a cross-sectional view of an exemplary mold of the present invention taken at section lines 12-12 of FIG. 11.
Figure 13:
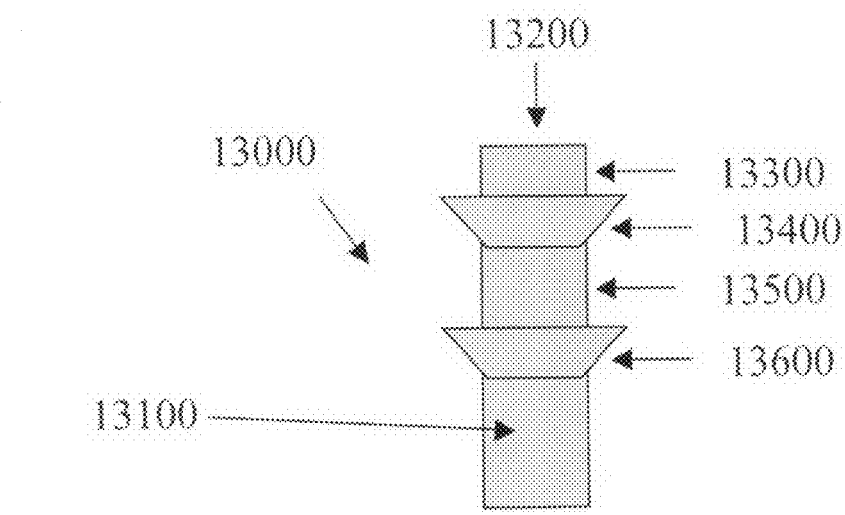
FIG. 13 is a side view of an exemplary cast part of the present invention formed using the exemplary mold of FIG. 11.

FIG. 11 is a top view of an exemplary stacked laminated mold 11000. FIG. 12 is a cross-sectional view of a mold 11000 taken at section lines 12-12 of FIG. 11, and showing the layers 12010-12060 of mold 11000 that cooperatively define a cavity having protruding undercuts 12022 and 12042. Direction A is the relative direction in which a part cast using mold 11000 will be demolded, and/or pulled away, from mold 11000. FIG. 12 also shows that certain layers 12020, 12040 of mold 11000 have been formed by controlled depth etching. As shown in FIG. 12, mold 11000 defines an internal mold surface 12070, which is defined in part by protruding undercuts 12022 and 12042. FIG. 13 is a side view of a cast part 13000 formed using mold 11000. As shown in FIG. 13, cast part 13000 defines an external part periphery or surface 13100, which is defined in part by 3-dimensional micro-features 13400 and 13600 that substantially spatially invertedly replicate protruding undercuts 12022 and 12042.

To make layers for certain embodiments of a laminated mold of the present invention, such as layers 2010 of FIG. 2, a photo-sensitive resist material coating (not shown) can be applied to one or more of the major surfaces (i.e., either of the relatively large planar "top" or "bottom" surfaces) of a micro-machining blank. After the blank has been provided with a photo-resist material coating on its surfaces, "mask tools" or "negatives" or "negative masks", containing a negative image of the desired pattern of openings and registration features to be etched in the blank, can be applied in alignment with each other and in intimate contact with the surfaces of the blank (photo-resist materials are also available for positive patterns). The mask tools or negatives can be made from glass, which has a relatively low thermal expansion coefficient. Materials other than glass can be used provided that such materials transmit radiation such as ultraviolet light and have a reasonably low coefficient of thermal expansion, or are utilized in a carefully thermally-controlled environment. The mask tools can be configured to provide an opening of any desired shape and further configured to provide substantially any desired pattern of openings.

The resulting sandwich of two negative masks aligned in registration and flanking both surfaces of the blank then can be exposed to radiation, typically in the form of ultraviolet light projected on both surfaces through the negative masks, to expose the photo-resist coatings to the radiation. Typically, the photo-resist that is exposed to the ultraviolet light is sensitized while the photo-resist that is not exposed is not sensitized because the light is blocked by each negative masks' features. The negative masks then can be removed and a developer solution can be applied to the surfaces of the blank to develop the exposed (sensitized) photo-resist material.

Once the photo-resist is developed, the blanks can be micro-machined using one or more of the techniques described herein. For example, when using photo-chemical-machining, an etching solution can react with and remove the layer material not covered by the photo-resist to form the precision openings in the layer. Once etching or machining is complete, the remaining unsensitized photo-resist can be removed using a chemical stripping solution.

Sub-cavities on Layers

Figure 14:
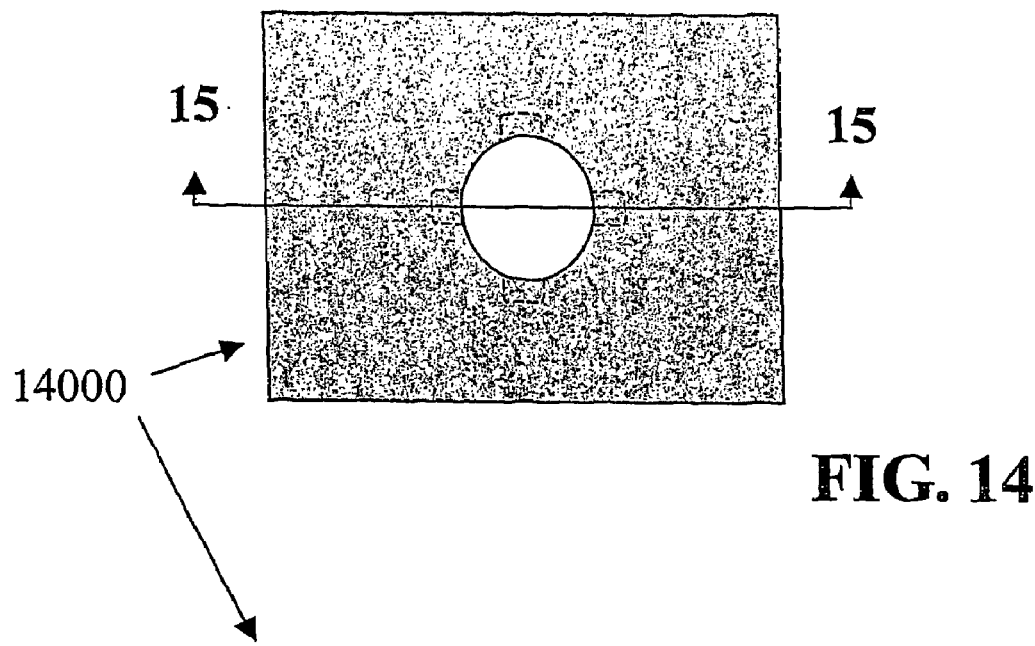
FIG. 14 is a top view of an exemplary laminated mold of the present invention.
Figure 15:
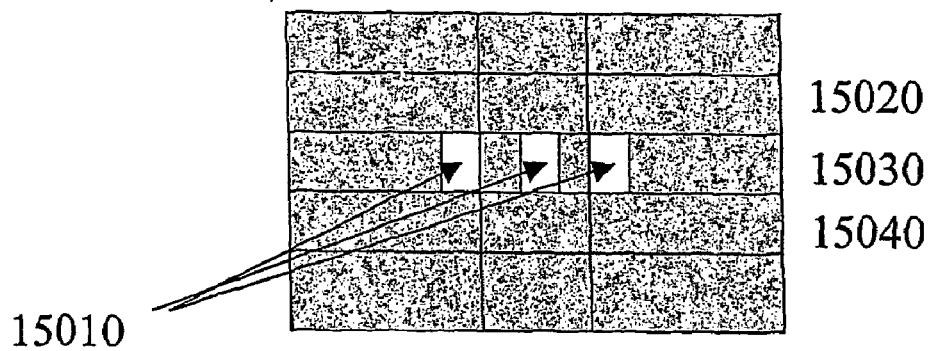
FIG. 15 is a cross-sectional view of an exemplary mold of the present invention taken at section lines 15-15 of FIG. 14.
Figure 16:
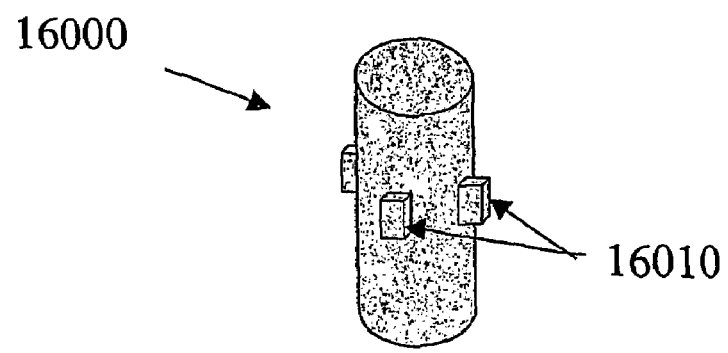
FIG. 16 is a perspective view of an exemplary cast part of the present invention formed using the exemplary mold of FIG. 14.

Cavities can include sub-cavities, which can be engineered and incorporated into the molding and casting scheme using several methods. FIG. 14 is a top view of a laminated mold 14000. FIG. 15 is a cross-sectional view of mold 14000 taken at section lines 15-15 of FIG. 14, and showing the sub-cavities 15010 within layer 15030 of mold 14000. Note that because layer 15030 is sandwiched between layers 15020 and 15040, sub-cavities 15010 can be considered "sandwiched", because sub-cavities are at least partially bounded by a ceiling layer (e.g., 15020) and a floor layer (e.g., 15040). Note that, although not shown, a sub-cavity can extend to one or more outer edges of its layer, thereby forming, for example, a sandwiched channel, vent, sprew, etc. FIG. 16 is a perspective view of cast part 16000 formed using mold 14000, and having protrusions 16010 that reflectively (invertedly) replicate sandwiched sub-cavities 15010.

Because cast part can very accurately reflect the geometries of sub-cavities, such sub-cavities can be used to produce secondary features that can be incorporated with a desired structure. Examples of secondary features include fluid channels passing through or between features, protrusions such as fixation members (similar to Velcro-type hooks), reservoirs, and/or abrasive surfaces. Moreover, a secondary feature can have a wall which can have predetermined surface finish, as described herein.

There are a number of methods for producing sub-cavities in a laminated mold. For example, in the field of photo-chemical-machining, the practice of partially etching features to a specified depth is commonly referred to as "controlled depth etching" or CDE. CDE features can be incorporated around the periphery of an etched feature, such as a through-diameter. Because the CDE feature is partially etched on, for example, the top surface of the layer, it can become a closed cavity when an additional layer is placed on top.

Another method could be to fully etch the sub-cavity feature through the thickness of the layer. A cavity then can be created when the etched-through feature is sandwiched between layers without the features, such as is shown in FIG. 15.

Combinations of micro-machining techniques can be used to create sub-cavities. For example, photo-chemical-machining (PCM) can be used to create the etched-through feature in the layer, while ion etching could be applied as a secondary process to produce the sub-cavities. By combined etching techniques, the sub-cavities can be etched with much finer detail than that of PCM.

Micro-Structures, Features, and Arrays on Non-Planar Surfaces

Certain exemplary embodiments of the present invention can allow the production of complex three-dimensional micro-devices on contoured surfaces through the use of a flexible cavity mold insert.

One activity of such a process can be the creation of a planar laminated mold (stack lamination), which can define the surface or 3-dimensional structures. A second mold (derived mold) can be produced from the lamination using a flexible molding material such as silicone RTV. The derived mold can be produced having a thin backing or membrane layer, which can act as a substrate for the 3-dimensional surface or features. The membrane then can be mechanically attached to the contoured surface of a mold insert, which can define the casting's final shape with the incorporated 3-dimensional features or surface.

Figure 17:
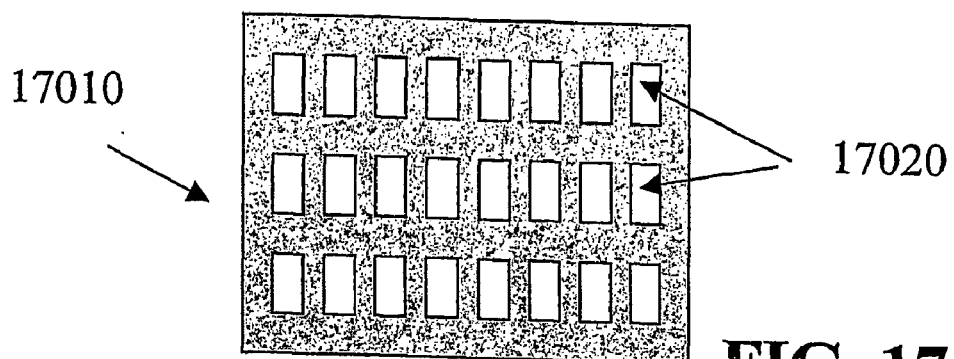
FIG. 17 is a top view of an exemplary planar laminated mold of the present invention having an array of openings.
Figure 18:
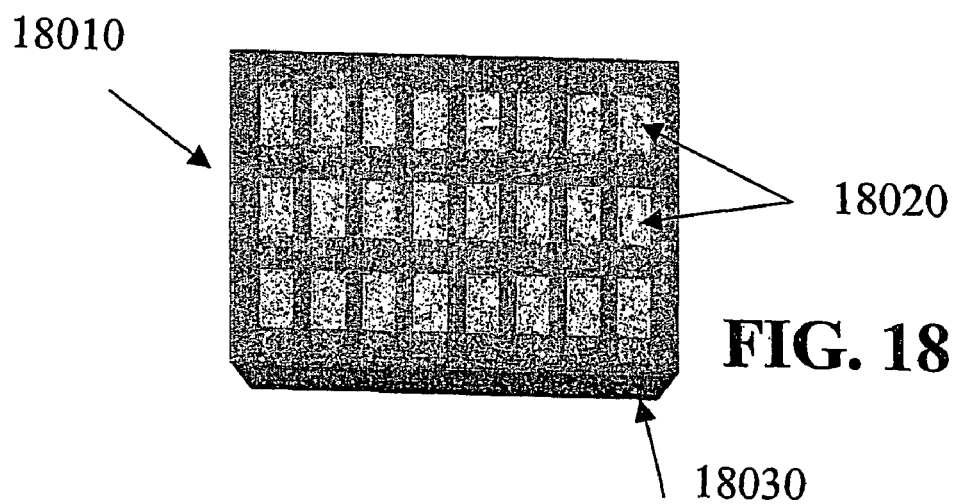
FIG. 18 is a top view of an exemplary flexible casting or mold insert of the present invention molded using the laminated mold of FIG. 17.

As an example, FIG. 17 is a top view of a planar laminated mold 17010 having an array of openings 17020. FIG. 18 is a top view of a flexible casting or mold insert 18010 molded using laminated mold 17010. Flexible mold insert 18010 has an array of appendages 18020 corresponding to the array of openings 17020, and a backing layer 18030 of a controlled predetermined thickness.

Figure 19:
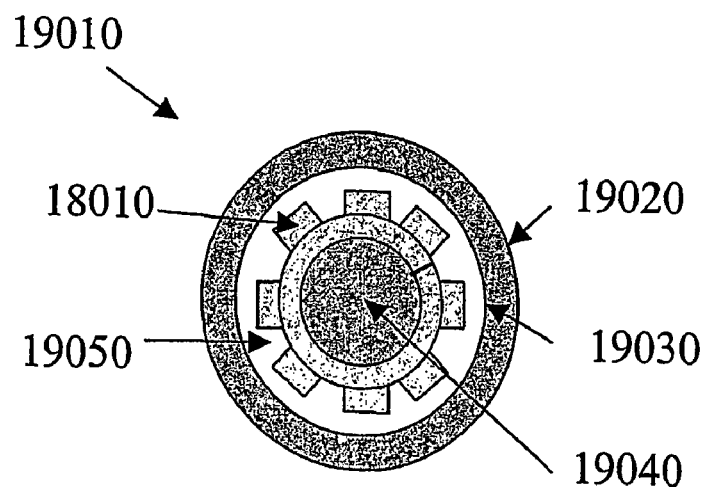
FIG. 19 is a top view of an exemplary mold fixture of the present invention

FIG. 19 is a top view of a mold fixture 19010 having an outer diameter 19020 and an inner diameter 19030. Placed around a cylinder or mandrel 19040 within mold fixture 19010 is flexible mold insert 18010, defining a pour region 19050.

Upon filling pour region 19050, a casting is formed that defines a cylindrical tube having a pattern of cavities accessible from its inner diameter and corresponding to and formed by the array of appendages 18020 of flexible mold insert 18010.

Figure 20:
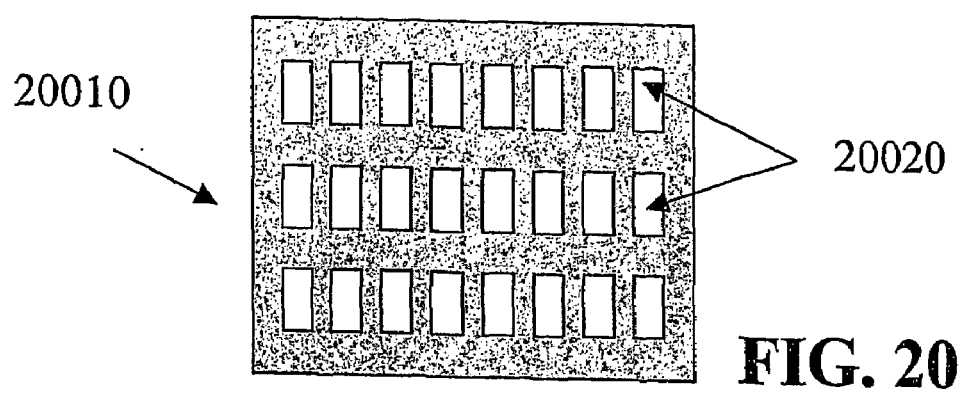
FIG. 20 is a top view of an exemplary planar laminated mold of the present invention.
Figure 21:
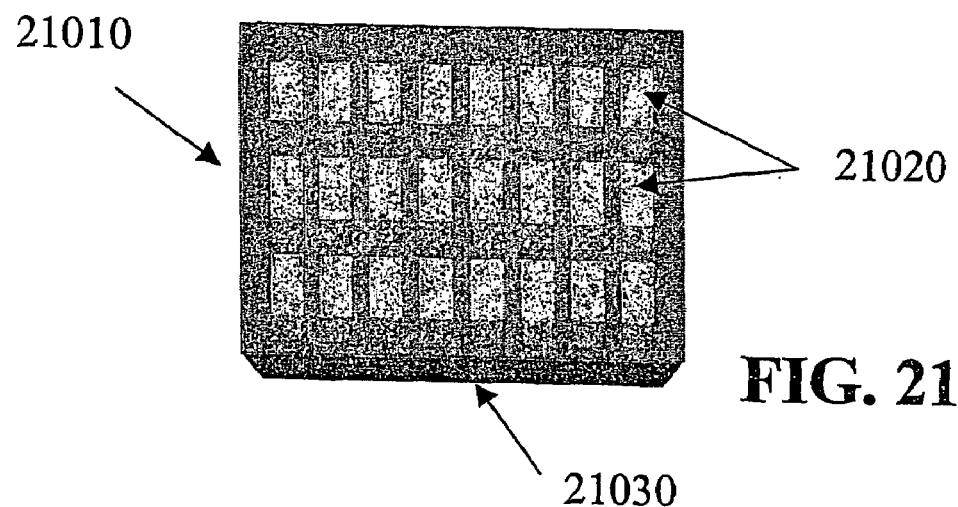
FIG. 21 is a top view of an exemplary flexible casting or mold insert of the present invention molded using the laminated mold of FIG. 20.

As another example, FIG. 20 is a top view of a planar laminated mold 20010 having an array of openings 20020. FIG. 21 is a top view of a flexible casting or mold insert 21010 molded using laminated mold 20010. Flexible mold insert 21010 has an array of appendages 21020 corresponding to the array of openings 20020, and a backing layer 21030 of a controlled predetermined thickness.

Figure 22:
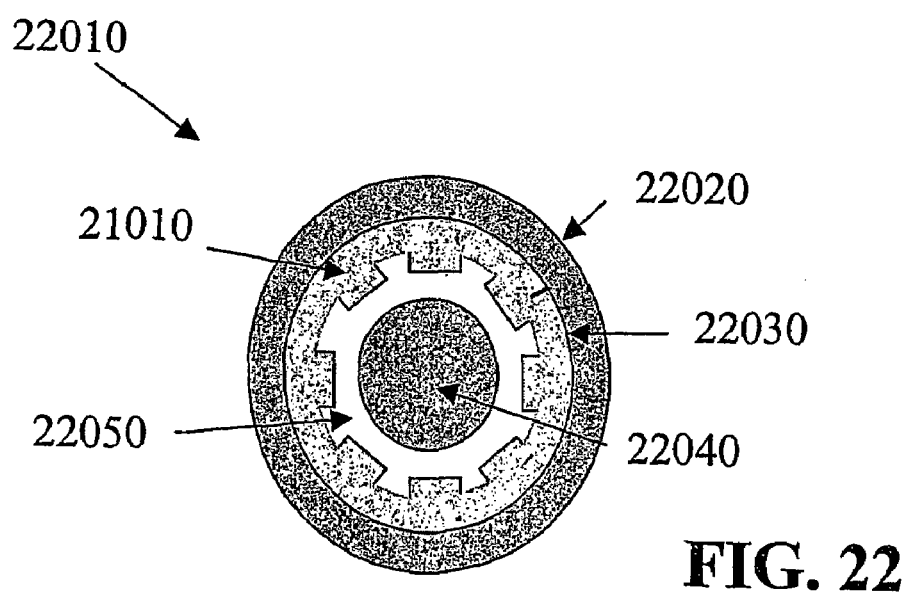
FIG. 22 is a top view of an exemplary mold fixture of the present invention

FIG. 22 is a top view of a mold fixture 22010 having an outer diameter 22020 and an inner diameter 22030. Placed around the inside diameter 22030 within mold fixture 22010 is flexible mold insert 21010, defining a pour region 22050.

Upon filling pour region 22050, a casting is formed that defines a cylindrical tube having a pattern of cavities accessible from its outer diameter and corresponding to and formed by the array of appendages 21020 of flexible mold insert 21010.

Through these and related approaches, the 3-dimensional structure or surface can be built-up at the planar stage, and can be compensated for any distortions caused by forming the membrane to the contoured surface. The fabrication of the laminated mold can use specific or combined micro-machining techniques for producing the layers that define the aspect-ratio and 3-dimensional geometry. Micro-surfaces and/or structures can be transferred to many contours and/or shapes. For example, micro-patterns can be transferred to the inside and/or outside diameter of cylinders or tubes. Specific examples demonstrating the capabilities of this method are provided later in this document.

Cavity Inserts

The term mold insert is used herein to describe a micromachined pattern that is used for molding and/or fabrication of a cast micro-device, part, and/or item. The laminated or derived mold described in this document also can be considered a mold insert. Cavity inserts are described here as a subset of a mold insert. Cavity inserts are objects and/or assemblies that can be placed within a cavity section of a mold but that do not take up the entire cavity space, and that provide further features to a 3-dimensional mold.

Figure 23:
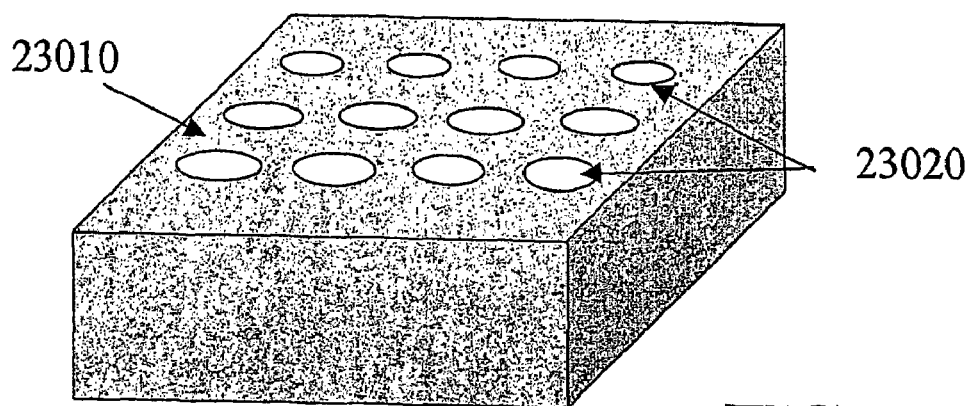
FIG. 23 is a perspective view of an exemplary laminated mold of the present invention.
Figure 24:
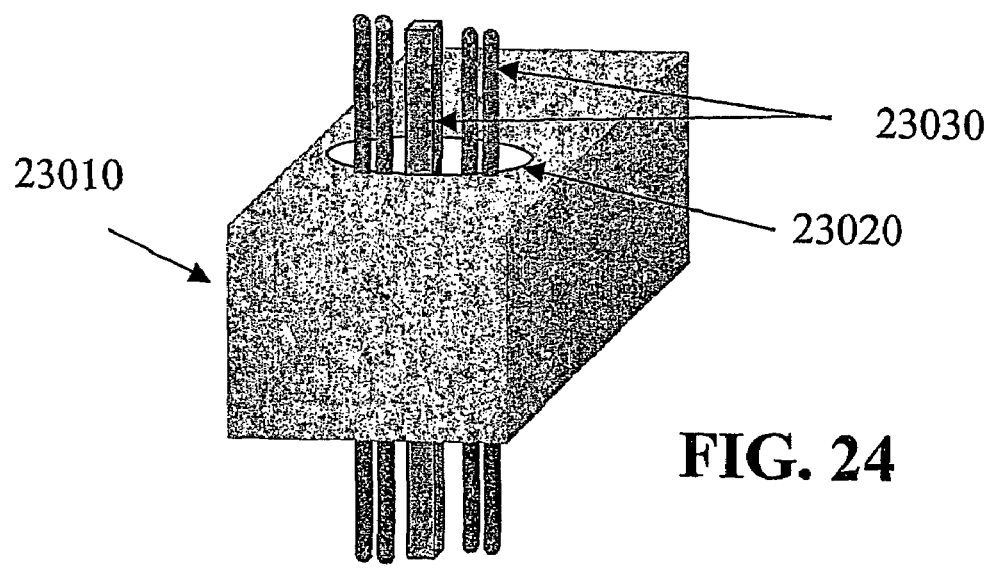
FIG. 24 is a close-up perspective view of an exemplary single cylindrical cavity of an exemplary mold of the present invention.
Figure 25:
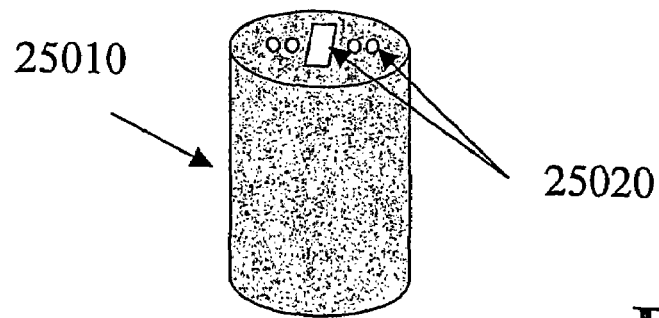
FIG. 25 is a perspective view of an exemplary cast part of the present invention.

As an example, FIG. 23 is a perspective view of a laminated mold 23010 having an array of cylindrical cavities 23020, each extending from top to bottom of mold 23010. FIG. 24 is a close-up perspective view of a single cylindrical cavity 23020 of mold 23010. Suspended and extending within cavity 23020 are a number of cavity inserts 23030. FIG. 25 is a perspective view of a cast part 25010 having numerous cavities 25020 formed by cavity inserts 23030.

A cavity insert can also be produced using certain embodiments of the present invention. This is further explained later in the section on non-planar molds. An insert can be a portion of a mold in the sense that the insert will be removed from the cast product to leave a space having a predetermined shape within the product. An insert alternatively can become part of a final molded product. For instance, if it is desirable to have a composite end product, then a process can be engineered to leave an insert in place in the final molded product.

As an example of a cavity insert, a 3-dimensional mold insert can be produced using one or more embodiments of the present invention, the insert having an array of cavities that are through-diameters. The cast part derived from this mold can reverse the cavities of the mold as solid diameters having the shape, size and height defined by the mold. To further enhance functionality, cavity inserts can be added to the mold before the final casting is produced. In this case, the cavity insert can be a wire formed in the shape of a spring. The spring can have the physical dimensions required to fit within a cavity opening of the mold, and can be held in position with a secondary fixture scheme. The spring-shaped cavity insert can be removed from the cast part after the final casting process is completed. Thus, the cavity section of the mold can define the solid shape of the casting while the cavity insert can form a channel through the solid body in the shape and width of the insert (the spring). The cavity can serve as, for example, a reservoir and/or a fluid flow restrictor.

The examples given above demonstrate the basic principle of a cavity insert. Additional design and fabrication advances can be realized by using this method to create cavity inserts. For example, photo-chemical-machining can be used to create a mold that has larger cavity openings, while reactive-ion-etching can be used to create finer features on a cavity insert.

Fabricating the Laminated Mold

Certain exemplary embodiments of the present invention can involve the fabrication of a laminated mold which is used directly and/or as an intermediate mold in one or more subsequent casting and/or molding processes.

Figure 26:
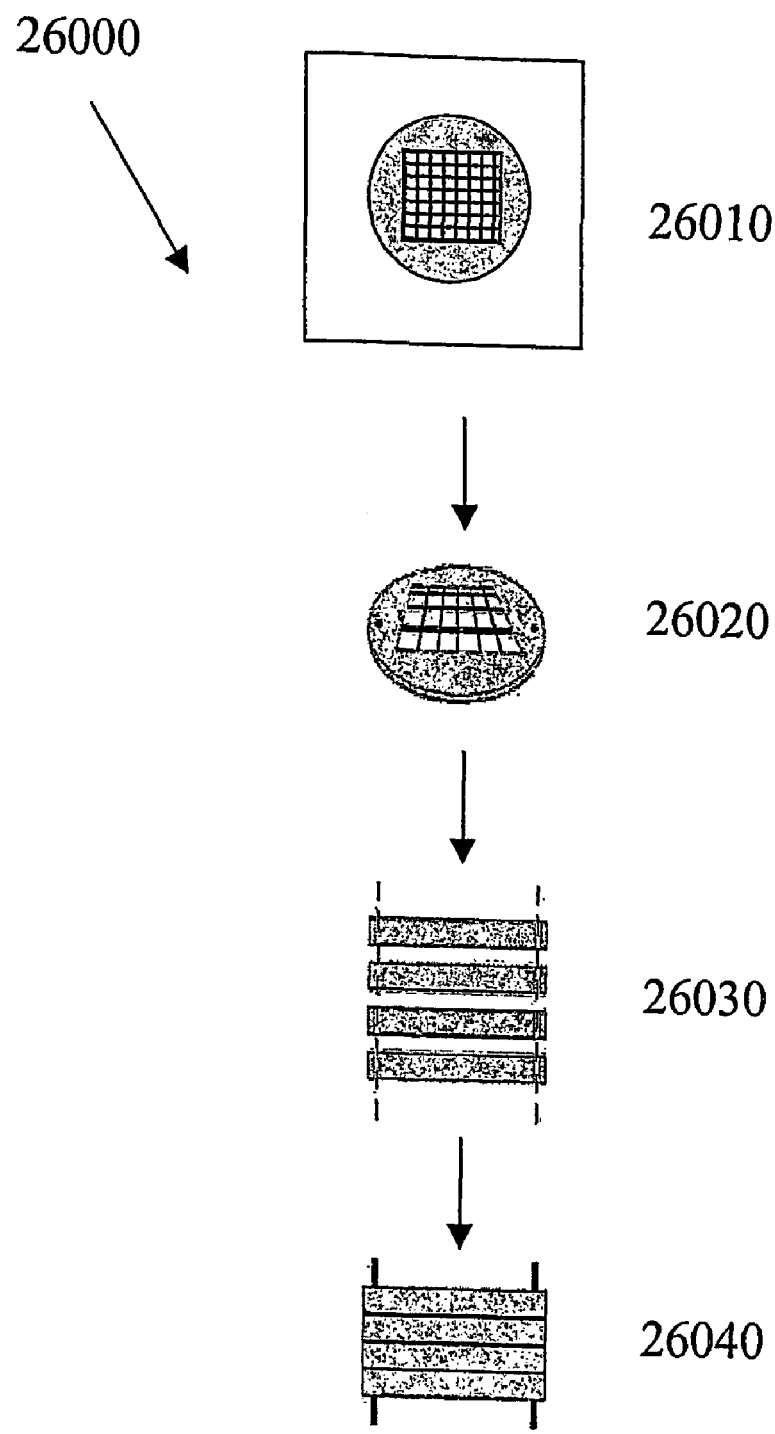
FIG. 26 is a flowchart of an exemplary method of the present invention.

FIG. 26 is a block diagram illustrating various devices formed during an exemplary method 26000 for fabricating a laminated mold having micro-machined layers that can be patterned and/or etched, and stacked to create a 3-dimensional mold. The laminated mold can be produced as a negative or positive replication of the desired finished casting. For the purpose of creating a laminated mold, any of three elements can be implemented:

1) creating a lithographic mask 26010 defining the features of each unique layer, 2) using lithographic micro-machining techniques and/or micro-machining techniques to produce patterned layers 26020, and/or
3) aligning, stacking, and/or laminating the patterned layers into a stack 26030 in order to achieve the desired 3-dimensional cavity shape, aspect ratios, and/or mold parameters desired for a laminated mold 26040.

Lithographic Techniques

Using lithography as a basis for layer fabrication, parts and/or features can be designed as diameters, squares, rectangles, hexagons, and/or any other shape and/or combination of shapes. The combinations of any number of shapes can result in non-redundant design arrays (i.e. patterns in which not all shapes, sizes, and/or spacings are identical, as shown in FIG. 10). Lithographic features can represent solid or through aspects of the final part. Such feature designs can be useful for fabricating micro-structures, surfaces, and/or any other structure that can employ a redundant and/or non-redundant design for certain micro-structural aspects. Large area, dense arrays can be produced through the lithographic process, thereby enabling creation of devices with sub-features or the production of multiple devices in a batch format.

Lithography can also allow the creation of very accurate feature tolerances since those features can be derived from a potentially high-resolution photographic mask.

The tolerance accuracy can include line-width resolution and/or positional accuracy of the plotted features over the desired area. In certain embodiments, such tolerance accuracy can enable micro-scale fabrication and/or accurate integration of created micro-mechanical devices with microelectronics.

Photographic masks can assist with achieving high accuracy when chemical or ion-etched, or deposition-processed layers are being used to form a laminated mold through stack lamination. Because dimensional changes can occur during the final casting process in a mold, compensation factors can be engineered at the photo-mask stage, which can be transferred into the mold design and fabrication. These compensation factors can help achieve needed accuracy and predictability throughout the molding and casting process.

Photographic masks can have a wide range of potential feature sizes and positional accuracies. For example, when using an IGI Maskwrite 800 photoplotter, an active plotting area of 22.8×31.5 inches, minimum feature size of 5 microns, and positional accuracy of +−1 micron within a 15×15 inch area is possible. Using higher resolution lithographic systems for mask generation, such as those employed for electron beam lithography, feature sizes as small as 0.25 microns are achievable, with positional tolerances similar to the Maskwrite plotter, within an area of 6×6 inches.

Layer Machining and Material Options

Another aspect to fabricating the laminated mold can be the particular technique or techniques used to machine or mill-out the features or patterns from the layer material. In certain embodiments, combining lithographic imaging and micro-machining techniques can improve the design and fabrication of high-aspect-ratio, 3-dimensional structures. Some of the micro machining techniques that can be used to fabricate layers for a laminated mold include photo-etching, laser machining, reactive ion etching, electroplating, vapor deposition, bulk micro-machining, surface micro-machining, and/or conventional machining.

In certain exemplary embodiments, a laminated mold need only embody the mechanical features (e.g., size, shape, thickness, etc.) of the final casting. That is, it does not have to embody the specific functional properties (i.e. density, conductivity) that are desired to fulfill the application of the final casting. This means that any suitable techniques or materials can be used to produce the layers of the mold.

Thus, there can be a wide variety of material and fabrication options, which can allow for a wide variety of engineered features of a layer, laminated mold, and/or derived mold. For instance, although photo-chemical machining can be limited to metallic foils, by using laser machining or reactive ion etching, the choice of materials can become greatly expanded. With regard to laser machining, Resonetics, Inc. of Nashua, N.H. commercially provides laser machining services and systems. For laser machining, a very wide range of materials can be processed using UV and infra-red laser sources. These materials include ceramics, metals, plastics, polymers, and/or inorganics. Laser micro-machining processes also can extend the limits of chemical machining with regards to feature size and/or accuracy. With little or no restriction on feature geometry, sizes on the order of 2 microns can be achievable using laser machining.

When a wide variety of materials are available for making the laminated mold, process-compatibility issues can be resolved when choosing the material from which to create the mold. An example of this would be to match the thermal properties of casting materials with those of the laminated mold, in instances where elevated temperatures are needed in the casting or molding process. Also the de-molding properties of the mold and/or casting material can be relevant to the survival of the mold. This, for example, might lead one to laser-machine the layers from a material such as Teflon, instead of a metal. The laser machining process could be compatible with the Teflon and the Teflon could have greater de-molding capabilities than a metallic stack lamination.

In certain exemplary embodiments of the present invention, only a single laminated stack is needed to produce molds or castings. Also, in certain exemplary embodiments of the present invention, molds and/or castings can be produced without the need for a clean-room processing environment.

For certain exemplary embodiments of the present invention, the ability to create a single laminated mold and then cast the final parts can allow for using much thinner foils or advanced etching methods for producing the individual layers. Since feature size can be limited by the thickness of each foil, using thinner foils can allow finer features to be etched.

Certain exemplary embodiments of the present invention can combine various micro-machining techniques to create layers that have very specific functional features that can be placed in predetermined locations along the Z-axis of the mold assembly. For example, photo-chemical-machining can be used to provide larger features and high resolution ion-etching for finer features.

Various methods, as described above, can be used to produce layers for a laminated mold. The following examples are given to demonstrate dimensional feature resolution, positional accuracy, and/or feature accuracy of the layers.

Ion etching: when using a Commonwealth Scientific Millitron 8000 etching system, for example, a uniform etch area of 18 inches by 18 inches is achievable. Feature widths from 0.5 microns and above are attainable, depending on the lithographic masks and imaging techniques used. A feature, for example a 5 micron wide slot, etched to a depth of 10 microns can be etched to a tolerance of +−1.25 microns in width, and +−0.1 microns in depth. The positional tolerance of features would be the same as those produced on the lithographic masks.

Photo-chemical-machining: when using an Attotech XL 547 etching system, for example, a uniform etch area of 20 inches by 25 inches is achievable. Etched through-feature widths from 20 microns and above are attainable, with solid features widths of 15 microns and above also being attainable. A feature, for example a 30 micron diameter etched through 25 microns of copper, can be etched to a tolerance of +−2.5 microns or 10% of the foil thickness. The positional tolerance of such features would be the same as those produced on the lithographic masks.

Laser micromachining: when using a PIVOTAL laser micromachining system, for example, a uniform machining area of 3 inches by 3 inches is achievable. Machined through-feature sizes from 5 microns and above are attainable. A feature, for example a 5 micron wide slit machined through 25 microns of stainless steel, can be machined to a tolerance of +−1 micron. Positional tolerance of +−3 microns is achievable over the 3 inch by 3 inch area.

Electro-forming: depending on the size limitations of the photographic masks used for this process, electro-forming over areas as large as 60 inches by 60 inches is attainable. Electro-formed layers having thickness of 2 microns to 100 microns is achievable. A feature, for example a 5 micron wide slit, 15 microns deep, can be formed to a tolerance of +−1 micron. Positional tolerance of features would be the same as those produced on the lithographic masks.

Layer Assembly and Lamination

As described above, in certain exemplary embodiments of the present invention, layers can be designed and produced so that feature shape and placement from layer to layer define the desired geometry along the X-, Y-, and/or Z-axes of a mold. The total number (and thickness) of layers in the assembly can define the overall height and aspect ratio of the feature. A feature can be either the solid shape or the space between given structural components.

What follows are several exemplary methods of bonding the layers together to form the laminated mold. One exemplary method used to bond layers together is a metal-to-metal brazing technique. This technique can provide a durable mold that can survive high volume production casting and/or can provide efficient release properties from the castings. Prior to assembly, the layers can have 0.00003 inches of a eutectic braze alloy deposited on the top and bottom surfaces of the layers, using standard electroplating techniques. An example of a braze material is CuSil™, which is comprised of copper and silver, with the percentage of each being variable for specific applications. CuSil™ can be designed specifically to lower the temperatures needed to flow the alloy during the brazing process.

Figure 27:
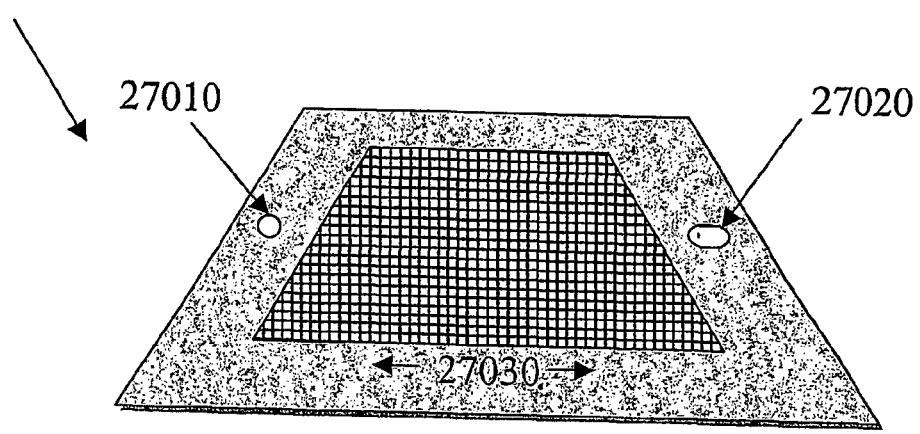
FIG. 27 is a perspective view of a plurality of exemplary layers of the present invention.

One of the potential concerns during the laminating process is to maintain accurate registration of the assembly layers, and/or control the movement of the layers and the bonding fixture when brought to the elevated temperatures needed to flow the braze material. Several methods can be used to achieve this registration and/or control. The first can involve the practice of having two or more alignment features on the layers. FIG. 27 is a perspective view of a plurality of exemplary layers 27000. As illustrated in FIG. 27, one such alignment feature can be a diameter 27010, and the other alignment feature can be an elongated slot 27020. The slot and the diameter can be positioned on each layer one hundred eighty degrees opposed, for example, and can be parallel in orientation with the grain and/or perpendicular to the plane of the layer material.

Figure 28:
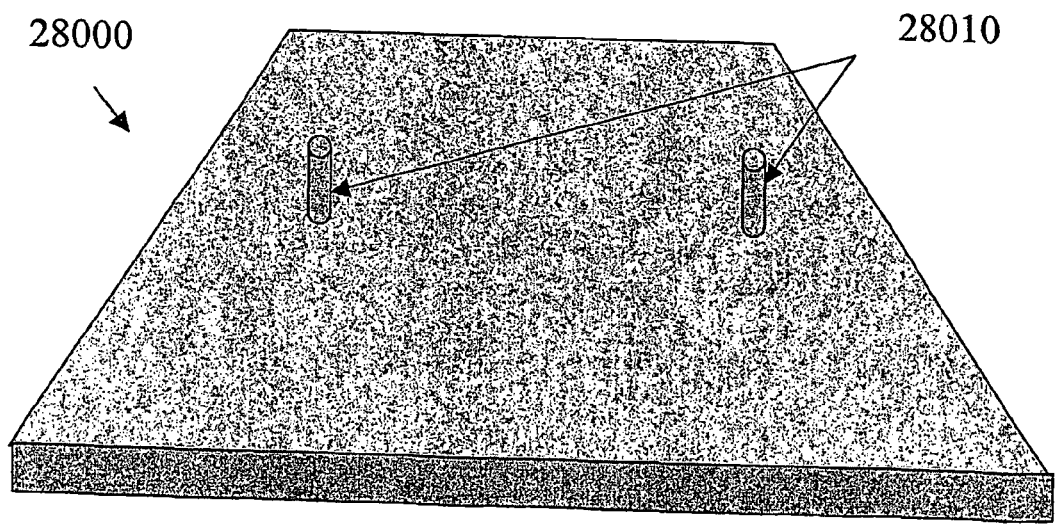
FIG. 28 is a perspective view of an exemplary laminating fixture of the present invention.

FIG. 28 is a perspective view of an exemplary laminating fixture 28000, which can be fabricated from graphite, for example, and can have two graphite diameter pins 28010 that can be fixed to the lamination fixture at the same distance apart as the diameter 27010 and slot 27020 on the etched layers 27000. The layers can be placed over the pins 28010 so that each layer is orientated accurately to the layer below, using the slot and diameter to align each layer. Alternatively, two or more diameters can be provided on the layers 27000, each of which corresponds to a pin of laminating fixture 28000.

During the brazing process, the layered assembly can be heated in a hydrogen atmosphere to a temperature of 825 degrees Celsius, which can cause the CuSil™ braze to flow. As the temperatures elevate, the layers and the fixture material can expand. The slotted alignment feature 27020 can allow the fixture 28000 material to expand or move at a dissimilar rate than the layers, by the presence of the elongated slot on the layer 27000. The slot 27020 can be greater in length than the diameter of pin 28010 in the fixture. The additional length of the slot can be determined by the different coefficient for expansion between the graphite and the assembly layers.

Other methods for maintaining the layer alignment during a heated bonding process can include fabricating the bonding fixture from the same material as the assembly layers, which can thus limit the dissimilar movement of the layers and fixture. The alignment and bonding fixture can also be made so that the alignment pins fit nearly perfectly to alignment features on the layers, but the pins in the fixture are allowed to float while being held perpendicular to the face of the alignment fixture.

In order to minimize positional errors when bonding layers (stacking errors), tolerances on certain features can be controlled. Referring to FIG. 27, the positional accuracy of features 27010 and 27020 can be controlled by the photographic masks used to produce the layers (exemplary tolerances for masks are provided in the section titled "Lithographic Techniques", above). The geometric size and tolerance of features 27010 and 27020 can be governed by the layer thickness and/or micromachining method used to produce them (exemplary tolerances for various micromachining techniques are provided in the section titled "Layer Machining and Material Options", above).

When producing a laminated mold, numerous factors can be an influence on the overall tolerances of the features of the mold and/or the casting. For example, when using a stacking fixture, any of the laminating fixture's surface flatness, the laminating fixture's perpendicularity, and the laminating fixture's parallelism can be an influence. Also, the dimensional tolerance of the alignment feature(s) of a layer and/or the positional tolerance of that feature(s) can be an influence. For example, if an alignment pin, protrusion, or other "male" feature will engage a corresponding hole, indentation, or "female" feature to assist in aligning two or more layers, the dimensional tolerance and/or vocational tolerance of male and/or female feature can be an influence on the overall tolerances.

For example, referring to FIG. 28, bonding fixture 28000 can include alignment pins 28010 fitted into the top surface of fixture 28000. In a particular experiment, through the use of a surface grinding process, followed by a planetary lapping and polishing process, the sides and top surface of bonding fixture 28000 were parallel and perpendicular to a tolerance of +−2 microns, with the top surface finish being optically flat to +− one half the wavelength of visible light (400 to 700 nanometers), or about 200 to 350 nanometers. The positional accuracy of the alignment pins and the machined diameters through fixture 28000 was +−5 microns, and the pins were perpendicular to the surface of the fixture to +−2 microns, measured at a pin height of 2 to 5 millimeters. The surface of the described fixture measured 6×6 inches, and was produced using an SIP 5000 Swiss jig boring milling center. Hardened steel alignment pins, having a diameter of 0.092 inches, were precisely ground to a tolerance of +−1.25 microns using a standard grinding operation.

The process of laminating the layers can include placing the processed layers over the alignment pins until the desired number of layers have been assembled. The assembled layers and fixture then can be placed in a brazing furnace with uniform weight applied to the top of the fixture. The furnace temperature can be raised to a temperature of 825 degrees Celsius, in a hydrogen atmosphere (a vacuum atmosphere has also been shown to work) for 45 minutes. This temperature can be sufficient to allow the braze material to uniformly flow and connect the layers together at all contact points. The fixture then can be cooled in the hydrogen atmosphere for 2 hours and removed for disassembly. The graphite pins can be removed, freeing the bonded structure from the lamination fixture.

The brazed lamination now can be ready for the final process step, which can be to coat the entire assembly with a hard nickel surface. The nickel coating can be applied to the laminated assembly using electroplating techniques, which can deposits 0.0001 inches of nickel. The nickel-plated surface can act as an interface material that can enhance the release and durability properties of the assembled mold.

Another exemplary method that can be used to bond layers can make use of a thermo-cured epoxy rather than metal-to-metal brazing. Prior to assembly, the layers can be coated with an epoxy, MAGNA-TAC® model E645, diluted 22:1 with acetone. The thinned epoxy can be applied to the top and bottom surfaces of the layers using a standard atomizing spray gun. The layers can be spray coated in such a way that the coverage of the epoxy will bond the layers without filling the micro-machined features. A dot coverage of 50% has shown to work. The parameters for dilution and coverage can be provided by the epoxy manufacture, such as the Beacon Chemical Company.

The layers then can be assembled to a bonding fixture using, for example, the same technique described in the braze process. The assembled fixture then can be placed in a heated platen press, such as a Carver model #4122. The assembled layers and fixture can be compressed to 40 pounds per square inch and held at a temperature of 350 degrees F. for 3 hours, and allowed to cool to room temperature under constant pressure. The assembly then can be removed from the fixture using, for example, the same technique used for the brazed assembly.

In certain embodiments, the technique described in the second example can be considerably less expensive and time consuming than that used for the first. Using the epoxy process, savings can be realized due to the cost of the plating and the additional requirement imposed by the hydrogen braze process compared to epoxy stack laminating. The master derived from the first example can provide more efficient de-molding properties and also can survive a greater number of castings than the epoxy bonded mold. The epoxy-bonded mold can demonstrate a cost effective alternative to brazing and can be used for prototyping or when smaller production quantities are required.

Casting and Molding Process

Exemplary embodiments of the present invention can involve the creation of a high-resolution casting mold, having high-aspect-ratio, as well as 3-dimensional features and shapes. A precision stack lamination, comprised of micro-machined layers, can be used as a laminated mold. The laminated mold can be used to produce advanced micro-devices and structures (a.k.a., "micro-electro-mechanical structures" and "MEMS") and/or can be used to create second (or greater) generation derived molds.

The following paragraphs describe the casting process in terms of the materials, fixtures, and/or methods that can be used to produce second-generation molds and final castings.

Mold Duplication and Replication

For certain exemplary embodiments of the present invention, the process options for producing molds and cast parts can be numerable. For example, molds can be made as negative 4010 or positive 4020 replications of the desired cast part as shown in FIG. 4. If the mold is made as a positive, a second-generation mold can be created. If the mold is made as a negative, the final part can be cast directly from the mold.

For certain exemplary embodiments of the present invention, the process used to create the layers for the laminated mold can be a determining factor. For example, some production situations can require a second- (or even third) generation derived version of the laminated mold.

In certain situations, process parameters can be greatly enhanced by combining molding and casting materials having certain predetermined values for physical properties such as durometer, elasticity, etc. For example, if the cast part is extremely rigid, with poor release properties, a second-generation consumable mold can be used to create the final casting. Further specific examples of this practice, and how they relate to 3-dimensional micro-fabrication are described later in this document.

Feature size and positional accuracy for molds and produced parts can be compensated for at the layer production stage of the process. For example, known material properties such as thermal expansion or shrinkage can be accurately accounted for due to, for example, the accuracy levels of the photographic masks and/or laser machining used to produce mold layers. Feature resolution, using various mold making and casting materials, can be accurately replicated for features having a size of 1 micron and greater. Surface finishes have also been reproduced and accurately replicated. For example, layers have been used to form a laminated mold which was used to produce a derived silicone RTV mold. The surface finish of a 0.0015 inch thick stainless steel layer (specified finish as 8-10 micro inches RA max) and a 0.002 inch thick copper layer (specified finish as 8-20 micro inches RA max ) were easily identified on the molded surfaces of the derived RTV mold. The surfaces were observed at 400× magnification using a Nikon MM11 measuring scope. The same surface finishes were also easily identified when cast parts were produced from the derived mold using a casting alloy CERROBASE™. Very smooth surface finishes, such as those found on glass, have also been reproduced in molds and castings.

Materials for Molds and Castings

For certain exemplary embodiments of the present invention, there can be hundreds, if not thousands of material options for mold making and casting. Described below are some potential considerations regarding the selection of mold and casting materials that can meet the requirements of, for instance, 3-dimensional MEMS.

To insure the accuracy and repeatability of certain cast micro-devices, the casting material can have the capability to resolve the fine 3-dimensional feature geometries of the laminated mold. Typical dimensions of MEMS can range from microns to millimeters. Other structures having micro features can have much larger dimensions.

For certain embodiments, the mold's cavity geometry can influence the release properties between the mold and the casting, thereby potentially implicating the flexibility (and/or measured durometer) of the materials used. Other material compatibility issues also can be considered when using a casting process.

Certain exemplary embodiments of a process of the present invention have been developed in order to enable the production of 3-dimensional micro-structures from a wide range of materials, tailored to specific applications. The ability to use various materials for molds and castings can greatly expand the product possibilities using this technique.

One material that has been successfully used for creating castings from a laminated mold is an elastomeric product, referred to generally as RTV silicone rubber, although other materials could also be successful depending on process or product requirements. A wide range of silicone-based materials designed for various casting applications are commercially available through the Dow Corning Corporation of Midland, Mich. For example, the Silastic® brand products have proven successful, possibly because of their resolution capability, release characteristics, flexibility, durability, and/or the fact that they work in a wide range of process temperatures.

Although other types of silicone rubber products could be used, each of the Dow Corning Silastic® brand products that have been used consists of two components; a liquid silicone rubber and a catalyst or curing agent. Of the Dow Corning Silastic® brand products, there are two basic curing types: condensation, and addition cure. The two types can allow for a range of variations in material viscosities and cure times. The three primary products used in the earliest tests are Silastic® J RTV Silicone Rubber, Silastic® M RTV Silicone Rubber, and Silastic® S RTV Silicone Rubber. Product specifications are provided in several of the examples at the end of this document.

The Dow Corning Silastic® products used thus far have similar specifications regarding shrinkage, which increases from nil up to 0.3 percent if the silicone casting is vulcanized. Vulcanization can be accomplished by heating the silicone to a specific elevated temperature (above the casting temperature) for a period of 2 hours. Vulcanizing can be particularly useful when the casting is to be used as a regenerated mold, and will be subjected to multiple castings.

In addition to RTV silicone rubber, urethanes and other materials also have properties that can be desirable for laminated molds, derived molds, and/or castings, depending on the specific requirement. For example, when producing certain 3-dimensional micro-structures with extreme aspect ratios, very fine features, or extreme under-cuts, de-molding can be difficult. In certain situations, the rigidity of the mold also can be relevant, especially in certain cases where mold features have high-aspect ratios. For example, the practice of sacrificing or dissolving laminated second or third generation molds can be used when castings require very rigid molds, and/or where the de-molding of castings becomes impossible.

There are several families of materials that can be used for producing laminated molds, derived molds, and/or final cast devices including, for example:

Acrylics: such as, for example, PMMA acrylic powder, resins, and/or composites, as well as methacrylates such as butyl, lauryl, stearyl, isobutyl, hydroxethyl, hydroxpropyl, glycidyl and/or ethyl, etc.

Plastic polymerics: such as, for example, ABS, acetal, acrylic, alkyd, flourothermoplastic, liquid crystal polymer, styrene acrylonitrile, polybutylene terephthalate, thermoplastic elastomer, polyketone, polypropylene, polyethylene, polystyrene, PVC, polyester, polyurethane, thermoplastic rubber, and/or polyamide, etc.

Thermo-set plastics: such as, for example, phenolic, vinyl ester, urea, and/or amelamine, etc.

Rubber: such as, for example, elastomer, natural rubber, nitrile rubber, silicone rubber, acrylic rubber, neoprene, butyl rubber, flurosilicone, TFE, SBR, and/or styrene butadiene, etc.

Ceramics: such as, for example, silicon carbide, alumina, silicon carbide, zirconium oxide, and/or fused silica, calcium sulfate, luminescent optical ceramics, bio-ceramics, and/or plaster, etc.

Alloys: such as, for example, aluminum, copper, bronze, brass, cadmium, chromium, gold, iron, lead, palladium, silver, sterling, stainless, zinc platinum, titanium, magnesium, anatomy, bismuth, nickel, and/or tin, etc.

Wax: such as, for example, injection wax, and/or plastic injection wax, etc.

There can be many material options within these groups that can be utilized when employing certain embodiments of the present invention. For example, in certain embodiments, metals and metal alloys can be primarily used as structural materials of final devices, but also can add to function. Exemplary functional properties of metals and/or alloys can include conductivity, magnetism, and/or shape memory.

Polymers also can be used as structural and/or functional materials for micro-devices. Exemplary functional properties can include elasticity, optical, bio-compatibility, and/or chemical resistivity, to name a few. Materials having dual (or more) functionality, often referred to as engineered "smart" materials, could be incorporated into a final molded product or a mold. Additional functionality could utilize electrostatic, mechanical, thermal, fluidic, acoustic, magnetic, dynamic, and/or piezo-electric properties. Ceramics materials also can be used for applications where specialty requirements may be needed, such as certain high-temperature environments. Depending on the material that is chosen, there can be many alterative methods to solidify the casting material. The term "solidify" includes, but is not limited to, methods such as curing, vulcanizing, heat-treating, and/or chemically treating, etc.

Mold Fixtures, Planar and Contoured

For certain exemplary embodiments of the present invention, there can be a wide range of engineering options available when designing a casting mold. The casting process and geometry of the final product can determine certain details and features of the mold. Options can be available for filling and/or venting a mold, and/or for releasing the casting from the mold.

Two basic approaches have been used for demonstrating the certain exemplary methods for mold design and fabrication. These approaches can be categorized as using a single-piece open-face mold or a two-part closed mold.

In certain exemplary embodiments of the present invention, each of the mold types can include inserting, aligning, and assembling the laminated mold (or duplicate copy) in a fixture. The fixture can serve several purposes, including bounding and/or defining the area in which to pour the casting material, capturing the casting material during the curing process, allowing the escape of air and/or off-gases while the casting material is degassed, and/or enabling mechanical integration with the casting apparatus.

The fixture can be configured in such a way that all sides surrounding the mold insert are equal and common, in order to, for example, equalize and limit the effects of thermal or mechanical stresses put on the mold during the casting process. The mold fixture also can accommodate the de-molding of the casting.

Certain exemplary embodiments of this method can provide the ability to mold 3-dimensional structures and surfaces on contoured surfaces. The basic technique is described earlier in this document in the design parameter section. One element of the technique can be a flexible mold insert that can be fixed to a contoured surface as shown in FIGS. 19 and 22. The mold insert can be made with a membrane or backing thickness that can allow for integration with various fixture schemes that can define the contoured shape.

For non-planar molds, the contour of the mold fixture can be produced by standard machining methods such as milling, grinding, and/or CNC machining, etc. The flexible mold insert can be attached to the surface of the mold using any of several methods. One such method is to epoxy bond the flexible insert to the fixture using an epoxy that can be applied with a uniform thickness, which can be thin enough to accommodate the mold design. Other parameters that can be considered when choosing the material to fix a membrane to a fixture include durability, material compatibility, and/or temperature compatibility, etc. A detailed description of a non-planar mold is given as an example further on.

Casting and Molding Processes

Various techniques can be used for injecting or filling cavity molds with casting materials, including injection molding, centrifugal casting, and/or vibration filling. An objective in any of these techniques can be to fill the cavity with the casting material in such a way that all of the air is forced out of the mold before the cast material has solidified. The method used for filling the cavity mold can depend on the geometry of the casting, the casting material, and/or the release properties of the mold and/or the cast part.

As has been described earlier, an open face mold, using flexible RTV rubber has been found to work effectively. In certain embodiments, an open face mold can eliminate the need for having carefully designed entrance sprue and venting ports. The open face mold can be configured to create an intermediate structure that can have a controlled backing thickness which can serve any of several purposes: 1) it can be an open cavity section in the casting mold which can serve as an entrance point in which to fill the mold; 2) it can serve as a degassing port for the air evacuation during the vacuum casting process; 3) it can create a backing to which the cast part or parts can be attached and/or which can be grasped to assist in de-molding the casting from the flexible mold.

In casting processes in which the casting material is heated, the mold temperature and the cooling of the casting can be carefully controlled. For example, when casting a lead casting alloy such as CERROBASE, the alloy can be held at a temperature of 285 degrees F., while the mold material can be preheated 25-30 degrees higher (310-315 degrees F.). The molten alloy can be poured and held at or above the melting point until it is placed in the vacuum environment. The mold then can be placed in a vacuum bell jar, and held in an atmosphere of 28 inches of mercury for 3-4 minutes. This can remove any air pockets from the molten metal before the alloy begins to solidify. As soon as the air has been evacuated, the mold can be immediately quenched or submersed in cold water to rapidly cool the molten metal. This can help minimize shrinkage of the cast metal.

In certain exemplary embodiments of the present invention, no vent holes or slots are provided in the mold, and instead, air can be evacuated from the mold prior to injection. In certain exemplary embodiments of the present invention, temperature variation and its effect on the micro-structure can be addressed via enhanced heating and cooling controls in or around the mold. In certain exemplary embodiments of the present invention, heat can be eliminated from the curing process by replacing the molding materials with photo-curing materials.

Some of the methods that can be used for micro-molding and casting include micro-injection molding, powder injection molding, metal injection molding, photo molding, hot embossing, micro-transfer molding, jet molding, pressure casting, vacuum casting, and/or spin casting, etc. Any of these methods can make use of a laminated or derived mold produced using this method.

De-Molding and Finish Machining

A controlled backing thickness can be incorporated into the casting to create an intermediate structure. One purpose of the intermediate can be to create a rigid substrate or backing, that allows the casting to be grasped for removal from the mold without distorting the casting. The thickness of the backing can be inversely related to the geometry of the pattern or features being cast. For example, fine grid patterns can require a thicker backing while coarse patterns can have a thinner backing. The backing can be designed to have a shape and thickness that can be used to efficiently grasp and/or pull the cast part from the mold.

Following de-molding, the intermediate can be machined to remove the backing from the casting. Because the thickness of the backing can be closely controlled, the backing can be removed from the cast structure by using various precision machining processes. These processes can include wire and electrode EDM (electrode discharge machining), surface grinding, lapping, and/or fly cutting etc.

In instances where extremely fine, fragile patterns have been cast, a dissolvable filler or potting material can be poured and cured in the cast structure prior to the removal of the backing from the grid. The filler can be used to stabilize the casting features and eliminate possible damage caused by the machining process. The filler can be removed after machining-off the backing. A machinable wax has been found to be effective for filling, machining, and dissolving from the casting.

In some part designs, de-molding the casting from the mold might not be possible, due to extreme draft angles or extremely fine features. In these cases, the mold can remain intact with the cast part or can be sacrificed by dissolving the mold from casting.

EXAMPLES

A wide range of three-dimensional micro-devices can be fabricated through the use of one or more embodiments of various fabrication processes of the present invention, as demonstrated in some of the following examples.

Example 1

Sub-Millimeter Feedhorn Array

This example demonstrates fabrication of an array of complex 3-dimensional cavity features having high aspect ratio. This example makes use of a second-generation derived mold for producing the final part, which is an array of sub-millimeter feedhorns. A feedhorn is a type of antenna that can be used to transmit or receive electromagnetic signals in the microwave and millimeter-wave portion of the spectrum. At higher frequencies (shorter wavelengths) the dimensions can become very small (millimeters and sub-millimeter) and fabrication can become difficult.

Using certain exemplary embodiments of the present invention, a single horn, an array of hundreds or thousands of identical horns, and/or an array of hundreds or thousands of different horns can be fabricated.

Figure 29:
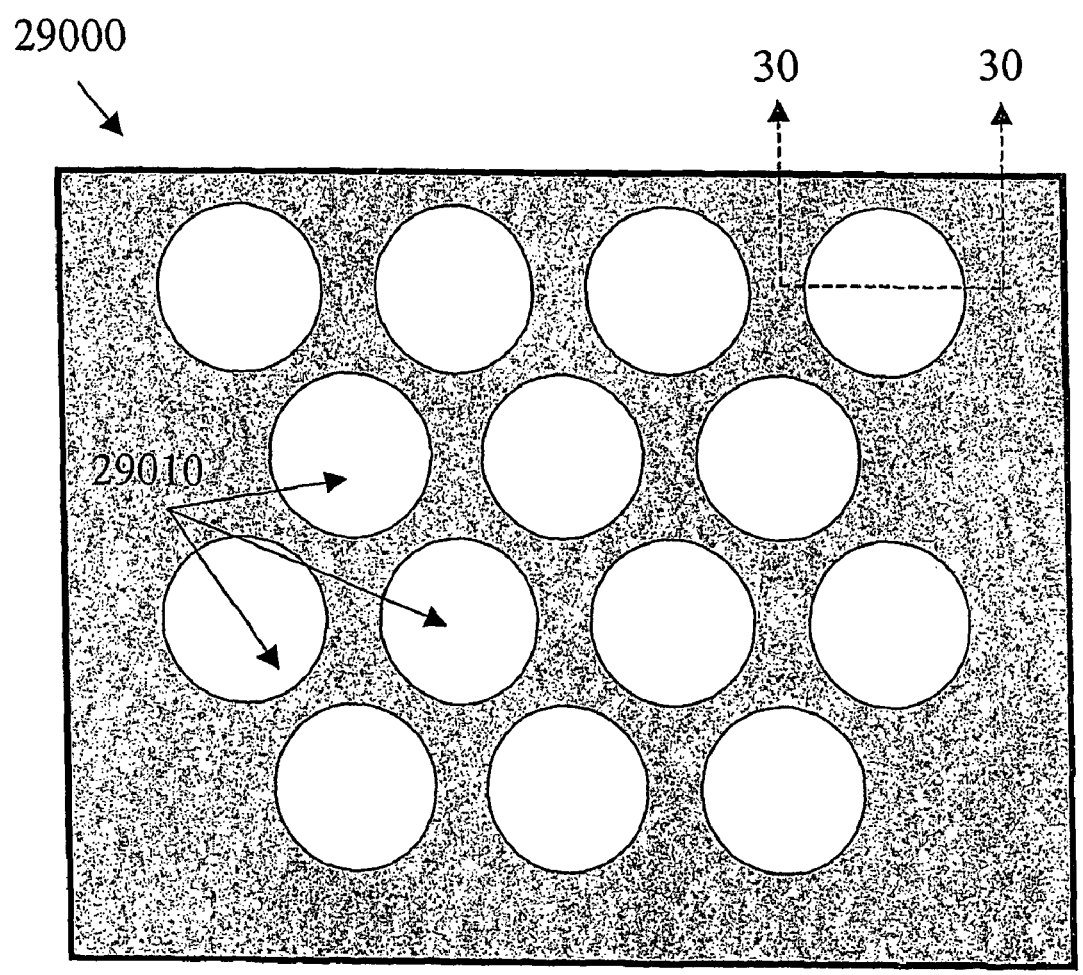
FIG. 29 is a top view of stack lamination mold of the present invention that defines an array of cavities.
Figure 30:
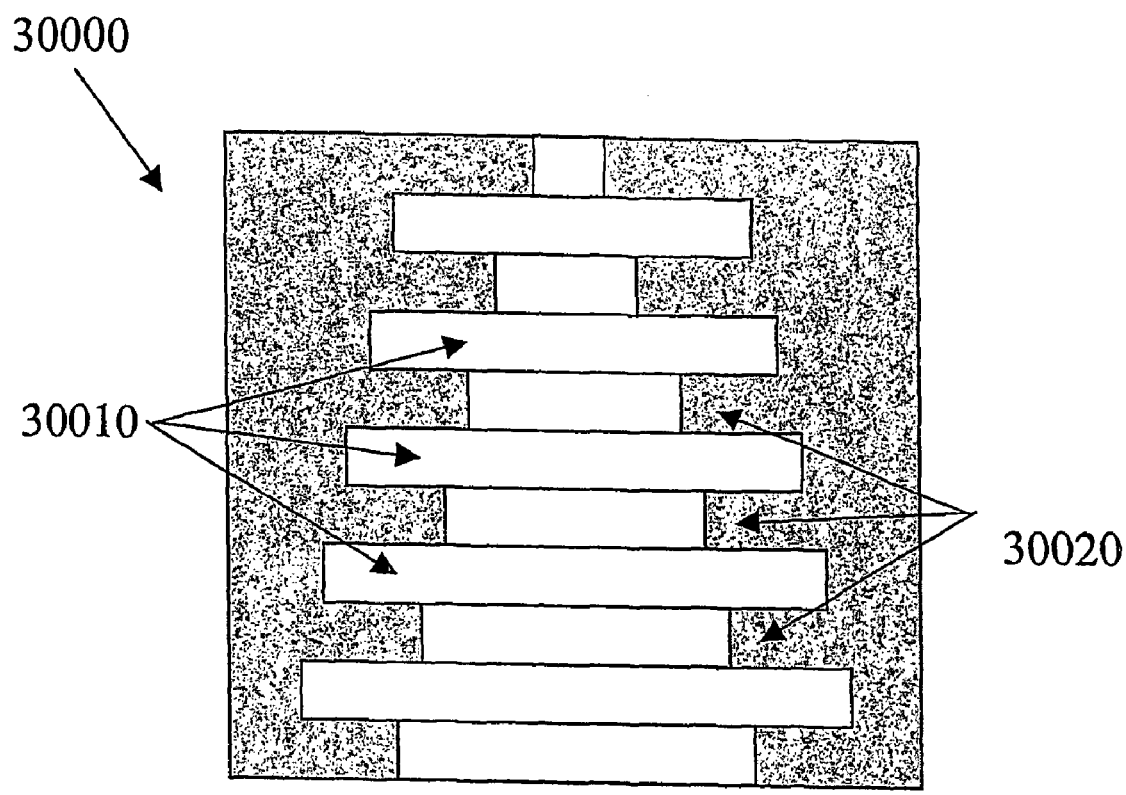
FIG. 30 is a cross-section of a cavity of the present invention taken along section lines 30-30 of FIG. 29.

FIG. 29 is a top view of stack lamination mold 29000 that defines an array of cavities 29010 for fabricating feedhorns. FIG. 30 is a cross-section of a cavity 29010 taken along section lines 30-30 of FIG. 29. As shown, cavity 29010 is corrugated, having alternating cavity slots 30010 separated by mold ridges 30020 of decreasing dimensions, that can be held to close tolerances.

In an exemplary embodiment, an array of feedhorns contains one thousand twenty identical corrugated feedhorns, each designed to operate at 500 GHz, and the overall dimensions of the feed horn array are 98 millimeters wide by 91 millimeters high by 7.6 millimeters deep. The fabrication of this exemplary array can begin with the creation of a laminated mold, comprised of micro-machined layers, and assembled into a precision stack lamination.

Step 1: Creating the laminated mold: The laminated mold in this example was made of 100 layers of 0.003" thick beryllium copper (BeCu) sheets that were chemically etched and then laminated together using an epoxy bonding process. Infinite Graphics, Inc. of Minneapolis, Minn. was contracted to produce the photo-masks needed for etching the layers. The masks were configured with one thousand twenty diameters having a center-to-center spacing of 2.5 millimeters. An IGI Lazerwrite photo plotter was used to create the masks, which were plotted on silver halite emulsion film. The plotter resolution accuracy was certified to 0.5 micrometers and pattern positional accuracy of plus or minus 0.40 micrometers per lineal inch. The layers were designed so that horn diameters were different from layer to layer, so that when the layers were assembled, the layers achieved the desired cross-section taper, slot, and ridge features shown in simplified form in FIG. 30. A total of 100 layers were used to create a stacked assembly 7.6 millimeters thick. The layers were processed by Tech Etch, Inc. of Plymouth, Mass., using standard photo-etching techniques and were etched in such a way that the cross-sectional shape of the etched walls for each layer are perpendicular to the top and bottom surfaces of the layer (commonly referred to as straight sidewalls).

In this example, the method chosen to bond the etched layers together used a thermo-cured, epoxy (MAGNA-TAC model E645), using the process and fixturing described earlier in the section on layer assembly and lamination. The assembled fixture was then placed in a 12 inch×12 inch heated platen press, Carver model No. 4122. The fixture was compressed to 40 pounds per square inch and held at a temperature of 350 degrees F. for 3 hours, then allowed to cool to room temperature under constant pressure. The assembly was then removed from the fixture and the alignment pins removed, leaving the bonded stack lamination. The laminated mold (stack lamination) was then used to produce the final casting mold.

Step 2: Creating the casting mold: The second step of the process was the assembly of the final casting mold, which used the precision stack lamination made during step 1 as a laminated mold. The casting mold created was a negative version of the lamination, as shown in perspective view for a single feed horn 31000 in FIG. 31. Also shown is a feedhorn ridge 31010 that can correspond to a cavity slot 30010, and a feedhorn base 31020.

For this example, Silastic® J RTV Silicone Rubber was used to make the final casting mold. This product was chosen because it is flexible enough to allow easy release from the laminated mold without damaging the undercut slots and rings inside the feedhorns, and because of its high-resolution capability. Described below are the product specifications.

Silastic® J:

| Durometer Hardness: | 56 Shore A points |
| Tensile Strength, psi: | 900 |
| Linear Coefficient of Thermal Expansion: | $6.2 \times 10^{-4}$ |
| Cure Time at 25 C.: | 24 hours |

The Silastic® J Silicone RTV was prepared in accordance with the manufacturer's recommendations. This included mixing the silicone and the curing agent and evacuating air (degassing) from the material prior to filling the mold-making fixture. At the time the example was prepared, the most effective way of degassing the Silicone prior to filling the mold fixture was to mix the two parts of the Silicone and place them in a bell jar and evacuate the air using a dual stage vacuum pump. The material was pumped down to an atmosphere of 28 inches of mercury and held for 5 minutes beyond the break point of the material. The Silicone was then ready to pour into the mold fixture.

Figure 32:
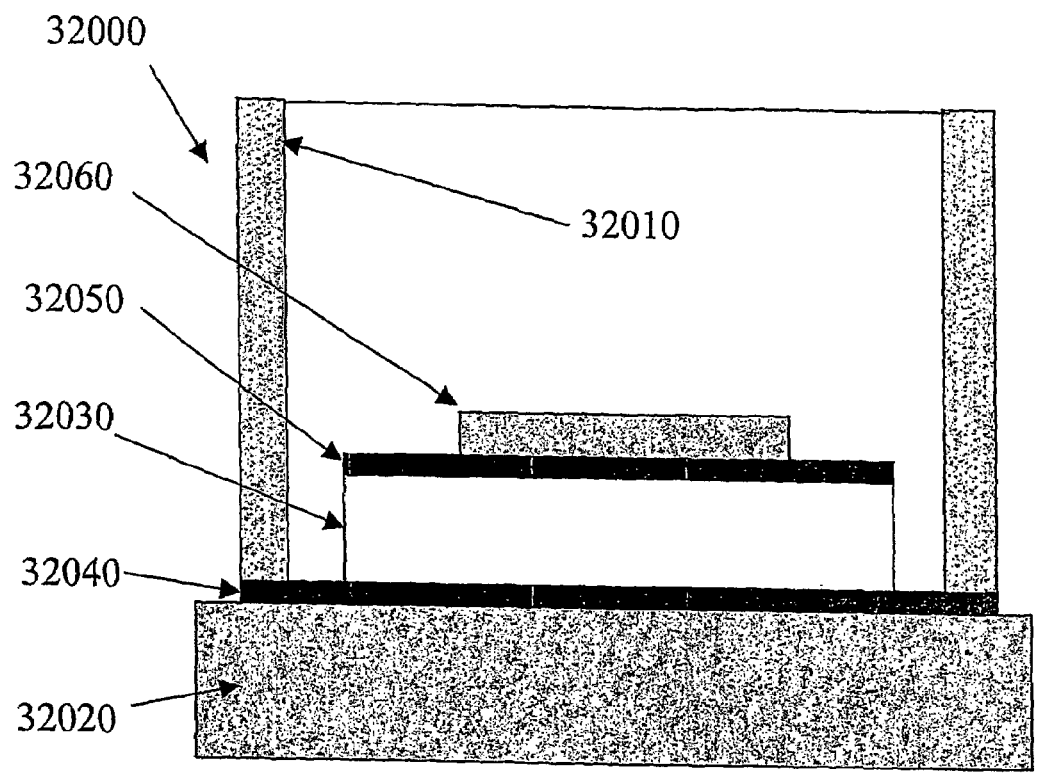
FIG. 32 is a side view of an exemplary casting fixture of the present invention.

As shown in the side view of FIG. 32, an open-face fixture 32000 was prepared, the fixture having a precision-machined aluminum ring 32010, precision ground glass plate 32030, rubber gaskets 32040, 32050 and the laminated mold 32060. The base 32020 of the fixture was thick plexiglass. On top of the plexiglass base was a glass substrate 32030. Rubber gasket 32040 separated the glass base and the glass substrate. An additional rubber gasket 32050 was placed on the top surface of the glass substrate 32030 and the laminated mold 32060 was placed on the top gasket. The rubber gaskets were used to prevent unwanted flashing of material during casting. A precision-machined aluminum ring 32010 was placed over the laminated mold subassembly and interfaced with the lower rubber gasket 32040.

Generally, the height of the ring and dimensions of the above pieces can depend upon the dimensions of the specific structure to be cast. The ring portion 32010 of the fixture assembly served several purposes, including bounding and defining the area in which to pour mold material, capturing the material during the curing process, and providing an air escape while the mold material was degassed using vacuum. The fixture was configured in a way that all sides surrounding the laminated mold 32060 were equal and common, in order to equalize and limit the effects of thermal or mechanical stresses put on the lamination from the mold material.

An open-face mold was used for this example. The mold insert and molding fixture were assembled and filled with the silicone RTV, then the air was evacuated again using a bell jar and vacuum pump in an atmosphere of 28 inches of mercury. After allowing sufficient time for the air to be removed from the silicone, the mold was then heat-cured by placing it in a furnace heated to and held at a constant temperature of 70 degrees F. for 16 hours prior to separating the laminated mold from the derived RTV mold. The molding fixture was then prepared for disassembly, taking care to remove the laminated mold from the RTV mold without damaging the lamination, since the lamination can be used multiple times to create additional RTV molds.

Figure 31:
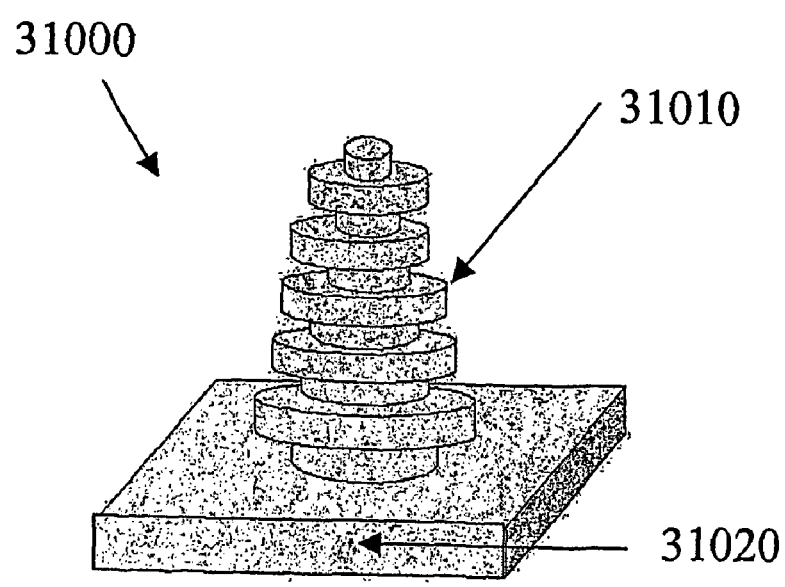
FIG. 31 is a perspective view of an exemplary single corrugated feedhorn of the present invention.

The resulting RTV mold was a negative version of the entire feedhorn array consisting of an array of one thousand twenty negative feedhorns, similar to the simplified single horn 31010 shown in perspective view in FIG. 31.

Step 3: Casting the feedhorn array: In this example, the cast feedhorn arrays were made of a silver loaded epoxy, which is electrically conductive. In certain exemplary embodiments of the present invention, binders and/or metallic (or other) powders can be combined and/or engineered to satisfy specific application and/or process specifications. The conductive epoxy chosen for this example provided the electrical conductivity needed to integrate the feedhorn array with an electronic infrared detector array.

The conductive epoxy was purchased from the company BONDLINE™ of San Jose, Calif., which designs and manufactures engineered epoxies using powdered metals. Certain of its composite metal epoxies can be cured at room temperature, have high shear strength, low coefficient of thermal expansion, and viscosities suited for high-resolution casting.

Exemplary embodiments of the present invention can utilize various techniques for injecting or filling cavity molds with casting materials. In this example, a pressure casting method was used.

The BONDLINE™ epoxy was supplied fully mixed and loaded with the silver metallic powder, in a semi-frozen state. The loaded epoxy was first normalized to room temperature and then pre-heated per the manufacturer's specification. In the pre-heated state the epoxy was uncured and ready to be cast. The uncured epoxy was then poured into the open-face mold to fill the entire mold cavity. The mold was then placed in a pressurized vessel with an applied pressure of 50 psi using dry nitrogen, and held for one hour, which provided sufficient time for the epoxy to cure. The mold was then removed from the pressure vessel and placed in an oven for 6 hours at 225 degrees F., which fully cured the conductive epoxy.

Step 4. Demolding and finish machining: After the cast epoxy had been cured, it was ready for disassembly and demolding from the casting fixture and mold. The mold material (RTV silicone) was chosen to be flexible enough to allow the cast feedhorn array to be removed from the casting mold without damaging the undercuts formed by the slots and ridges. When done carefully, the mold could be reused several times to make additional feedhorn arrays.

The backing thickness 31020 of the RTV mold shown in FIG. 31 came into play during the de-molding process. The backing was cast thick enough to allow easy grasping to assist with separating the casting mold from the cast piece. In this example, the RTV casting mold was flexible and allowed easy separation without damaging the undercut slots and rings inside the cast feedhorns.

Depending on the piece being cast, machining, coating, and/or other finish work can be desirable after de-molding. In this example, a final grinding operation was used on the top surface (pour side of the mold) of the feedhorn array because an open face mold was used. This final. grinding operation could have been eliminated by using a closed, two-part mold.

Example 2

Individual Feedhorns Produced in a Batch Process

This example makes use of certain exemplary embodiments of the present invention to demonstrate the production of sub-millimeter feedhorns in a batch process. The example uses the same part design and fabrication process described in example 1, with several modifications detailed below.

Process Modifications: The process detailed in example 1 was used to produce an array of one thousand twenty feedhorns. The first modification to the process was the casting material used to produce the array. The casting material for this example was a two-part casting polymer sold through the Synair Corporation of Chattanooga, Tenn. Product model "Mark 15 Por-A-Kast" was used to cast the feedhorn array and was mixed and prepared per the manufacturer's specifications. The polymer was also cast using the pressure filling method described in example 1.

The next modification was a surface treatment applied to the cast polymer array. A conductive gold surface was deposited onto the polymer array in order to integrate the feedhorns with the detector electronics. The gold surface was applied in two stages. The first stage was the application of 0.5 microns of conduction gold, which was sputter-coated using standard vacuum deposition techniques. The first gold surface was used for a conductive surface to allow a second stage electro-deposition or plating of gold to be applied. The second gold plating was applied with a thickness of 2 microns using pure conductive gold.

The final modification was to dice or cut the feedhorns from the cast and plated array into individual feedhorns, that were then suitable for detector integration. A standard dicing saw, used for wafer cutting, was used to cut the feedhorns from the cast array.

Example 3

Array of 3-dimensional Micro-Structures

Process steps 1 and 2 described in example 1 were used to produce a large area array of micro-structures, which are described as negatives of the feedhorn cavities, shown as a single feedhorn in FIG. 31. The laminated mold and molding fixture was used to cast the micro-structures using Dow Corning's Silastic® M RTV Silicone Rubber. This product was chosen because it is flexible enough to release from the mold insert, without damaging the circular steps in the structure, but has the hardness needed to maintain the microstructures in a standing position after being released from the mold. Described below are the product specifications.

Silastic® M

| | |
|---|---|
| Durometer Hardness: | 59 Shore A points |
| Tensile Strength, psi: | 650 |
| Linear Coefficient of Thermal Expansion: | $6.2 \times 10^{-4}$ |
| Cure Time at 25 C.: | 16 hours |

The Silicone RTV was prepared in accordance with the manufacturer's recommendations, using the process described earlier in example 1, step 2. The laminated mold and molding fixture were assembled and filled with the silicone RTV, using the process described earlier in example 1, step 2. The molding fixture was then prepared for disassembly, taking care to separate the mold insert from the cast silicone array. The resulting casting was an array consisting of one thousand twenty 3-dimensional micro-structures. The shape and dimension of a single structure is shown in simplified form in FIG. 31.

Example #4

Cylindrical Tubing with Micro-fluidic Channels on the Inside Diameter

Certain exemplary embodiments of the present invention have been used to produce a 2.5 centimeter length of clear urethane tubing, having 3-dimensional micro-fluid channels on the inside diameter of the tubing. The fluidic tubing was produced using a flexible cavity insert with a controlled backing thickness. The following example demonstrates how the cavity insert can enable the production of three-dimensional features on the inside and outside diameters of cylindrical tubing.

Figure 33:
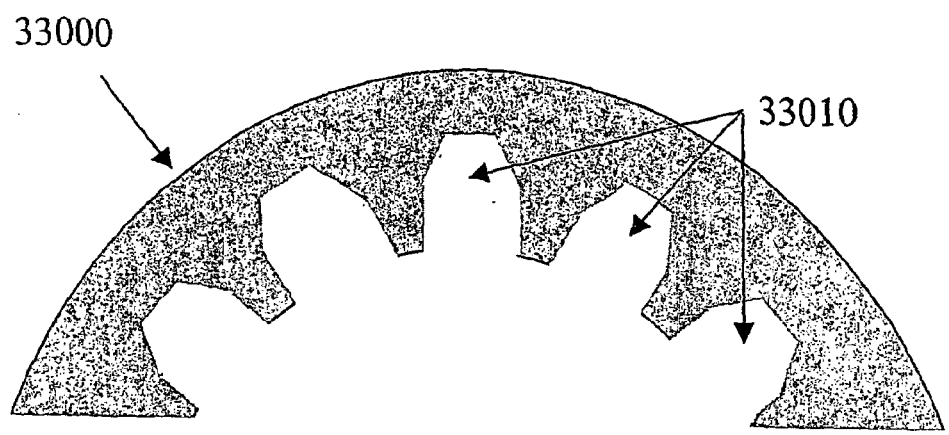
FIG. 33 is a side view of an exemplary section of cylindrical tubing of the present invention that demonstrates the shape of an exemplary fluidic channel of the present invention.

Step 1: Creating the mold insert: The first step in the process was to fabricate the micro-machined layers used to produce the cavity insert. The cast tubing was 2.5 centimeters long, having a 3.0 millimeter outside diameter and a 2.0 millimeter inside diameter, with 50 three-dimensional micro-fluidic channels, equally spaced around the interior diameter of the tube. FIG. 33 shows a side view of the tubing 33000, the wall of which defines numerous fluidic channels 33010. Although each fluidic channel could have different dimensions, in this example each channel was 0.075 mm in diameter at the entrance of the channel from the tube, and each channel extended 0.075 mm deep. Each channel tapered to a diameter of 0.050 mm, the taper beginning 0.025 mm from the bottom of each channel.

Figures 34, 35:
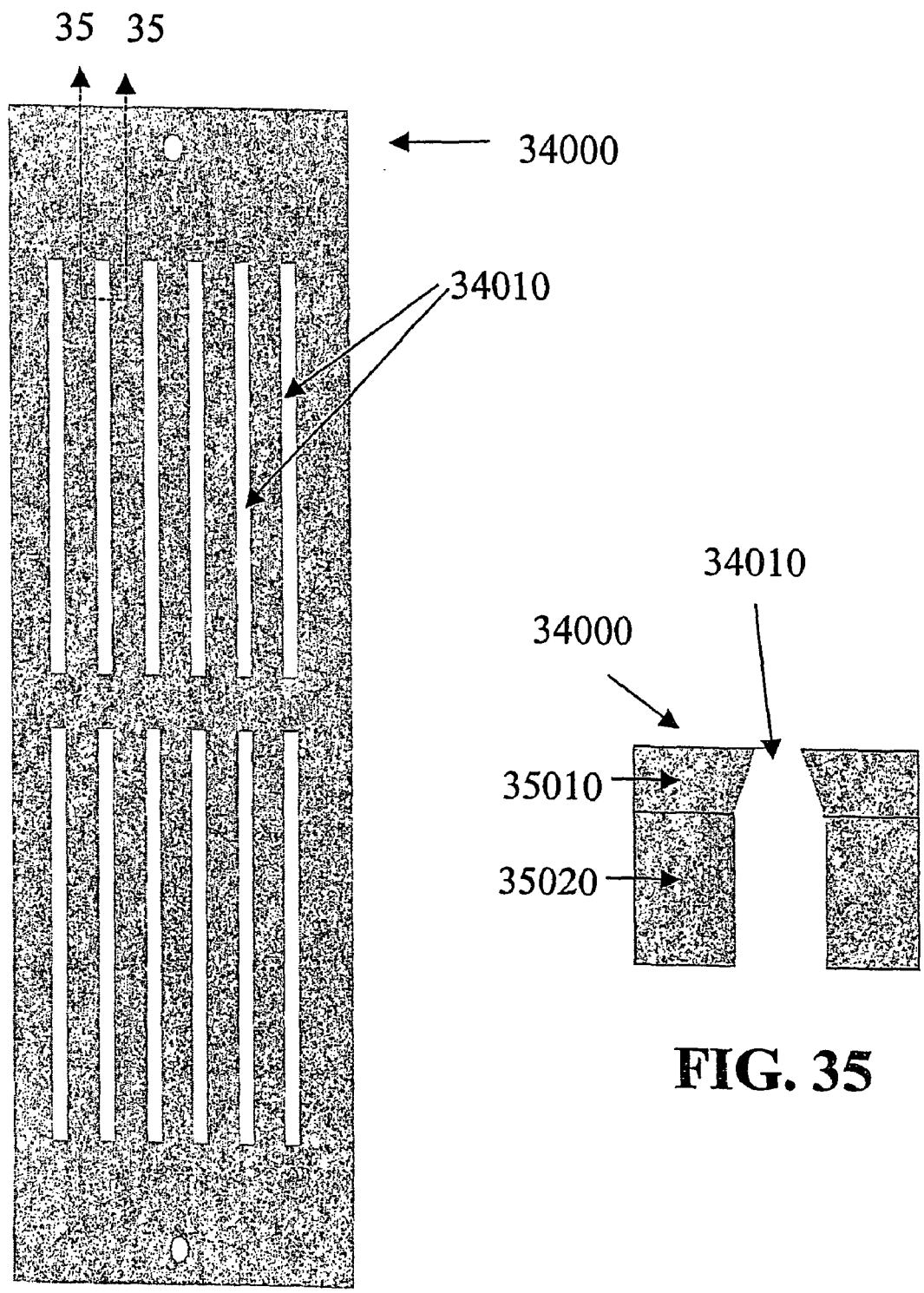
FIG. 34 is a top view of an exemplary micro-machined layer of the present invention.
FIG. 35 is a cross-sectional view of a laminated slit of the present invention taken along section lines 35-35 of FIG. 34.

Photo-chemical machining was used to fabricate the layers for the laminated mold. FIG. 34 is a top view of a such a laminated mold 34000, which was created using several photo masks, one of which with a similar top view. Mold 34000 includes an array of fluidic channels 34010 In this particular experiment, the length of channels 34010 was approximately 25 millimeters, and the width of each collection of channels was approximately 6.6 millimeters.

FIG. 35 is a cross-section of mold 34000 taken at section lines 35-35 of FIG. 34. To the cross-sectional shape of channel 34010, a first copper foil 35010 having a thickness of 0.025 mm, and a second copper foil 35020 having a thickness of 0.050 mm, were chemically etched and then laminated together using a metal-to-metal brazing process. Each of the layers used in the laminated mold assembly used a separate photo-mask. The masks used for layer 35020 were configured with a 9.50×0.075 mm rectangular open slot, arrayed redundantly in 50 places, a portion of which are illustrated in FIG. 34. To achieve the desired taper, two masks were used for layer 35010. The bottom mask was configured with a 9.50× 0.075 mm rectangular open slot and the top mask was configured with a 9.50×0.050 rectangular open slot, each of the slots were also redundantly arrayed in 50 places. The photo-masks were produced to the same specifications, by the same vendor as those described in example 1, step 1.

The layers were designed so that the slot placement was identical from layer to layer, which when assembled, produced the cross-sectional shape for the channels as shown in FIG. 35. The final thickness of the lamination was specified at 0.083 millimeters, which required one 0.025 layer of copper foil, and one 0.050 thick layer of copper foil, leaving a total thickness amount of 0.002 millimeters for braze material on each side of each etched layer. The layers were photo-etched by the same vendor, and same sidewall condition as those described in example 1, step 1. The method chosen to bond the grid layers together was a metal-to-metal brazing technique described earlier, in detail as one of two exemplary methods of bonding layers together (eutectic braze alloy)

Figure 36:
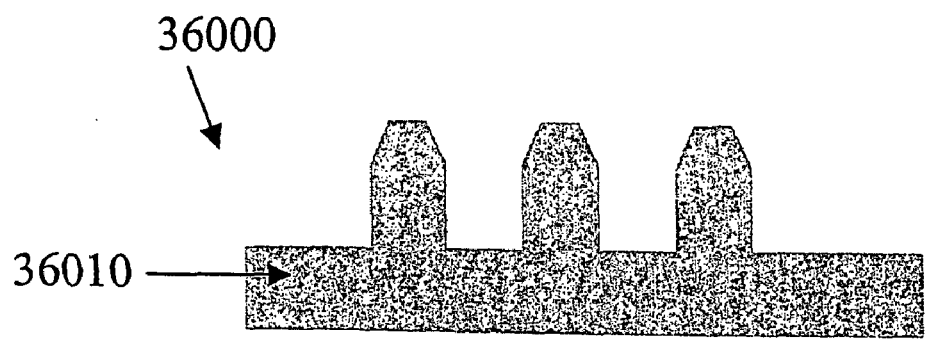
FIG. 36 is a side view of a portion of an exemplary flexible cavity insert of the present invention.

Step 2: Creating the flexible cavity insert: The next step of the process was to create a flexible cavity insert from the brazed layered assembly. FIG. 36 is a side view of cavity insert 36000, which was produced from the brazed assembly insert 36000 with a backing 36010 having a thickness of 0.050 millimeters. The cavity insert 36000 was produced using Silastic® S RTV Silicone Rubber as the base material. The RTV Silicone Rubber was used because of its resolution capability, release properties, dimensional repeatability, and its flexibility to form the insert to a round pin that would be assembled to the final molding fixture. The material properties of Silastic® S are shown below.

Silastic® S

| | |
|---|---|
| Durometer Hardness: | 26 Shore A points |
| Tensile Strength, psi: | 1000 |
| Linear Coefficient of Thermal Expansion: | $6.2 \times 10^{-4}$ |
| Cure Time at 25 C.: | 24 hours |

The casting fixture used to create the RTV cavity insert was similar to that shown in FIG. 32 and is described in detail in the prior examples. A modification was made to the fixture assembly, which was a top that was placed over the pour area of the mold fixture. This top was placed and located to close the mold after air evacuation and reduce the backing thickness 36010 of the RTV insert to a thickness of 0.050 millimeters, shown in FIG. 36. The Silastic® S RTV Silicone Rubber used for the cavity insert fabrication was prepared in accordance with the manufacturers recommendations, using the process described earlier in example 1, step 2.

Figure 37:
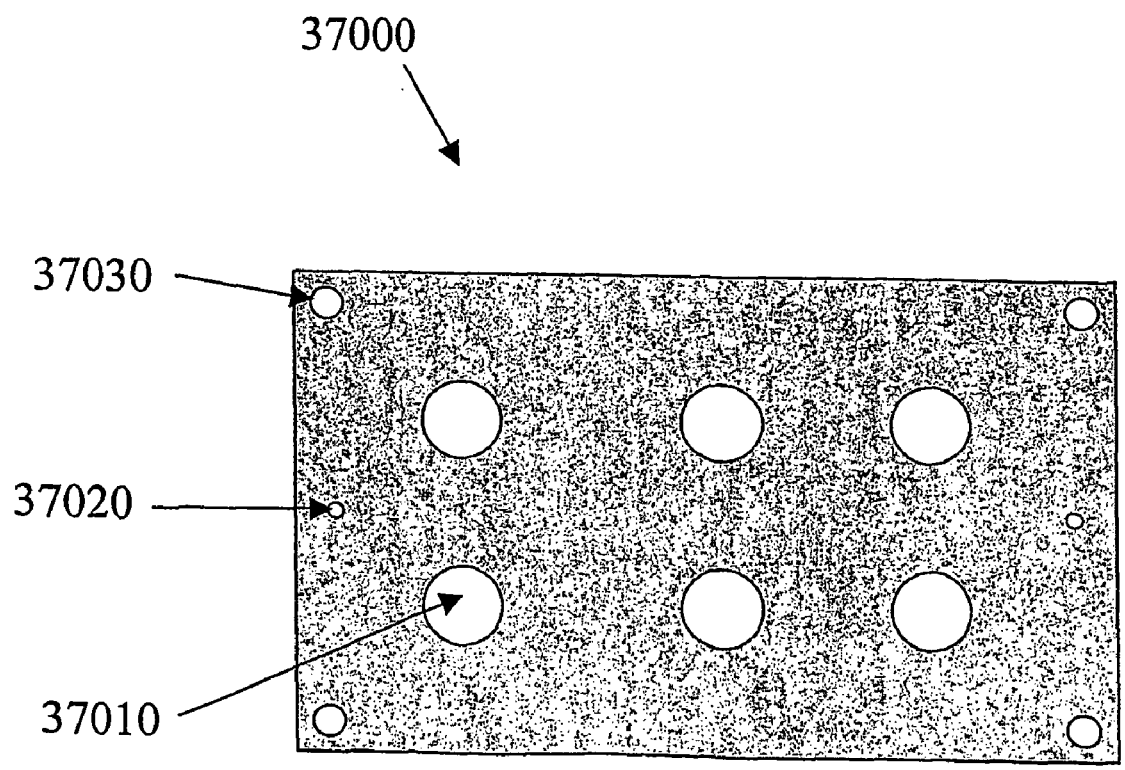
FIG. 37 is a top view of an exemplary base plate of the present invention.
Figure 40:
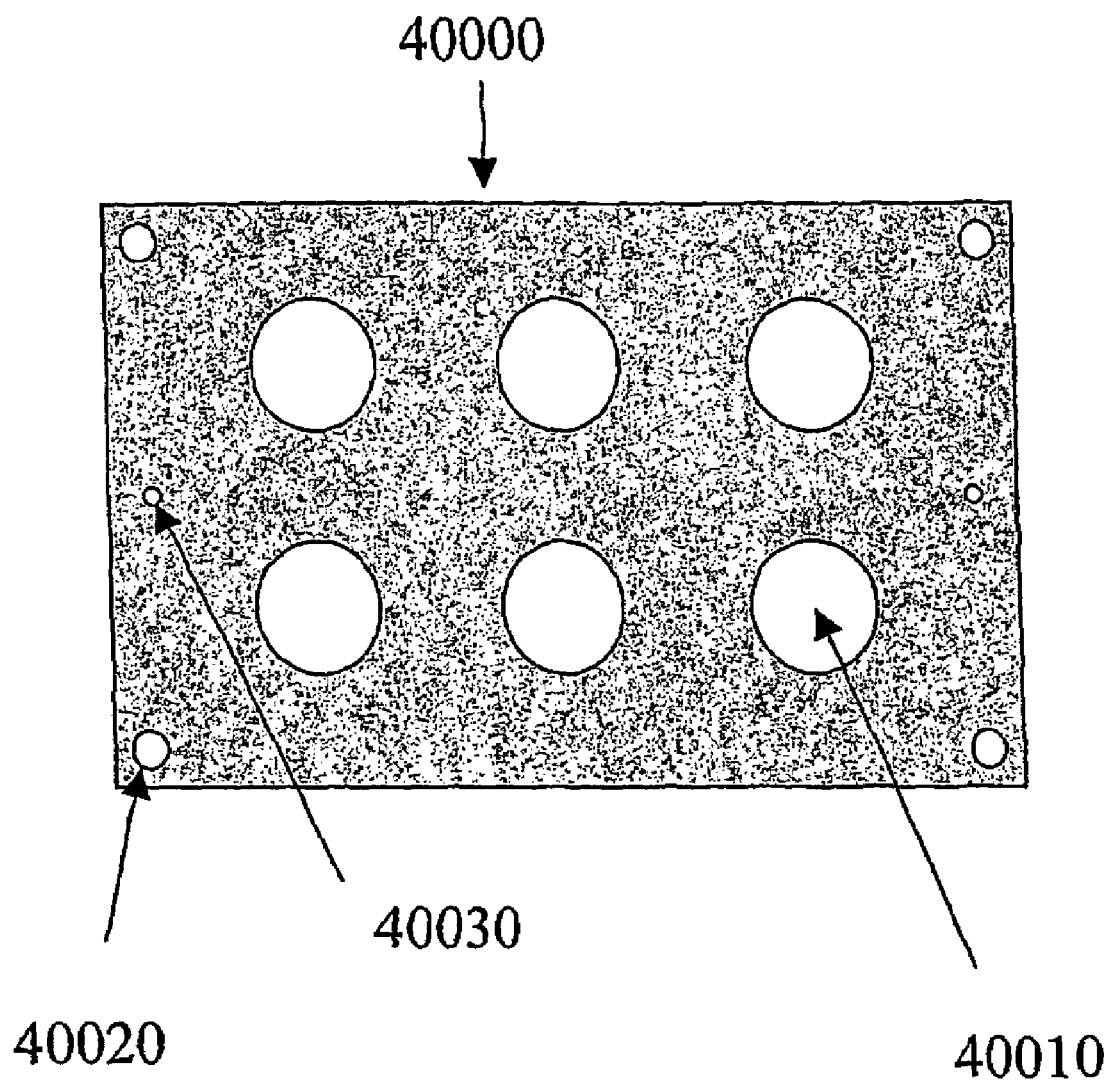
FIG. 40 is a top view of a top plate of the present invention.

Step 3: Assembling the molding fixture: The final molding fixture was then ready to be assembled. The molding fixture included a base plate (FIG. 37), the cavity inserts (FIG. 38), and a top plate (FIG. 40). FIG. 37 is a top view of the base plate 37000, which was made from a 0.25 inch aluminum plate that was ground flat and machined using standard CNC machining techniques. The base had six machined diameters 37010 through the plate. These six diameters would accept the cavity insert pins described later. The plate also had machined diameters through the plate, which would accept dowel pins 37020 that were used to align and assemble the top plate and the base plate, as well as 4 bolt diameters 37030 to hold the top and bottom plates together.

FIG. 38 is a side view of an insert fixture 38000, that includes the flexible cavity insert 36000 attached to a 3 centimeter long, 1.900 millimeter diameter steel pin 38010. The pin 38010 was ground to the desired dimensions using standard machine grinding techniques. The RTV cavity insert 36000 was cut to the proper size before being attached to the pin. The RTV insert 36000 was attached to outside diameter of the pin 38010 using a controlled layer of two-part epoxy.

FIG. 39 is a side view of several insert fixtures 39000 that have been attached to a base plate 37000. Each insert 36000 was attached its corresponding pin 38010 so that the end of pin 38010 could be assembled to a corresponding machined diameter 37010 of base plate 37000 without interference from insert 36000. Once each insert 36000 was attached around the diameter of its corresponding pin 38010 and the pin placed in the corresponding through-diameter of base plate 37010, the pin was held perpendicular to base plate 37000 and in alignment with a top plate of the fixture.

FIG. 40 is a top view of a top plate 40000 of the fixture, which was also fabricated of aluminum and machined using CNC techniques. There were six 3.0 millimeter diameters

40010 milled through the thickness of plate 40000, which was 3.0 centimeters thick. Diameters 40010 defined the cavity areas of the mold that would be filled during the final casting process, and aligned to the pins assembled to the base plate. Also incorporated into the top plate were bolt features 40020 and dowel features 40030 needed to align and assemble the top plate 40000 to the base plate 37000. The thickness of top plate 40000 was specified to slightly exceed the desired length of the final cast tubing, which was cut to its final length after casting. The casting fixture was then assembled, first by assembling the cavity insert 38000 to the base plate 37000, followed by assembling the top plate 40000 to the base using bolts and dowels. The top view of a representative cavity section for an assembled fixture is shown in FIG. 19.

Step 4: Casting the fluidic tubes: Several fluidic tubes were produced using the assembled casting fixture. A clear urethane was used for the final casting because of its high-resolution, low shrink factor, and transparent properties, which allowed for final inspection of the interior diameter features through the clear wall of the tube. The casting material was purchased from the Alumilite Corporation of Kalamazoo, Mich., under the product name Water Clear urethane casting system. The manufacturer described the cured properties as follows:

| Hardness, Shore D: | 82 |
| Density (gm/cc) | 1.04 |
| Shrinkage (in/in/) maximum | 0.005 |
| Cure Time (150 degrees F.) | 16 hr |

The urethane was prepared in accordance with the manufacturer's recommendations. This included the mixing and evacuation of air (degassing) from the material prior to filling the mold. The most effective way found for degassing the urethane prior to filling the mold fixture was to mix parts A and B, place them in a bell jar, and evacuate the air using a dual stage vacuum pump. The mixture was pumped down to an atmosphere of 28 inches of mercury and held for 15 minutes beyond the break point of the material The urethane was then ready to pour into the mold fixture.

The assembled mold fixture was heated to 125 degrees F. prior to filling the cavities with the urethane. The pre-heating of the mold helped the urethane to flow and fill the cavities of the mold, and aided in the degassing process. The cavity sections of the mold were then filled with the urethane, and the air was evacuated again using a bell jar and vacuum pump in an atmosphere of 28 inches of mercury. After allowing sufficient time for the air to be removed from the urethane, the mold was then removed from the vacuum bell jar and placed in an oven. The mold was heated and held at a constant temperature of 150-180 degrees F. for 16 hours prior to separating the cast tubes from the mold. The molding fixture was then disassembled and the cast tubes were separated from the cavity inserts. The inserts were first removed from the base plate of the fixture. The tubes were easily separated from the cavity insert assembly due to the flexibility and release properties of the silicone RTV, combined with the hardness of the urethane tubes.

Example #5

Tubing with Micro-fluidic Channels on the Outside Diameter

Example #4 described the method used for producing cast urethane tubing with micro-fluidic features on the inside diameter of the tube. The current example demonstrates how that process can be altered to produce tubing with the micro-fluidic channels on the outside diameter of the tubing. This example uses a similar part design and the fabrication process described in example 4, with several modifications detailed below.

One process modification involved step 3, assembling the molding fixture. For this step, a modification was made to the fixture design that enabled the molded features to be similar to that shown in FIGS. 20-22. The first modification was in the size of the machined diameters in the base plate and the top plate of the fixture described in example 4. The flexible RTV cavity insert that was attached to a pin in example 4 was instead attached to the inside diameters of the top fixture plate, similar to that shown in FIG. 22. In order to accommodate the existing RTV cavity insert, the cavity diameters of the top plate were milled to a size of 1.900 millimeters. The RTV cavity insert was then attached to the milled diameter of the top plate using the same epoxy technique described in example 4. The base plate of the fixture was also modified to accept a 1.0 millimeter diameter pin, and was assembled similar to the that shown in FIG. 22. The same casting process was used as described in example 4. After following the final casting process, with the altered molding fixture, the urethane tubes were produced having the same fluidic channels located on the outside diameter of the cast tube.

Additional Embodiments

X-Ray and Gamma-Ray Collimators, Grids, and Detector Arrays

Certain exemplary embodiments of the present invention can provide methods for fabricating grid structures having high-resolution and high-aspect ratio, which can be used for radiation collimators, scatter reduction grids, and/or detector array grids. Such devices can be used in the field of radiography to, for example, enhance image contrast and quality by filtering out and absorbing scattered radiation (sometimes referred to as "off-axis" radiation and/or "secondary" radiation).

For the purposes of this description, the term "collimator" is used generally to describe what may also be referred to herein as radiation collimators, x-ray grids, scatter reduction grids, detector array grids, or any other grid used in radiography apparatuses and processes.

Certain collimators fabricated according to one or more exemplary embodiments of the present invention can be placed between the object and the image receptor to absorb and reduce the effects of scattered x-rays. Moreover, in certain exemplary embodiments, such collimators can be used in a stationary fashion, like those used in SPECT (Single Photon Emission Computed Tomography) imaging, or can be moved in a reciprocating or oscillating motion during the exposure cycle to obscure the grid lines from the image, as is usually done in x-ray imaging systems. Grids that are moved are known as Potter-Bucky grids.

X-ray grid configurations can be specified by grid ratio, which can be defined as the ratio of the height of the grid to the distance between the septa. The density, grid ratio, cell configuration, and/or thickness of the structure can have a direct impact on the grid's ability to absorb off-axis radiation and/or on the energy level of the x-rays that the grid can block.

Certain exemplary embodiments of the present invention can allow for the use of various materials, including high-density grid materials. Also, certain exemplary can make use of a production mold, which can be derived from a laminated mold.

Numerous additional aspects can be fabricated according to certain exemplary embodiments of the present invention. For example, the laminated mold can be produced from a stack lamination or other method, as discussed above. Moreover, X-ray absorbent material, such as lead, lead alloys, dense metallic composites, and/or epoxies loaded with dense metallic powders can be cast into a mold to produce x-ray absorbing grids. High-temperature ceramic materials also can be cast using a production mold.

In addition, the open cells of the ceramic grid structure can be filled with detector materials that can be accurately registered to a collimator. The molds and grids can be fabricated having high-resolution grid geometries that can be made in parallel or focused configurations. The mold can remain assembled to the cast grid to provide structural integrity for grids with very fine septal walls, or can be removed using several methods, and produce an air-cell grid structure.

Figure 41:
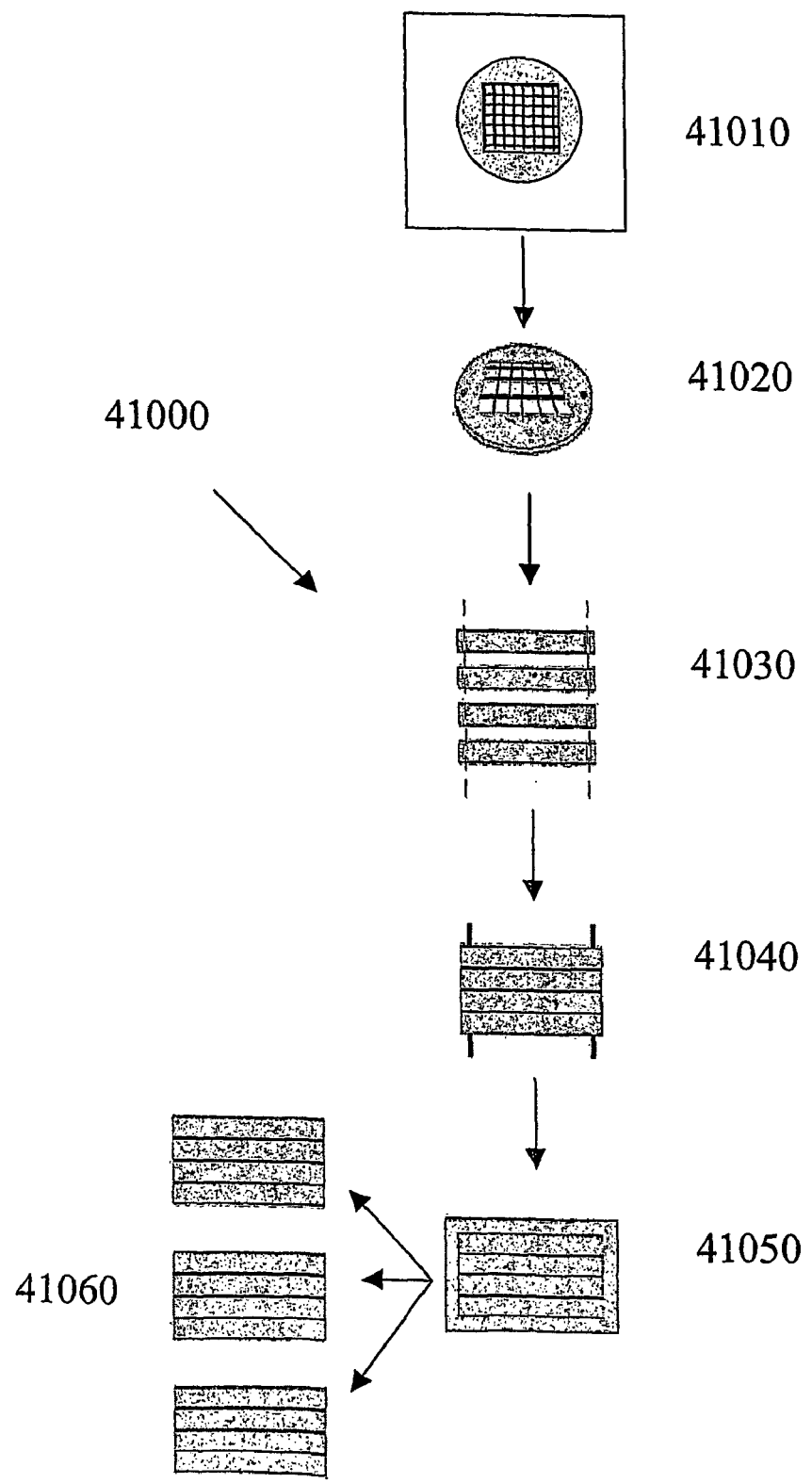
FIG. 41 is a flowchart of an exemplary embodiment of a method of the present invention.

FIG. 41 is a block diagram illustrating an exemplary embodiment of a method 41000 of the present invention Method 41000 can include the following activities:

1) creating a lithographic mask 41010 defining the features of each unique layer,
2) using lithographic micro-machining techniques and/or micro-machining techniques to produce patterned layers 41020, and
3) aligning, stacking, and/or laminating the patterned layers 41030 in order to achieve the desired 3-dimensional cavity shape, high-aspect ratios, and/or other device features desired for the laminated mold 41040,
4) fabricating a casting mold 41050 derived from the laminated mold, and/or
5) casting x-ray grids (or other parts) 41060 using the derived casting mold.

The following discussion describes in detail exemplary activities involved in fabricating certain exemplary embodiments of a laminated mold, fabricating a derived mold from the laminated mold, and finally casting a collimator from the derived mold. Certain variations in the overall process, its activities, and the resulting collimator are noted throughout.

In certain exemplary embodiments, the final collimator can be customized as a result of the casting process. For instance, conventional collimators have two separated flat major sides that are parallel to each other, thereby forming a flat, generally planar grid structure. Although certain exemplary embodiments of the present invention includes methods for forming these collimators, exemplary embodiments of the invention also can be used to form non-planar collimators.

An exemplary embodiment of a method of the present invention can begin with the acquisition, purchase, and/or fabrication of a first collimator. This first collimator can serve as the master collimator from which one or more molds can be formed. The master collimator can be made by any means, including stack lamination, but there is no limitation with respect to how the first or master collimator can be made. Also, as will be explained in more detail, because the master collimator is not necessarily going to be a collimator used in radiography, it is possible to customize this master collimator to facilitate mold formation.

The mold itself can be fabricated of many materials. When formed of a flexible material, for example, it is possible to use the mold to make a non-planar collimator. The material of the mold can be customized according to cost and performance requirements. In some embodiments, it is possible to make a mold of material that is substantially transparent to radiation transmission. The mold could be left embedded in the final cast collimator. This particular variation can be applicable when the final collimator has very narrow septal walls and the mold is needed to provide support and definition for the collimator. The mold generally also can be reused to form multiple final (or second) collimators to achieve economies of manufacturing scale.

Radiation Opaque Casting Materials for Collimators and Grids

A broad selection of base materials can be used for the fabrication of parts, such as x-ray collimators and scatter reduction grids. One potential characteristic of a grid material is sufficient absorption capacity so that it can block selective x-rays or gamma photons from reaching an image detector. In certain embodiments of the present invention, this characteristic can require high density and/or high atomic number (high z) materials. Certain exemplary embodiments of the present invention can utilize lead, tungsten, and/or various lead alloys for grid fabrication, but also can include the practice of loading various binders or alloys with dense powder metals, such as tungsten. The binders can be epoxies, polymers, and/or dense alloys which are described in detail below.

For certain exemplary embodiments of the present invention, lead can be used for casting purposes because of its high density and low melting point, which can allow the molten lead to be poured or injected into a mold. In certain situations, however, pure lead can shrink and/or pull away from molds when it solidifies, which can inhibit the casting of fine features. This can be overcome by using lead alloys, made from high-density materials, which can allow the metal alloy to flow at lower temperatures than pure lead while reducing shrink factors.

A typical chief component in a lead alloy is bismuth, a heavy, coarse crystalline metal that can expand by 3.3% of its volume when it solidifies. The presence of bismuth can expand and/or push the alloy into the fine features of the mold, thus enabling the duplication of fine features. The chart below shows the physical properties of pure lead and two lead alloys that were used to produce collimators. The alloys were obtained from Cerro Metal Products Co. of Bellefonte, Pa. Many other alloys exist that can be used to address specific casting and application requirements.

| BASE MATERIAL | COMPOSITION | MELT POINT | DENSITY (g/cc) |
| --- | --- | --- | --- |
| Pure Lead | Pb | 621.7 degrees F. | 11.35 |
| CERROBASE ™ | 55.5% BI, 44.5% Pb | 255 degrees F. | 10.44 |
| CERROLOW-117 ™ | 44.7% BI, 22.6% Pb, 19.1% In, 8.3% Sn, 5.3% Cd, | 117 degrees F. | 9.16 |

The physical properties of lead alloys can be more process-compatible when compared to pure lead, primarily because of the much lower melting point. For example, the low melt point of CERROBASE™ can allow the use of rubber-based molds, which can be helpful when casting fine-featured pieces. This can be offset in part by a slightly lower density (about 8%). The somewhat lower density, can be compensated for, however, by designing the grid structure with an increased thickness and/or slightly wider septal walls.

Also, the alloy can be loaded with dense powder metals, such as tungsten, gold, and/or tantalum, etc., to increase density. Similarly, epoxy binders can be loaded with a metallic powder such as, for example, powdered tungsten, which has a density of 19.35 grams per cubic centimeter. In this approach, tungsten particles ranging in size from 1-150 microns, can be mixed and distributed into a binder material. The binder material can be loaded with the tungsten powder at sufficient amounts needed to achieve densities ranging between 8 and 14 grams per cubic centimeter. The tungsten powder is commercially available through the Kulite Tungsten Corporation of East Rutherford N.J., in various particle sizes, at a current cost of approximately $20-$25 dollars per pound.

The binders and metallic powders can be combined and engineered to satisfy specific application and process issues. For example, tungsten powder can be added to various epoxies and used for casting.

The company BONDLINE™ of San Jose, Calif., designs and manufactures engineered adhesives, such as epoxies, using powdered metals. Such composite metal epoxies can be cured at room temperature, can have high shear strength, low coefficient of thermal expansion, and viscosities that can be suited for high-resolution casting. Powdered materials combined with epoxy can be stronger than lead or lead alloys, but can be somewhat lower in density, having net density ranging from 7-8 grams per cubic centimeter. This density range can be acceptable for some collimator applications. In applications where material density is critical the practice of loading a lead alloy can be used. For example, tungsten powder can be combined with CERROBASE™ to raise the net density of the casting material from 10.44 up to 14.0 grams per cubic centimeter.

Certain exemplary embodiments of the present invention also include the casting of grid structures from ceramic materials, such as alumina, silicon carbide, zirconium oxide, and/or fused silica. Such ceramic grid structures can be used to segment radiation imaging detector elements, such as scintillators. The Cotronics Corporation of Brooklyn, N.Y., manufactures and commercially distributes Rescor™ Cer-Cast ceramics that can be cast at room temperature, can have working times of 30-45 minutes, can have cure times of 16 hours, and can withstand temperatures ranging from 2300 to 4000 degrees F.

Additional Embodiments

Anti-Scatter Grids for Mammography and General Radiography

One or more exemplary embodiments of the present invention can provide cellular air cross grids for blocking scattered X-ray radiation in mammography applications. Such cross grids can be interposed between the breast and the film-screen or digital detector. In some situations, such cross grids can tend to pass only the primary, information-containing radiation to the film-screen while absorbing secondary and/or scattered radiation which typically contains no useful information about the breast being irradiated.

Certain exemplary embodiments of the present invention can provide focused grids. Grids can be made to focus to a line or a point. That is, each wall defining the grid can be placed at a unique angle, so that if an imaginary plane were extended from each seemingly parallel wall, all such planes would converge on a line or a point at a specific distance above the grid center—the distance of that point from the grid known as the grid focal distance. A focused grid can allow the primary radiation from the x-ray source to pass through the grid, producing the desired image, while the off-axis scattered rays are absorbed by the walls of the grid (known as septal walls).

In certain embodiments, the septal walls can be thick enough to absorb the scattered x-rays, but also can be as thin as possible to optimize the transmission ratio (i.e., the percentage of open cell area to the total grid area including septal walls) and minimize grid artifacts (the shadow pattern of grid lines on the x-ray image) in the radiograph.

The relation of the height of the septal walls to the distance between the walls can be known as the grid ratio. Higher grid ratios can yield a higher scatter reduction capability, and thus a higher Contrast Improvement Factor (CIF), which can be defined as the ratio of the image contrast with and without a grid. A higher grid ratio can require, however, a longer exposure time to obtain the same contrast, thus potentially exposing the patient to more radiation. This dose penalty, known as the Bucky factor (BF), is given by $BF=CIF/Tp$, where $Tp$ is the fraction of primary radiation transmitted. Certain exemplary embodiments of the present invention can provide a grid design that arrives at an optimal and/or near-optimal combination of these measures.

One or more exemplary embodiments of the present invention can include fine-celled, focused, and/or large area molded cross-grids, which can be sturdily formed from a laminated mold formed of laminated layers of metal selectively etched by chemical milling or photo-etching techniques to provide open focused passages through the laminated stack of etched metal layers. In certain applications, such molded and/or cast cross grids can maximize contrast and accuracy of the resulting mammograms when produced with a standard radiation dosage.

In certain exemplary embodiments, the laminated mold for the molded cross grids can be fabricated using adhesive or diffusion bonding to join abutting edges of thin partition portions of the laminated abutting layers with minimum intrusion of bonding material into the open focused passages.

Exemplary embodiments of the present invention can utilize any of a wide number of different materials to fabricate such molded and/or cast cross grids. A specific application can result in any of the following materials being most appropriate, depending on, for example, the net density and the cell and septa size requirements:

Lead or lead alloy alone can offer a density of 9-11 grams per cc;
Lead alloy can be loaded with a dense composite (e.g., tungsten, tantalum, and/or gold, etc.) powder to form a composite having a density of 12-15 grams per cc;
Polymer can be loaded with a dense composite (e.g., lead, tungsten, tantalum, and/or gold, etc.) powder to form a composite having a density of 8-9 grams per cc;
The cast grid made of lead alloy or any of the above combinations can be encapsulated in a low density polymer such that the transmission is minimally affected but scatter is significantly reduced.

In addition, certain embodiments of the present invention can be employed to fabricate grids and/or collimators for which the mold can be pre-loaded with dense powder, followed by alloy or polymer. Alternatively, polymer or alloy can be pre-loaded with dense powder then injected into the mold. In certain embodiments, the casting can be removed from a flexible mold. In other embodiments, the mold can be dissolved or consumed to de-mold the casting. In certain embodiments, a master can be removed layer-by-layer from rigid mold. Alternatively, the lost wax approach can be used in which the model is dissolvable wax, dissolvable PMMA, dissolvable polyurethane, dissolvable high-resolution ceramic, and/or some other dissolvable material.

Additional Embodiments

Computed Tomography Collimator and Detector Array

Certain exemplary embodiments of the present invention can provide a system that includes an x-ray source, a scatter collimator, and a radiation detector array having a plurality of reflective scintillators. Such a system can be used for computer-assisted tomography ("CT").

In certain exemplary embodiments of the present invention, the x-ray source can project a fan-shaped beam, which can be collimated to lie within an X-Y plane of a Cartesian coordinate system, referred to as the "imaging plane". The x-ray beam can pass through the object being imaged, such as a patient. The beam, after being attenuated by the object, can impinge upon the array of radiation detectors. The intensity of the attenuated beam radiation received at the detector array can be dependent upon the attenuation of the x-ray beam by the object. Each detector element of the array can produce a separate electrical signal that can provide a measurement of the beam attenuation at the detector location. The attenuation measurements from all the detectors can be acquired separately to produce an x-ray transmission profile of the object.

For certain exemplary embodiments of the present invention, the detector array can include a plurality of detector elements, and can be configured to attach to the housing. The detector elements can include scintillation elements, or scintillators, which can be coated with a light-retaining material. Moreover, in certain exemplary embodiments, the scintillators can be coated with a dielectric coating to contain within the scintillators any light events generated in the scintillators. Such coated scintillators can reduce detector element output gain loss, and thereby can extend the operational life of a detector element and/or array, without significantly increasing the costs of detector elements or detector arrays.

In certain exemplary embodiments of the present invention, the x-ray source and the detector array can be rotated with a gantry within the imaging plane and around the object to be imaged so that the angle at which the x-ray beam intersects the object can constantly change. A group of x-ray attenuation measurements, i.e., projection data, from the detector array at one gantry angle can be referred to as a "view", and a "scan" of the object can comprise a set of views made at different gantry angles during one revolution of the x-ray source and detector. In an axial scan, the projection data can be processed to construct an image that corresponds to a two-dimensional slice taken through the object.

In certain exemplary embodiments of the present invention, images can be reconstructed from a set of projection data according to the "filtered back projection technique". This process can convert the attenuation measurements from a scan into integers called "CT numbers" or "Hounsfield units", which can be used to control the brightness of a corresponding pixel on a cathode ray tube display.

In certain exemplary embodiments of the present invention, detector elements can be configured to perform optimally when impinged by x-rays traveling a straight path from the x-ray source to the detector elements. Particularly, exemplary detector elements can include scintillation crystals that can generate light events when impinged by an x-ray beam. These light events can be output from each detector element and can be directed to photoelectrically responsive materials in order to produce an electrical signal representative of the attenuated beam radiation received at the detector element. The light events can be output to photomultipliers or photodiodes that can produce individual analog outputs. Exemplary detector elements can output a strong signal in response to impact by a straight path x-ray beam.

Without a collimator, X-rays can scatter when passing through the object being imaged. Particularly, the object can cause some, but not all, x-rays to deviate from the straight path between the x-ray source and the detector. Therefore, detector elements can be impinged by x-ray beams at varying angles. System performance can be degraded when detector elements are impinged by these scattered x-rays. When a detector element is subjected to multiple x-rays at varying angles, the scintillation crystal can generate multiple light events. The light events corresponding to the scattered x-rays can generate noise in the scintillation crystal output, and thus can cause artifacts in the resulting image of the object.

To, for example, reduce the effects of scattered x-rays, scatter collimators can be disposed between the object of interest and the detector array. Such collimators can be constructed of x-ray absorbent material and can be positioned so that scattered x-rays are substantially absorbed before impinging upon the detector array. Such scatter collimators can be properly aligned with both the x-ray source and the detector elements so that substantially only straight path x-rays impinge on the detector elements. Also, such scatter collimators can shield from x-ray radiation damage certain detector elements that can be sensitive at certain locations, such as the detector element edges.

Certain exemplary embodiments of a scatter collimator of the present invention can include a plurality of substantially parallel attenuating blades and a plurality of substantially parallel attenuating wires located within a housing. In certain exemplary embodiments, the attenuating blades, and thus the openings between adjacent attenuating blades, can be oriented substantially on a radial line emanating from the x-ray source. That is, each blade and opening can be focally aligned. The blades also can be radially aligned with the x-ray source. That is, each blade can be equidistant from the x-ray source. Scattered x-rays, that is, x-rays diverted from radial lines, can be attenuated by the blades. The attenuating wires can be oriented substantially perpendicular to the blades. The wires and blades thus can form a two-dimensional shielding grid for attenuating scattered x-rays and shielding the detector array.

Depending on the embodiment, the scatter collimator can include blades and wires, open air cells, and/or encapsulated cells. Certain exemplary embodiments can be fabricated as a true cross grid having septa in both radial and axial directions. The cross-grid structure can be aligned in the radial and axial directions or it can be rotated.

Depending on the grid design, it might not be practical and/or possible to remove the mold from the cast grid because of its shape or size, e.g., if very thin septa or severe undercuts are involved. In such cases, a material with a low x-ray absorptivity can be used for the mold and the final grid can be left encapsulated within the mold. Materials used for encapsulation can include, but are not limited to, polyurethanes, acrylics, foam, plastics etc.

Because certain exemplary embodiments of the present invention can utilize photolithography in creating the laminated mold, great flexibility can be possible in designing the shape of the open cells. Thus, round, square, hexagonal, and/or other shapes can be incorporated. Furthermore, the cells do not all need to be identical (a "redundant pattern"). Instead, they can vary in size, shape, and/or location ("non-redundant" pattern) as desired by the designer. In addition, because of the precision stack lamination of individual layers that can be employed in fabricating the master, the cell shapes can vary in the third dimension, potentially resulting in focused, tapered, and/or other shaped sidewalls going through the cell.

Because the cell shape can vary in the third dimension (i.e. going through the cell), the septa wall shape can also vary. For example, the septa can have straight, tapered, focused, bulging, and/or other possible shapes. Furthermore, the septa do not all need to be identical (a "redundant pattern"). Instead, they can vary in cross-sectional shape ("non-redundant" pattern) as desired by the designer.

Certain exemplary embodiments of the present invention can provide a collimator or section of a collimator as a single cast piece, which can be inherently stronger than either a laminated structure or an assembly of precisely machined individual pieces. Such a cast collimator can be designed to withstand any mechanical damage from the significant g-forces involved in the gantry structure that can rotate as fast as 4 revolutions per second. Furthermore, such a cast structure can be substantially physically stable with respect to the alignment between collimator cells and detector elements.

Some exemplary embodiments of the present invention can provide a collimator or section of a collimator as a single cast collimator in which cells and/or cell walls can be focused in the radial direction, and/or in which cells and/or cells walls can be accurately aligned in the axial direction.

Conversely, certain exemplary embodiments of the present invention can provide a collimator or section of a collimator as a single cast collimator in which cells and/or cell walls can be focused (by stacking layers having slightly offset openings) in the axial direction, and/or in which cells and/or cells walls can be curved (and focused) in the radial direction.

Exemplary embodiments of the present invention can utilize any of a wide number of different materials to fabricate the scatter collimator. A specific application can result in any of the following materials being most appropriate, depending on, for example, the net density and the cell and septa size requirements. Lead or lead alloy alone can offer a density of 9-11 grams per cc;

- Lead alloy can be loaded with a dense composite (e.g., tungsten, tantalum, and/or gold, etc.) powder to form a composite having a density of 12-15 grams per cc;
- Polymer can be loaded with a dense composite (e.g., lead, tungsten, tantalum, and/or gold, etc.) powder to form a composite having a density of 8-9 grams per cc;
- The cast grid made of lead alloy or any of the above combinations can be encapsulated in a low density polymer such that the transmission is minimally affected but scatter is significantly reduced.

In addition, certain embodiments of the present invention can be employed to fabricate grids and/or collimators for which the mold can be pre-loaded with dense powder, followed by alloy or polymer. Alternatively, polymer or alloy can be pre-loaded with dense powder then injected into the mold. In certain embodiments, the casting can be removed from a flexible mold. In other embodiments, the mold can be dissolved or consumed to de-mold the casting. In certain embodiments, a master can be removed layer-by-layer from rigid mold. Alternatively, the lost wax approach can be used in which the model is dissolvable wax, dissolvable PMMA, dissolvable polyurethane, dissolvable high-resolution ceramic, and/or some other dissolvable material.

The above description and examples have covered a number of aspects of certain exemplary embodiments of the invention including, for example, cell size and shape, different materials and densities, planar and non-planar orientations, and focused and unfocused collimators.

Additional Embodiments

Nuclear Medicine (SPECT) Collimator and Detector Array

Certain embodiments of the present invention can be used to fabricate structures useful for nuclear medicine. For example, collimators used in nuclear medicine, including pinhole, parallel-hole, diverging, and converging collimators, can be fabricated according to one or more exemplary methods of the present invention.

As another example, exemplary methods of the present invention can be used to fabricate high precision, high attenuation collimators with design flexibility for hole-format, which can improve the performance of pixelated gamma detectors.

Figure 47:
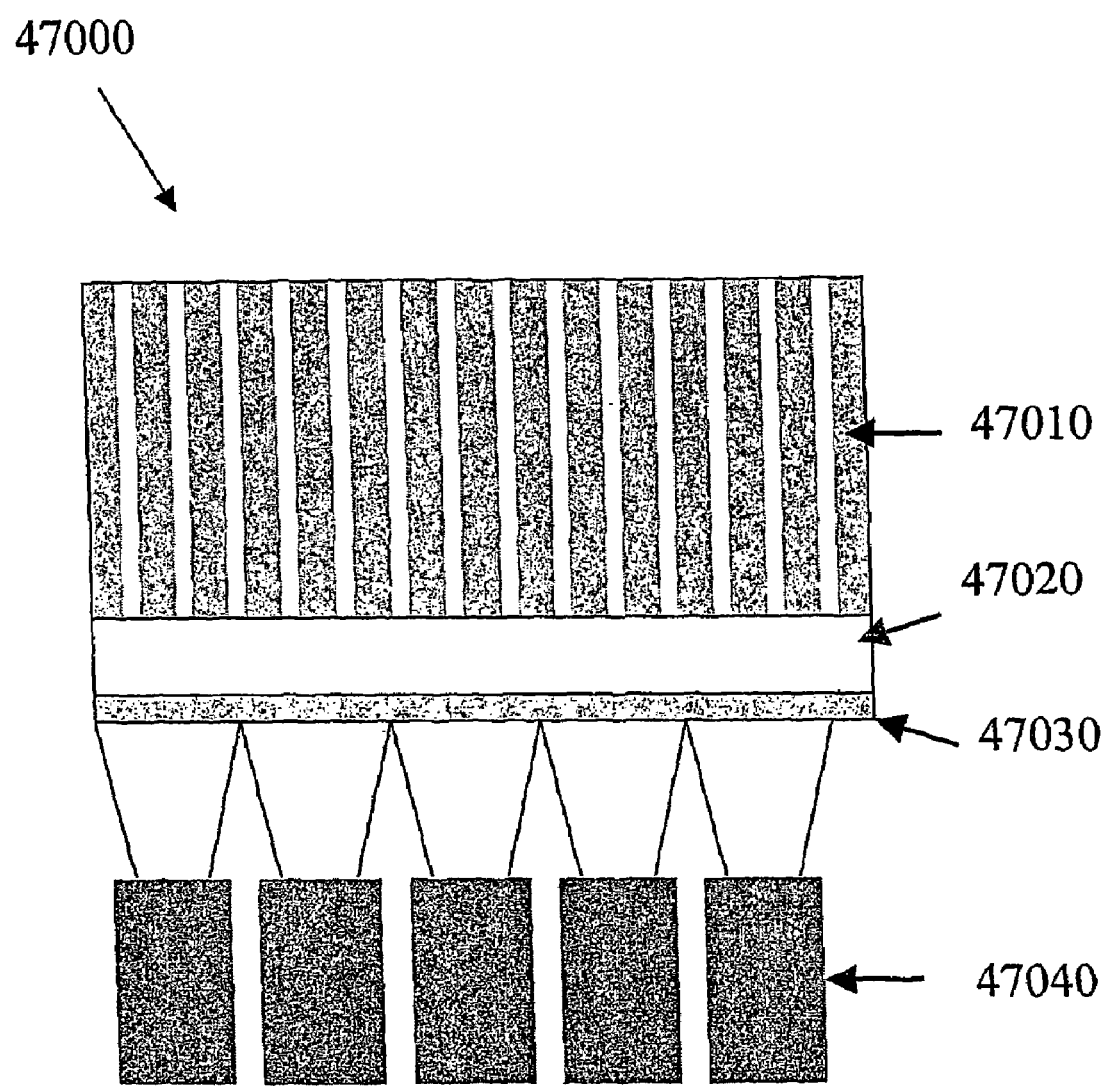
FIG. 47 is an assembly view of components of an exemplary pixelated gamma camera of the present invention.

Certain exemplary embodiments of certain casting techniques of the present invention can be applied to the fabrication of other components in detector systems. FIG. 47 is an assembly view of components of a typical pixelated gamma camera. Embodiments of certain casting techniques of the present invention can be used to produce collimator 47010, scintillator crystals segmentation structure 47020, and optical interface 47030 between scintillator array (not visible) and photo-multiplier tubes 47040.

In an exemplary embodiment, collimator 47010 can be fabricated from lead, scintillator crystals segmentation structure 47020 can be fabricated from a ceramic, and optical interface 47030 can be fabricated from acrylic.

In certain exemplary embodiments, through the use of a common fabrication process, two or more of these components can be made to the same precision and/or positional accuracy. Moreover, two or more of these components can be designed to optimize and/or manage seams and/or dead spaces between elements, thereby potentially improving detector efficiency for a given choice of spatial resolution. For example, in a pixelated camera with non-matched detector and collimator, if the detector's open area fraction (the fraction of the detector surface that is made up of converter rather than inter-converter gap) is 0.75, and the collimator's open area fraction (the fraction of the collimator surface that is hole rather than septum) is 0.75, the overall open area fraction is approximately $(0.75)=0.56$. For a similar camera in which the collimator holes are directly aligned with the pixel converters, the open area fraction is 0.75, giving a 33% increase in detection efficiency without reduction in spatial resolution.

Certain embodiments of the present invention can provide parallel hole collimators and/or collimators having non-parallel holes, such as fan beam, cone beam, and/or slant hole collimators. Because certain embodiments of the present invention use photolithography in creating the master, flexibility is possible in designing the shape, spacing, and/or location of the open cells. For example, round, square, hexagonal, or other shapes can be incorporated. In addition, because certain embodiments of the present invention use precision stack lamination of individual layers to fabricate a laminated mold, the cell shapes can vary in the third dimension, resulting in focused, tapered, and/or other shaped sidewalls going through the cell. Furthermore, the cells do not all need to be identical ("redundant"). Instead, they can vary in size, shape or location ("non-redundant") as desired by the designer, which in some circumstances can compensate for edge effects. Also, because a flexible mold can be used with certain embodiments of the present invention, collimators having non-planar surfaces can be fabricated. In some cases, both surfaces are non-planar. However, certain embodiments of the present invention also allow one or more surfaces to be planar and others non-planar if desired.

Certain embodiments of the present invention can fabricate a collimator, or section of a collimator, as a single cast piece, which can make the collimator less susceptible to mechanical damage, more structurally stable, and/or allow more accurate alignment of the collimator with the detector.

Certain embodiments of the present invention can utilize any of a number of different materials to fabricate a collimator or other component of an imaging system. A specific application could result in any of the following materials being chosen, depending, in the case of a collimator, on the net density and the cell and septa size requirements:

- Lead or lead alloy alone can offer a density of 9-11 grams per cc
- Polymer can be loaded with tungsten powder to form a composite having a density comparable to lead or lead alloys
- Polymer can also be combined with other dense powder composites such as tantalum or gold to yield a density comparable to lead or lead alloys
- Polymer can be combined with two or more dense powders to form a composite having a density comparable to lead or lead alloys
- Lead alloy can be loaded with tungsten powder to form a composite having a density of 12-15 grams per cc
- Lead alloy can be loaded with another dense composites (tantalum, gold, other) to form a composite having a density of 12-15 grams per cc
- Lead alloy can be combined with two or more dense powders to form composites having a density of 12-15 grams per cc (atomic number and attenuation)
- The cast grid made of lead alloy or any of the above combinations can be encapsulated in a low-density material such that the transmission is minimally affected but scatter is reduced.

Thus, depending on the specific application, certain embodiments of the present invention can create any of a wide range of densities for the cast parts. For example, by adding tungsten (or other very dense powders) to lead alloys, net densities greater than that of lead can be achieved. In certain situations, the use of dense particles can provide high "z" properties (a measure of radiation absorption). For certain embodiments of the present invention, as radiation absorption improves, finer septa walls can be made, which can increase imaging resolution and/or efficiency.

In addition, certain embodiments of the present invention can be employed to fabricate grids and/or collimators for which the mold can be pre-loaded with dense powder, followed by alloy or polymer. Alternatively, polymer or alloy can be pre-loaded with dense powder then injected into the mold. In certain embodiments, the casting can be removed from a flexible mold. In other embodiments, the mold can be dissolved or consumed to de-mold the casting. In certain embodiments, a master can be removed layer-by-layer from rigid mold. Alternatively, the lost wax approach can be used in which the model is dissolvable wax, dissolvable PMMA, dissolvable polyurethane, dissolvable high-resolution ceramic, and/or some other dissolvable material.

With certain embodiments of the present invention, the stack-laminated master does not need to embody the net density of the final grid. Instead, it can have approximately the same mechanical shape and size. Similarly, the final grid can be cast from relatively low cost materials such as lead alloys or polymers. Furthermore, these final grids can be loaded with tungsten or other dense powders. As discussed previously, using certain embodiments of the invention, multiple molds can be made from a single master and multiple grids can be cast at a time, if desired. Such an approach can lead to consistency of dimensions and/or geometries of the molds and/or grids.

Because of the inherent precision of the lithographic process, certain embodiments of the present invention can prevent and/or minimize assembly build up error, including error buildup across the surface of the grid and/or assembly buildup error as can occur in collimators in which each grid is individually assembled from photo-etched layers. In addition, process errors can be compensated for in designing the laminated mold.

Example 6

Lead Collimator for Gamma Camera (Nuclear Medicine Application)

Step 1: Creating the laminated mold: In this exemplary process, 0.05 mm thick copper foils were chemically etched and then laminated together using a metal-to-metal brazing process, for producing a laminated mold. Photo-masks were configured with a 2.0×2.0 millimeter square open cell, with a 0.170 mm septal wall separating the cells. The cells were arrayed having 10 rows and 10 columns, with a 2 mm border around the cell array. Photo-masks were produced to the same specifications, by the same vendor as those described in example 1, step 1.

Figure 42A:
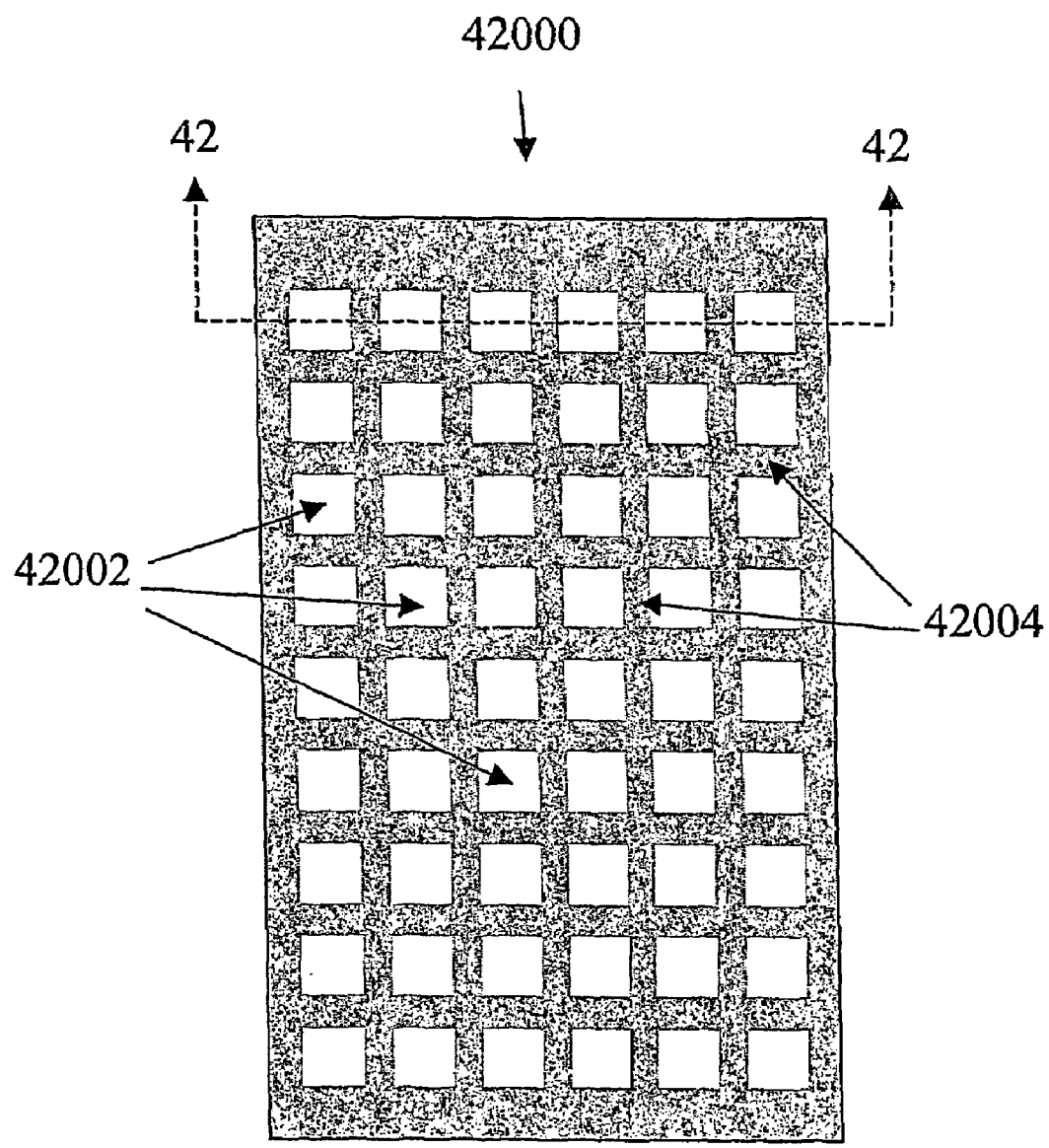
FIG. 42A is a top view of an exemplary laminated stack of the present invention.
Figure 42B:
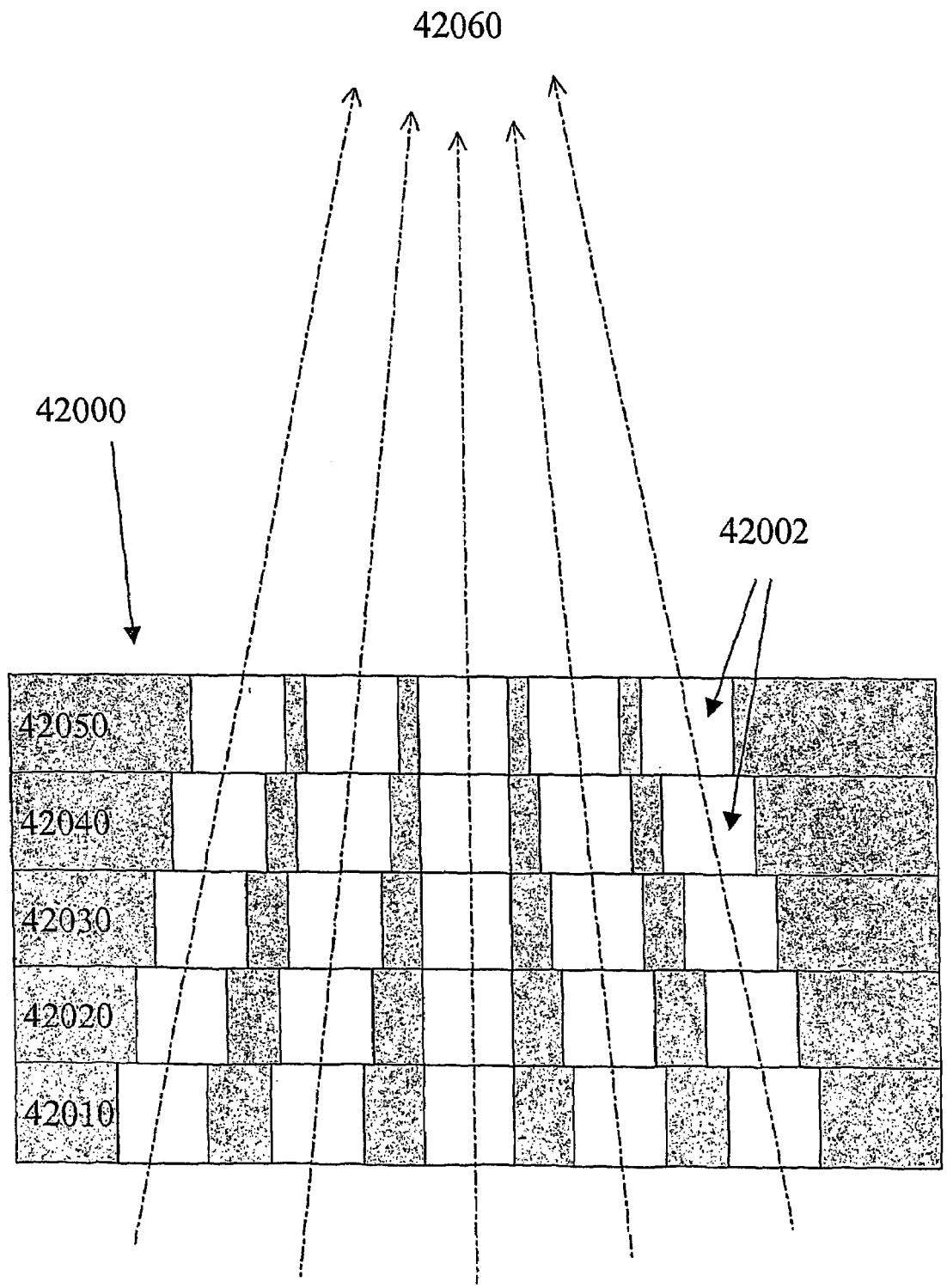
FIG. 42B is a cross-sectional view, taken at section lines 42-42 of FIG. 42A, of an exemplary laminated stack of the present invention.

The layers were designed so that the cell placement was identical from layer to layer, which when assembled, produced a parallel cross-sectional shape. FIG. 42A is a top view of an x-ray grid 42000 having an array of cells 42002 separated by septal walls 42004. FIG. 42B is a cross-sectional view of x-ray grid 42000 taken along section lines 42-42 of FIG. 42B showing that the placement of cells 42002 can also be dissimilar from layer to layer 42010-42050, so that when assembled, cells 42002 are focused specifically to a point source 42060 at a known distance from x-ray grid 42000.

The total number of layers in the stack lamination defined the thickness of the casting mold and final cast grid. The final thickness of the lamination was specified at 0.118 inches, which required 57 layers of copper foil, leaving a total thickness amount of 0.00007 inches between each layer for a braze material. The layers were processed by Tech Etch of Plymouth Mass., using standard photo-etching techniques and were etched in such a way that the cross-sectional shape of the etched walls were perpendicular to the top and bottom surfaces of the foil (commonly referred to as straight sidewalls).

The method chosen to bond the grid layers together was a metal-to-metal brazing technique described earlier in detail as one of two exemplary methods of bonding layers together (eutectic braze alloy). The brazed lamination was then electro-plated with a coating of hard nickel, also described earlier.

Step 2: Creating a derived mold: An RTV mold was made from the stack laminated mold from step 1. Silastic® M RTV Silicone Rubber was chosen as the base material for the derived mold. This particular material was used to demonstrate the resolution capability, release properties, multiple castings, and dimensional repeatability of the derived mold from the laminated mold. Silastic M has the hardest durometer of the Silastic® family of mold making materials. The derived mold was configured as an open face mold.

The fixture used to create the derived casting mold is shown in FIG. 32 and was comprised of a precision machined aluminum ring 32010, precision ground glass plates 32020 and 32030, rubber gaskets 32040 and 32050, and the laminated mold 32060. The base of the fixture 32020 was a 5 inch square of 1 inch thick plexiglass. On the top surface of the plexiglass base was a 1" thick, 3 inch diameter glass substrate 32030. The base and the glass substrate were separated by a 1/16 inch thick, 4.5 inch diameter rubber gasket 32040. An additional 3.0 inch rubber gasket 32050 was placed on the top surface of the glass substrate 32030. The rubber gaskets helped prevent unwanted flashing of molten material when casting. The laminated mold 32060 was placed on the top gasket.

The shape and thickness of the glass created the entrance area where the casting material was poured into the mold. The material formed in this cavity was referred to as a controlled backing. It served as a release aid for the final casting, and could later be removed from the casting in a final machining process. A precision machined aluminum ring 32010 having a 4.5 inch outside diameter and a 4 inch inside diameter was placed over the master subassembly and interfaced with the lower 4.5 inch diameter rubber gasket.

As illustrated in FIG. 32, the height of the ring was configured so that the distance from the top surface of the master to the top of the ring was twice the distance from the base of the fixture to the top of the laminated mold. The additional height allowed the RTV material to rise up during the degassing process. The ring portion of the fixture assembly was used to locate the pouring of the mold material into the assembly, captivate the material during the curing process, and provide an air escape while the mold material was degassed using vacuum. The fixture was configured in such a way that all sides surrounding the laminated mold were equal and common, in order to limit the effects or stresses put on the lamination from the mold material.

The Silastic® M RTV Silicone Rubber used for the mold fabrication was prepared in accordance with the manufacturer's recommendations, using the process described earlier in example 1, step 2.

The laminated mold was characterized, before and after the mold-making process, by measuring the average pitch distance of the cells, the septal wall widths, overall distance of the open grid area, and the finished thickness of the part. These dimensions were also measured on the derived casting mold and compared with the laminated mold before and after the mold-making process. The following chart lists the dimensions of the lamination before and after the mold-making and the same dimensions of the derived RTV mold. All dimensions were taken using a Nikon MM-11 measuring scope at 200× magnification. These dimensions demonstrated the survivability of the master and the dimensional repeatability of the mold.

| Grid Feature | Master Lamination (before mold-making) | RTV Mold Silastic ® M | Master Lamination (after mold-making) |
|---|---|---|---|
| Septal Wall Width (mm) | 0.170 | 0.161 | 0.170 |
| Cell Width (mm) | 2.000 × 2.000 | 2.010 × 2.010 | 2.000 × 2.000 |
| Cell Pitch (mm) | 2.170 × 2.170 | 2.171 × 2.171 | 2.170 × 2.170 |
| Pattern area (mm) | 21.530 × 21.530 | 21.549 × 21.549 | 21.530 × 21.530 |
| Thickness (mm) | 2.862 | 2.833 | 2.862 |

Figure 43:
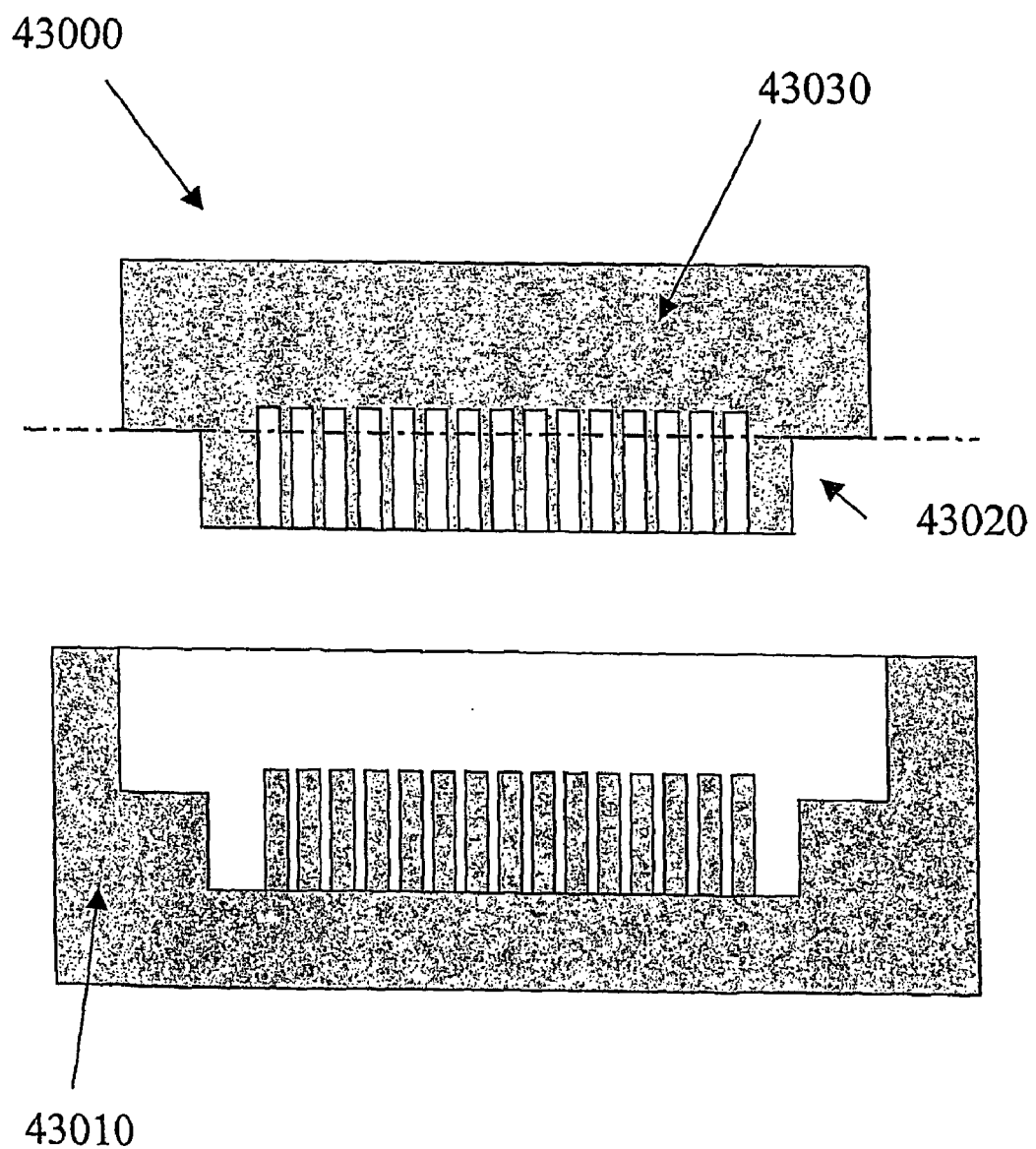
FIG. 43 is side view of an exemplary mold and casting of the present invention.

Step 3: Casting the final collimator: A fine-featured lead collimator was produced from the derived RTV silicone mold described in step 2. FIG. 43 is a side view of an assembly 43000 that includes an open face mold 43010 that was used to produce a casting 43020 from CERROBASE™ alloy. Casting 43020 was dimensionally measured and compared to the laminated mold 43010. The backing 43030 of casting 43020 was 6 millimeters in thickness and was removed using a machining process.

| Grid Features | Master Lamination | Cast Collimator |
|---|---|---|
| Septal Wall Width (mm) | 0.170 | 0.165 |
| Cell Width (mm) | 2.000 × 2.000 | 2.005 × 2.005 |
| Cell Pitch (mm) | 2.170 × 2.170 | 2.170 × 2.170 |

The first step of the casting process was to pre-heat the derived RTV mold to a temperature of 275 degrees F., which was 20 degrees above the melting point of the CERROBASE™ alloy. The mold was placed on a heated aluminum substrate, which maintained the mold at approximately 275 degrees F. when it was placed in the vacuum bell jar.

In certain casting procedures, the material can be forced into the mold in a rapid fashion, and cooled and removed quickly. In this case, the casting process was somewhat slowed in order to fully fill and evacuate the air from the complex cavity geometry of the mold. The CERROBASE™ was then heated in an electric melting pot to a temperature of 400 degrees F., which melted the alloy sufficiently above its melt point to remain molten during the casting process.

The next step was to pour the molten alloy into the mold, in such a way as to aid in the displacement of any air in the cavity. This was accomplished by tilting the mold at a slight angle and beginning the pour at the lowest point in the cavity section of the mold. It was found that if the mold was placed in a flat orientation while pouring the molten alloy, significant amounts of air were trapped, creating problems in the degassing phase of the process. Instead, once the mold was sufficiently filled with the molten alloy, the mold was slightly vibrated or tapped in order to expel the largest pockets of air. The mold, on the heated aluminum substrate, was then placed in the vacuum bell jar, pumped down to atmosphere of 25-28 inches of mercury for 2 minutes, which was sufficient time to evacuate any remaining air pockets. The mold was then removed from the vacuum bell jar and submersed in a quenching tank filled with water cooled to a temperature of 50 degrees F. The rapid quench produced a fine crystalline grain structure when the casting material solidified. The casting was then removed from the flexible mold by grasping the backing 43030, by mechanical means or by hand, and breaking the casting free of the mold using an even rotational force, releasing the casting gradually from the mold.

The final process step was removing the backing 43030 from the attached surface of the grid casting 43020 to the line shown in FIG. 43. Prior to removing the backing, the grid structure of the final casting 43020 was filled or potted with a machineable wax, which provided the structural integrity needed to machine the backing without distorting the fine walls of the grid casting. The wax was sold under the product name MASTER™ Water Soluble Wax by the Kindt-Collins Corporation, of Cleveland, Ohio. The wax was melted at a temperature of 160-180 degrees F., and poured into the open cells of the cast grid. Using the same technique described above, the wax potted casting was placed in vacuum bell jar and air evacuated before being cooled. The wax was cooled to room temperature and was then ready for the machining of the backing.

A conventional surface grinder was used to first rough cut the backing from the lead alloy casting. The remaining casting was then placed on a lapping machine and lapped on the non-backing side of the casting using a fine abrasive compound and lapping wheel. The non-backing side of the casting was lapped first so that the surface was flat and parallel to within 0.010-0.015 millimeters to the adjacent cast grid cells. The rough-cut backing surface was then lapped using the same abrasive wheel and compound so that it was flat and parallel to within 0.100-0.015 millimeters of the non-backing side of the casting. A thickness of 2.750 millimeters was targeted as the final casting thickness. Upon completion of the lapping process, the casting was placed in an acid solution, comprised of 5% dilute HCL and water, with mild agitation until the wax was fully dissolved from the cells of the casting.

In an alternative embodiment, individual castings could also be stacked, aligned, and/or bonded to achieve thicker, higher aspect ratio collimators. Such collimators, potentially having a thicknesses measured in centimeters, can be used in nuclear medicine.

Example 7

Non-Planar Collimator

A non-planar collimator can have several applications, such as, for example, in a CT environment. To create such an example of such a collimator, the following process was followed:

Step 1: Creating a laminated mold: For this example, a laminated mold was designed and fabricated using the same process and vendors described in Example 1, step 1. The laminated mold was designed to serve as the basis for a derived non-planar casting mold. The laminated mold was designed and fabricated with outside dimensions of 73.66 mm×46.66 mm, a 5 mm border around a grid area having 52×18 open cell array. The cells were 1 mm×1.980 mm separated by 0.203 septal walls.

The layers for the laminated mold were bonded using the same process described in Example 1, step 1 (thermo-cured epoxy). The dimensions of the laminated mold were specified to represent a typical collimator for CT x-ray scanning. Silastic® J RTV Silicone Rubber was chosen as a base material to create a derived non-planar casting mold because of its durometer which allowed it to more easily be formed into a non-planar configuration. The laminated mold and fixture was configured as an open face mold.

Figure 44:
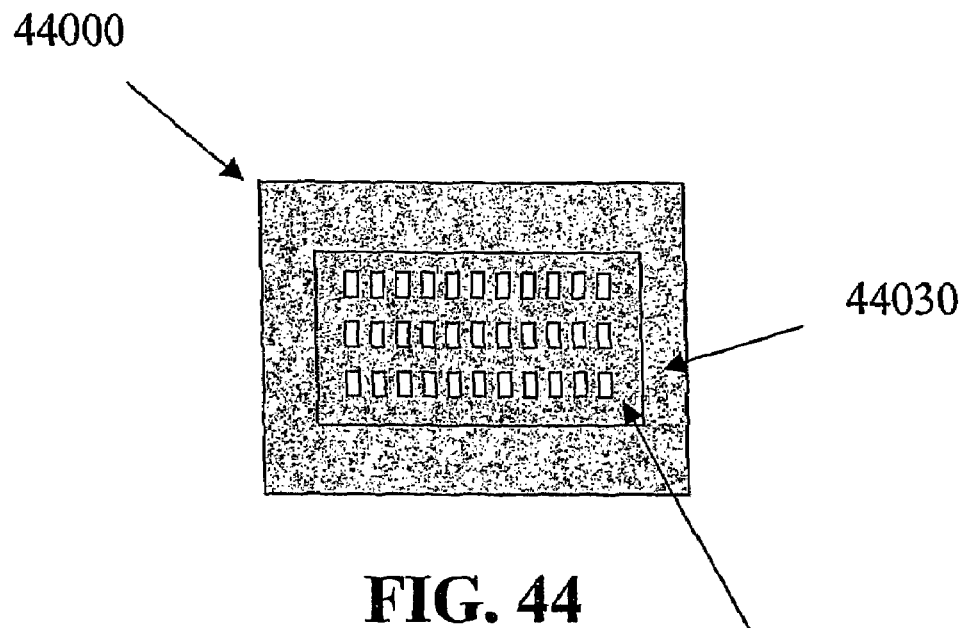
FIG. 44 is a top view of an exemplary casting fixture of the present invention.
Figure 45:
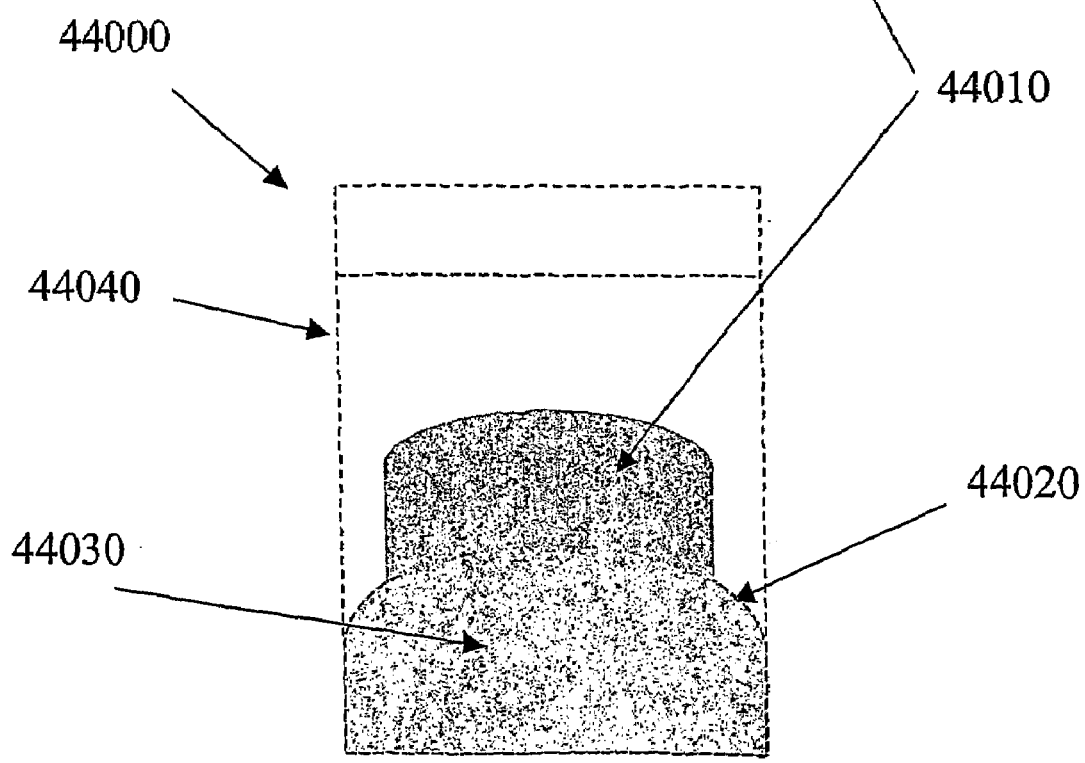
FIG. 45 is a front view of the exemplary casting fixture of FIG. 44.

Step 2: Creating a derived non-planar mold: Silastic® J RTV Silicone Rubber was used for the derived mold fabrication and was prepared in accordance with the manufacturers recommendations, using the process described earlier in example 1, step 2. FIG. 44 is a top view of casting assembly 44000. FIG. 45 is a side view of casting assembly 44000.

The derived RTV mold 44010 was then formed into a non-planar configuration as shown in FIG. 45. The surface 44020 of casting fixture base 44030 defined a 1-meter radius arc to which mold 44010 was attached. A 1-meter radius was chosen because it is a common distance from the x-ray tube to the collimator in a CT scanner. Mold 44010 was fastened to the convex surface 44020 of casting base 44030 with a high temperature epoxy adhesive. A pour frame 44040 was placed around casting fixture base 44030. Pour frame 44040 had an open top to allow pouring the casting material to a desired fill level and to allow evacuating the air from the casting material.

The laminated mold was characterized, before and after producing the derived non-planar mold, by measuring the average pitch distance of the cells, the septal wall widths, overall distance of the open grid area, and the finished thickness of the part. These dimensions were also measured on the derived non-planar mold and compared with the master before and after the mold-making process. The following chart lists the dimensions of the master lamination before and after the mold-making and the same dimensions of the RTV mold in the planar state and curved state. All dimensions are in millimeters and were taken using a Nikon MM-11 measuring scope at 200× magnification.

| Grid Features | Master Lamination (before mold-making) | RTV Mold (planar) Silastic® J | RTV Mold (curved) Silastic® J |
| --- | --- | --- | --- |
| Septal Wall | 0.203 | 0.183 | 0.193* |
| Cell Width | 1.980 × 1.000 | 2.000 × 1.020 | 2.000 × 1.020 |
| Cell Pitch | 2.183 × 1.203 | 2.183 × 1.203 | 2.183 × 1.213 |
| Pattern area | 39.091 × 62.353 | 39.111 × 62.373 | 39.111 × 62.883 |
| Thickness | 7.620 | 7.544 | 7.544 |

*measured in the direction of curvature.

Step 3: Casting a non-planar collimator: The derived non-planar RTV mold described in step 2, was used to create castings. Using the derived non-planar mold, the castings were produced from CERROBASE™ alloy and were dimensionally measured and compared to the laminated mold.

| Grid Features | Master Lamination | Cast Collimator |
| --- | --- | --- |
| Septal Wall Width (mm) | 0.203 | 0.197* |
| Cell Width (mm) | 1.000 × 1.980 | 1.006 × 1.986 |
| Cell Pitch (mm) | 1.203 × 2.183 | 1.203 × 2.183 |

*measured in the direction of curvature.

The process used to fill the derived non-planar mold with the casting alloy and the de-molding of the casting was the same process described in Example 6.

The final process step included the removal of the backing from the grid casting. A wire EDM (electrode discharge machining) process was found to be the most effective way to remove the backing from the casting, primarily due to the curved configuration of the casting. The wire EDM process used an electrically charged wire to burn or cut through the casting material, while putting no physical forces on the parts. In this case, a fine 0.003 inch molybdenum wire was used to cut the part, at a cutting speed of 1 linear inch per minute. This EDM configuration was chosen to limit the amount of recast material left behind on the cut surface of the part, leaving the finished septal walls with a smooth surface finish. The casting was fixtured and orientated so that the radial cutting of the backing was held parallel to the curved surface of the casting, which was a 1 meter radius.

Example 8

Mammography Scatter Reduction Grid

Another exemplary application of embodiments of the present invention is the fabrication of a mammography scatter reduction grid. In this example, a derived clear urethane mold for a fine-featured focused grid was made using a photo-etched stack lamination for the master model. For making this mold, the master was designed and fabricated using the lamination process detailed in Example 7. A clear urethane casting material was chosen as an example of a cast grid in which the mold was left intact with the casting as an integral part of the grid structure. This provided added strength and eliminated the need for a fragile or angled casting to be removed from the mold.

Figure 46:
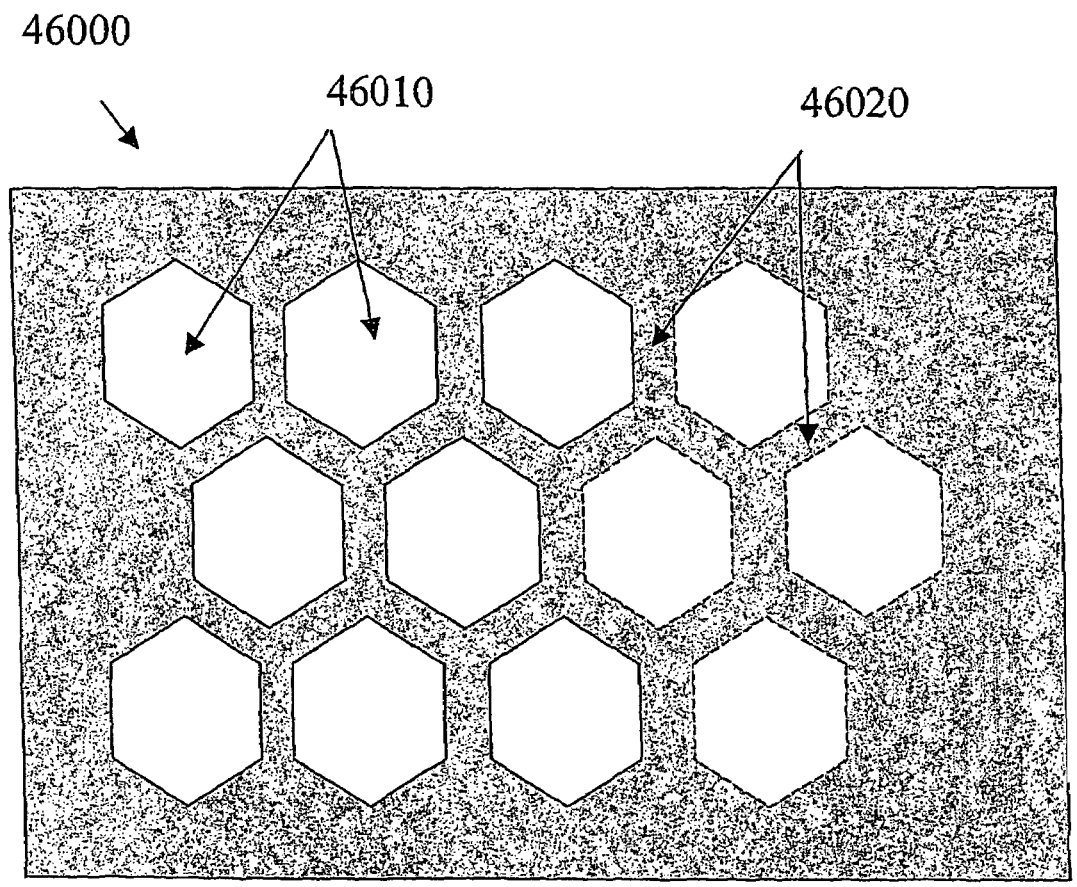
FIG. 46 is a top view of a portion of an exemplary grid pattern of the present invention.

Step 1: Creating a laminated mold: The laminated mold was fabricated from photo-etched layers of copper. The mold was designed to have a 63 mm outside diameter, a 5 mm border around the outside of the part, and a focused 53 mm grid area. FIG. 46 is a top view of a grid area 46000, which was comprised of hexagonal cells 46010 that were 0.445 mm wide, separated by 0.038 mm septal walls 46020. The cells were focused from the center of the grid pattern to a focal point of 60 centimeters, similar to that shown in FIG. 42B. The grid was made from 35 layers of 0.050 mm thick stainless steel, which when assembled created a 4:1 grid ratio. Each grid layer utilized a separate photo-mask in which the cells are arrayed out from the center of the grid pattern at a slightly larger distance from layer to layer. This created the focused geometry as shown in FIG. 42B. With this cell configuration, the final casting produced a hexagonal focused grid with a transmission of about 82%. The photo-masks and etched layers were produced using the same vendors and processes described in example 1, step 1.

Step 2: Creating a derived urethane mold: Urethane mold material was chosen for its high-resolution, low shrink factor, and low density. Because of its low density, the urethane is somewhat transparent to the transmission of x-rays. The mold material, properties, and process parameters were as described earlier in example 4, step 4.

The fixture used to create the derived urethane casting mold was the same as that described in Example 6, step 2.

Before assembling the mold fixture, the laminated mold was sprayed with a mold release, Stoner E236. The fixture was assembled as shown in FIG. 32 and heated to 125 degrees F. Then it was filled with the Water Clear urethane and processed using the same parameters described in example 4, step 4. The laminated mold was characterized, before and after making the derived mold, by measuring the average pitch distance of the cells, the septal wall widths, overall distance of the open grid area, and the finished thickness of the lamination. These dimensions were also measured on the derived urethane casting mold and compared with the lamination before and after the mold-making process. The following chart lists the dimensions of the lamination before and after the mold-making and the same dimensions of the urethane mold. All dimensions were in millimeters and were taken using a Nikon MM-11 measuring scope at 200× magnification.

| Grid Features | Master Lamination (before mold-making) | Urethane Casting System Water Clear | Master Lamination (after mold-making) |
|---|---|---|---|
| Septal Wall Width | 0.038 | 0.037 | 0.038 |
| Cell Width | 0.445 (hexagonal) | 0.446 (hexagonal) | 0.445 (hexagonal) |
| Cell Pitch | 0.483 | 0.483 | 0.483 |
| Pattern area (mm2) | 53.000 | 52.735 | 53.000 |
| Thickness | 1.750 | 1.729 | 1.750 |

Step 3: Casting the anti-scatter grid: A focused scatter reduction grid was produced by casting a lead alloy, CERROLOW-117™ alloy into the derived urethane mold described in step 2. The backing thickness of the casting was 2 millimeters and was removed using a surface grinding process.

The first step of the process was to pre-heat the derived urethane mold to a temperature of 137 degrees F., which was 20 degrees above the 117 degree melting point of the CERROLOW™ alloy. The mold was placed on a heated aluminum substrate, which maintained the mold to approximately 117 degrees F. when it was placed in the vacuum bell jar. The CERROLOW™ was then heated in an electric melting pot to a temperature of 120 degrees F., which melted the alloy sufficiently above the melt point of the material, keeping the material molten during the casting process. The process steps for filling the mold were the same as those described in Example 6, step 3.

The CERROLOW™ alloy was chosen for casting because of its high resolution capability, low melting point, and relatively high density. The urethane mold was left remaining to provide structural integrity for the fine lead alloy features. The urethane is also somewhat transparent to x-rays because of its low density (1 g/cm3) compared to the casting alloy.

Example 9

Collimator with Tungsten Loaded Alloy (Variation of Example 6)

Additional collimator samples have been produced using the same process described in Example 6 above, with the exception of the casting alloy and that it was loaded with tungsten powder prior to the casting process. The tungsten powder (KMP115) was purchased through the Kulite Tungsten Corporation of East Rutherford, N.J. CERROLOW™ alloy was loaded to raise the net density of the alloy from a density of 9.16 grams per cubic centimeter to 13 grams per cubic centimeter.

In certain radiological applications, elimination of secondary scattered radiation, also known as Compton scatter, and shielding can be an objective. The base density of the CERROLOW™ alloy can be sufficient on its own to absorb the scattered radiation, but the presence of the tungsten particles in the septal walls can increase the density and improve the scatter reduction performance of the part. The casting was dimensionally measured and compared to the laminated mold used to create the derived RTV mold.

| Grid Features | Master Lamination | Cast Collimator |
|---|---|---|
| Material | Copper | CERROLOW-117 Plus Tungsten Powder |
| Density (g/cc) | 8.96 | 12.50 |
| Septal Wall Width | 0.038 | 0.036 |
| Cell Width | 0.445 (hexagonal) | 0.447 (hexagonal) |
| Cell Pitch | 0.483 | 0.483 |

*all dimensions are in millimeters.

Prior to casting, the tungsten powder was loaded or mixed into the CERROLOW™ alloy. The first step was to super-heat the alloy to 2-3 times its melting point temperature (between 234-351 degrees F.), and to maintain this temperature. The tungsten powder, having particle sizes ranging from 1-15 microns in size, was measured by weight to 50% of the base alloy weight in a furnace crucible. A resin-based, lead-compatible soldering flux was added to the tungsten powder to serve as a wetting agent when combining the powder and the alloy. The resin flux was obtained from the Indium Corporation of America of Utica N.Y., under the name Indalloy Flux #5RMA.

The flux and the powder were heated to a temperature of 200 degrees F. and mixed together after the flux became liquid. The heated CERROLOW™ alloy and the fluxed powder then were combined and mixed using a high-shear mixer at a constant temperature of 220 degrees F. The net density of the alloy loaded with the powder was measured at 12.5 grams per cubic centimeter. The loaded alloy was molded into the derived RTV mold, and finished machined using the same process described in Example 6.

Example 10

Collimator Structure Cast from a Ceramic (Variation of Example 7)

This example demonstrates a structure that could be co-aligned with a cast collimator. The structure could be filled with detector materials, such as a scintillator, for pixilation purposes. Ceramic was chosen for high temperature processing of the scintillator materials, which are normally crystals.

Additional cast samples have been produced using a castable silica ceramic material using the same mold described in Example 7 above. The ceramic material, Rescor™-750, was obtained from the Cotronics Corporation of Brooklyn, N.Y. The ceramic material was prepared prior to casting per the manufacturer's instructions. This included mixing the ceramic powder with the supplied activator. Per the manufacturer's instructions, an additional 2% of activator was used to reduce the viscosity of the mixed casting ceramic, in order to aid in filling the fine cavity features of the mold.

The mold was filled and degassed using a similar process and the same mold and non-planar fixture as Example 7 above, covered with a thin sheet of plastic, and allowed to cure for 16 hours at room temperature. The ceramic casting then was removed from the RTV mold and post cured to a temperature of 1750 degrees F., heated at a rate of 200 degrees F. per hour. Post-curing increased the strength of the cast grid structure. The ceramic casting then was ready for the final grinding and lapping process for the removal of the backing.

Additional Fields of Use

Figure 48A:
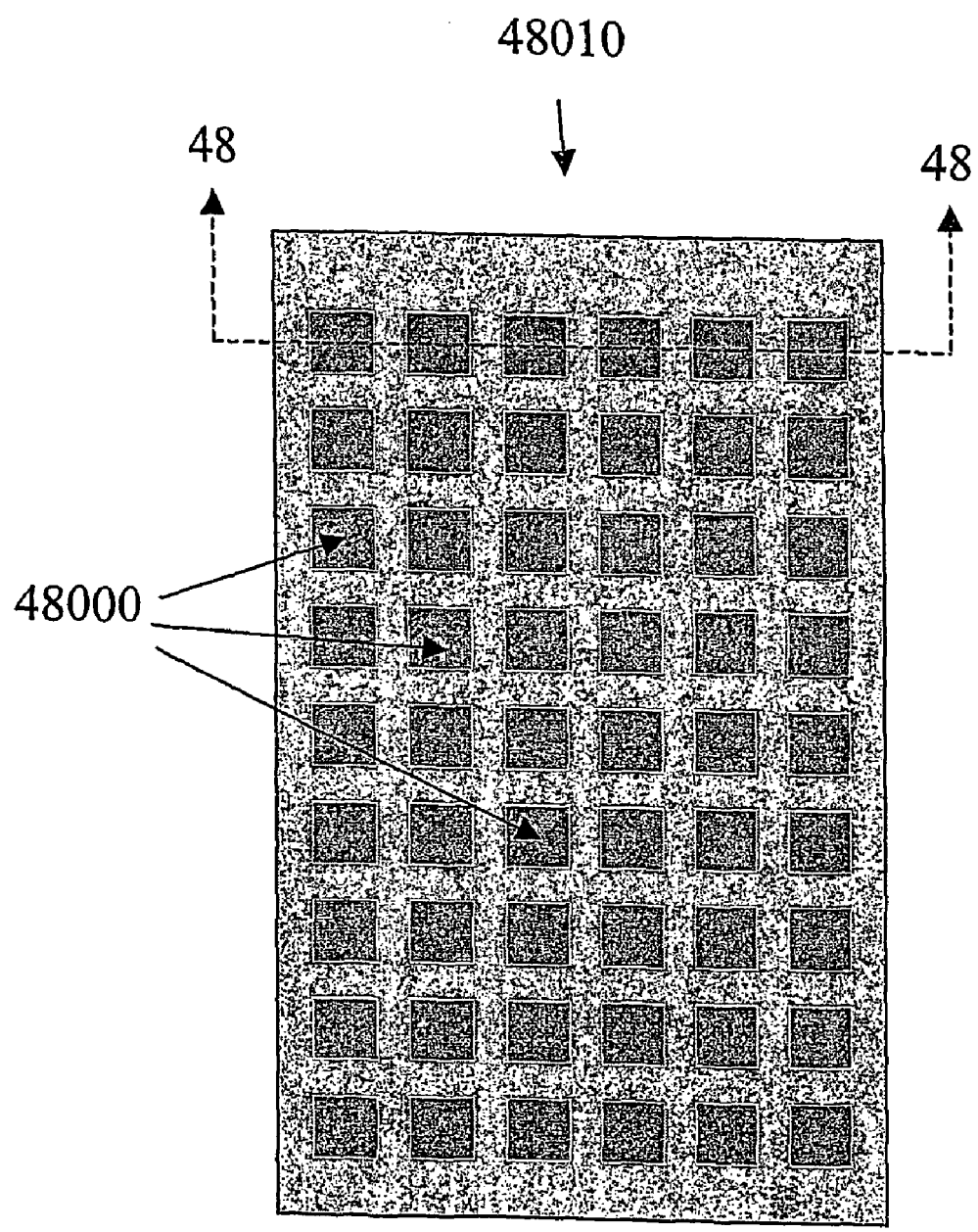
FIG. 48A is a top view of an array of generic microdevices of the present invention.
Figures 48B, 49:
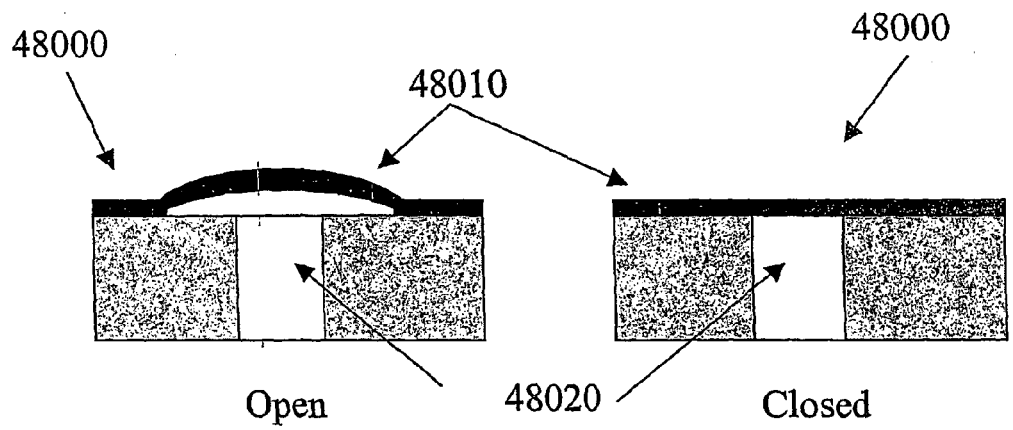
FIG. 48B is a cross-sectional view of an exemplary microdevice of the present invention, taken at section lines 48-48 of FIG. 48A, in the open state.
FIG. 49 is a cross-sectional view of the exemplary microdevice of FIG. 48B, taken at section lines 48-48 of FIG. 48A, in the closed state.

Additional fields of use and devices are contemplated for various embodiments of the invention. Among those additional fields and devices are:

Automotive Industry
  Technology Areas:
    Inertial measurement
    Micro-scale Power generation
    Pressure measurement
    Fluid dynamics
  Representative Devices:
    accelerometers
    rate sensors
    vibration sensors
    pressure sensors
    fuel cells
    fuel processors
    nozzle technology
    valves and regulators
    pumps
    filters
    relays
    actuators
    heaters Avionics Industry
  Technology Areas:
    Inertial measurement
    RF technology
    Communications
    Active structures and surfaces
  Representative Devices:
    conformable MEMS (active and passive)
    micro-satellite components
    micro-thrusters
    RF switches
    antennas
    phase shifters
    displays
    optical switches
    accelerometers
    rate sensors
    vibration sensors
    pressure sensors
    fuel cells
    fuel processors
    nozzle technology
    valves and regulators
    pumps
    filters
    relays
    actuators
    heaters Biological and Biotechnology
  Technology Areas:
    Micro-fluidics
    Microbiology
    DNA assays
    Chemical testing
    Chemical processing
    Lab-on-a-chip
    Tissue engineering
    Analytical instrumentation
    Bio-filtration
    Test and measurement
    Bio-computing
    Biomedical imaging
  Representative Devices:
    biosensors
    bioelectronic components
    reaction wells
    microtiterplates
    pin arrays
    valves
    pumps
    bio-filters
    tissue scaffolding
    cell sorting and filtration membranes Medical (Diagnostic and Therapeutic)
  Technology Areas:
    Imaging
    Interventional radiography
    Orthopedic
    Cardiac and vascular devices
    Catheter based tools and devices
    Non-invasive surgical devices
    Medical tubing
    Fasteners
    Surgical cutting tools
  Representative Devices:
    airways
    balloon catheters clips
compression bars
drainage tubes
ear plugs
hearing aids
electrosurgical hand pieces and tubing
feeding devices
balloon cuffs
wire/fluid coextrusions
lumen assemblies
infusion sleeves/test chambers
introducer tips/flexible sheaths
seals/stoppers/valves
septums
stents
shunts
membranes
electrode arrays
ultra-sound transducers
infra-red radiation sensors
radiopaque targets or markers
collimators
scatter grids
detector arrays Military
Technology Areas:
  Weapon safeing
  Arming and fusing
  Miniature analytical instruments
  Biomedical sensors
  Inertial measurement
  Distributed sensing and control
  Information technology
Representative Devices:
  MEMS fuse/safe-arm devices
  ordinance guidance and control devices
  gyroscopes
  accelerometers
  disposable sensors
  spectrometers
  active MEMS surfaces (large area)
  micro-mirror MEMS displays Telecommunications
Technology Areas:
  Optical switches
  Displays
  Adaptive optics
Representative Devices:
  micro-relays
  optical attenuators
  photonic switches
  micro-channel plates
  optical switches
  displays Microvalves Microvalves can be enabling components of many microfluidic systems that can be used in many industry segments. Microvalves are generally classified as passive or active valves, but can share similar flow characteristics through varied orifice geometries. Diaphragm microvalves can be useful in many fluidic applications. FIG. 48A is a top view of an array 48010 of generic microdevices 48000. FIG. 48B is a cross section of a particular microdevice 48000 in this instance a diaphragm microvalve, taken along section lines 48-48 of FIG. 48A, the microvalve including diaphragm 48010 and valve seat 48020, as shown in the open position.

FIG. 49 is a cross section of the diaphragm microvalve 48000, again taken along section lines 48-48 of FIG. 48A, the microvalve in the closed position.

The flow rate through diaphragm microvalve 48000 can be controlled via the geometric design of the valve seat, which is often referred to as gap resistance. The physical characteristics of the valve seat, in combination with the diaphragm, can affect flow characteristics such as fluid pressure drop, inlet and outlet pressure, flow rate, and/or valve leakage. For example, the length, width, and/or height of the valve seat can be proportional to the pressure drop across the microvalve's diaphragm. Additionally, physical characteristics of the diaphragm can influence performance parameters such as fluid flow rate, which can increase significantly with a decrease in the Young's modulus of the diaphragm material. Valve leakage also can become optimized with a decrease in the Young's modulus of the diaphragm, which can enable higher deflection forces, further optimizing the valve's overall performance and/or lifetime.

Typical microvalve features and specifications can include a valve seat: The valve seat, which is sometimes referred to as the valve chamber, can be defined by its size and the material from which it is made. Using an exemplary embodiment of a method of the present invention, the dimensions of the chamber can be as small as about 10 microns by about 10 microns if square, about 10 microns in diameter if round, etc., with a depth in the range of about 5 microns to millimeters or greater. Thus, aspect ratios of 50, 100, or 200:1 can be achieved. The inner walls of the chamber can have additional micro features and/or surfaces which can influence various parameters, such as flow resistance, Reynolds number, mixing capability, heat exchange fouling factor, thermal and/or electrical conductivity, etc.

The chamber material can be selected for application specific uses. As examples, a ceramic material can be used for high temperature gas flow, or a chemical resistant polymer can be used for chemical uses, and/or a bio-compatible polymer can be used for biological uses, to name a few. Valve chambers can be arrayed over an area to create multi-valve configurations. Each valve chamber can have complex inlet and outlet channels and/or ports to further optimize functionality and/or provide additional functionality.

Typical microvalve features and specifications can also include a diaphragm: The diaphragm can be defined by its size, shape, thickness, durometer (Young's modulus), and/or the material from which it is made. Using an exemplary embodiment of a method of the present invention, the dimensions of the diaphragm can be as small as about 25 microns by about 25 microns if square, about 25 microns in diameter if round, etc., with thickness of about 1 micron or greater. The surface of one side or both sides of the diaphragm could have micro features and/or surfaces to influence specific parameters, such as diaphragm deflection and/or flow characteristics. The diaphragm can be fabricated as a free form device that is attached to the valve in a secondary operation, and/or attached to a substrate. Diaphragms can be arrayed to accurately align to a matching array of valve chambers.

Potential performance parameters can include valve seat and diaphragm material, diaphragm deflection distance, inlet pressure, flow, and/or lifetime.

Micropumps

Figures 50, 51:
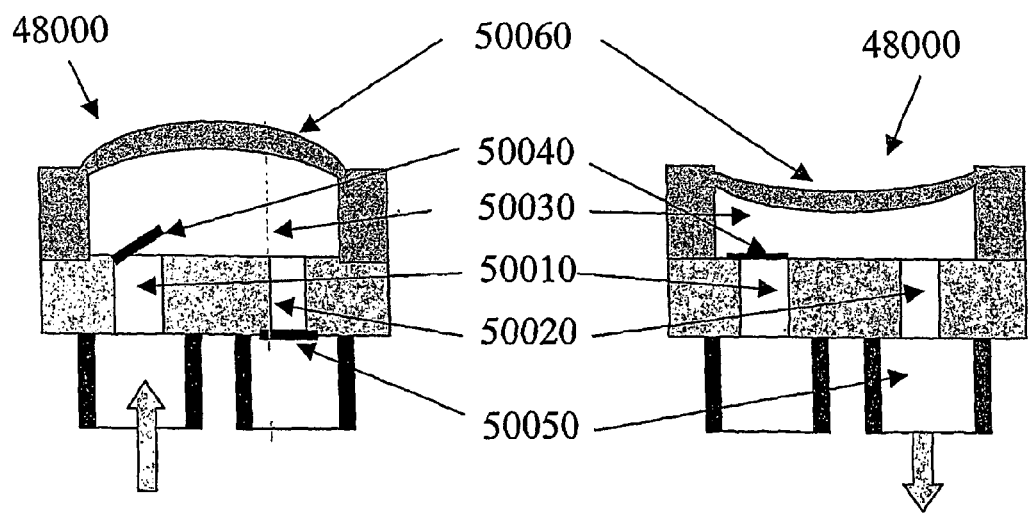

FIGS. 50 and 51 are cross-sectional views of a particular micro-device 48000, in this case a typical simplified micropump, taken along section lines 48-48 of FIG. 48A. Micropumps can be an enabling component of many microfluidic systems that can be used in many industry segments. Reciprocating diaphragm pumps are a common pump type used in micro-fluidic systems. Micropump 50000 includes two microvalves 50010 and 50020, a pump cavity 50030, valve diaphragms 50040 and 50050, and actuator diaphragm 50060.

At the initial state of pump 50000, the actuation is off, both inlet and outlet valves 50010 and 50020 are closed, and there is no fluid flow through pump 50000. Once actuator diaphragm 50060 is moved upwards, the cavity volume will be expanded causing the inside pressure to decrease, which opens inlet valve 50010 and allows the fluid to flow into and fill pump cavity 50030, as seen in FIG. 50. Then actuator diaphragm 50060 moves downward, shrinking pump cavity 50030, which increases the pressure inside cavity 50030. This pressure opens outlet valve 50020 and the fluid flows out of the pump cavity 50030 as seen in FIG. 51. By repeating the above steps, continuous fluid flow can be achieved. The actuator diaphragm can be driven using any of various drives, including pneumatic, hydraulic, mechanical, magnetic, electrical, and/or piezoelectrical, etc. drives.

Typical microvalve features and specifications can include any of the following, each of which are similar to those features and specifications described herein under Microvalves:

Valve seats
Valve actuators (diaphragm)
Cavity chamber
Actuator diaphragm

Potential performance parameters can include valve seat, chamber material, actuator diaphragm material, valve diaphragm material, deflection distance for actuator, deflection distance for valve diaphragms, inlet pressure, outlet pressure, chamber capacity, flow rate, actuator drive characteristics (pulse width, frequency, and/or power consumption, etc.), and/or lifetime.

Microwells and Microwell Arrays

Microwells can be an enabling component in many devices used for micro-electronics, micro-mechanics, micro-optics, and/or micro-fluidic systems. Precise arrays of micro-wells, potentially having hundreds to thousands of wells, can further advance functionality and process capabilities. Microwell technology can be applied to DNA micro-arrays, protein micro-arrays, drug delivery chips, microwell detectors, gas proportional counters, and/or arterial stents, etc. Fields of use can include drug discovery, genetics, proteomics, medical devices, x-ray crystallography, medical imaging, and/or bio-detection, to name a few.

For example, using exemplary embodiments of the present invention, microwells can be engineered in the third (Z) dimension to produce complex undercuts, pockets, and/or sub-cavities. Wells can also be arrayed over various size areas as redundant or non-redundant arrays. These features can include the dimensional accuracies and/or tolerances described earlier. Also, a range of surface treatments within the well structure are possible that can enhance the functionality of the well.

Examples of Microwell Applications

DNA Microarrays: Scientists can rely on DNA microarrays for several purposes, including 1) to determine gene identification, presence, and/or sequence in genotype applications by comparing the DNA on a chip; 2) to assess expression and/or activity level of genes; and/or 3) to measure levels of proteins in protein based arrays, which can be similar to DNA arrays.

DNA microarrays can track tens of thousands of reactions in parallel on a single chip or array. Such tracking is possible because each probe (a gene or shorter sequence of code) can be deposited in an assigned position within the cell array. A DNA solution, representing a DNA sample that has been chopped into constituent sequences of code, can be poured over the entire array (DNA or RNA). If any sequence of the sample matches a sequence of any probe, the two will bind, and non-binding sequences can be washed away. Because each sequence in the sample or each probe can be tagged or labeled with a fluorescent, any bound sequences will remain in the cell array and can be detected by a scanner. Once an array has been scanned, a computer program can convert the raw data into a color-coded readout.

Protein Microarrays: The design of a protein array is similar to that of a DNA chip. Hundreds to thousand of fluorescently labeled proteins can be placed in specific wells on a chip. The proteins can be deposited on the array via a pin or array of pins that are designed to draw fluidic material from a well and deposit it on the inside of the well of the array. The position and configuration of the cells on the array, the pins, and the wells are located with the accuracy needed to use high-speed pick-and-place robotics to move and align the chip over the fluidic wells. A blood sample is applied to the loaded array and scanned for bio-fluorescent reactions using a scanner.

Certain embodiments of the invention enable DNA or Protein microarrays having a potentially large number of complex 3-dimensional wells to be fabricated using any of a range of materials. For example, structures can be fabricated that combine two or more types of material in a microwell or array. Additional functionality and enhancements can be designed into a chip having an array of microwells. Wells can be produced having cavities capable of capturing accurate amounts of fluids and/or high surface-to-volume ratios. Entrance and/or exit configurations can enhance fluid deposition and/or provide visual enhancements to scanners when detecting fluorescence reactions. Very precise well locations can enable the use of pick and place robotics when translating chips over arrays of fluidic wells. Certain embodiments of the invention can include highly engineered pins and/or pin arrays that can be accurately co-aligned to well arrays on chips and/or can have features capable of efficiently capturing and/or depositing fluids in the wells.

Arterial Stents: Stents are small slotted cylindrical metal tubes that can be implanted by surgeons to prevent arterial walls from collapsing after surgery. Typical stents have diameters in the 2 to 4 millimeter range so as to fit inside an artery. After insertion of a stent, a large number of patients experience restenosis—a narrowing of the artery—because of the build-up of excess cells around the stent as part of the healing process. To minimize restenosis, techniques are emerging involving the use of radioactive elements or controlled-release chemicals that can be contained within the inner or outer walls of the stent.

Certain embodiments of the invention can provide complex 3-dimensional features that can be designed and fabricated into the inside, outside, and/or through surfaces of tubing or other generally cylindrical and/or contoured surfaces. Examples 4 and 5 teach such a fabrication technique for a 3 mm tube. Certain embodiments of the invention can allow the manufacture of complex 2-dimensional and/or 3-dimensional features through the wall of a stent. Micro surfaces and features can also be incorporated into the stent design. For example, microwells could be used to contain pharmaceutical materials. The wells could be arrayed in redundant configurations or otherwise. The stent features do not have to be machined into the stent surface one at a time, but can be applied essentially simultaneously. From a quality control perspective, features formed individually typically must be 100% inspected, whereas features produced in a batch typically do not. Furthermore, a variety of application specific materials (e.g., radio-opaque, biocompatible, biosorbable, biodissolvable, shape-memory) can be employed.

Microwell Detectors: Microwells and microwell arrays can be used in gas proportional counters of various kinds, such as for example, in x-ray crystallography, in certain astrophysical applications, and/or in medical imaging. One form of microwell detector consists of a cylindrical hole formed in a dielectric material and having a cathode surrounding the top opening and anode at the bottom of the well. Other forms can employ a point or pin anode centered in the well. The microwell detector can be filled with a gas such as Xenon and a voltage can be applied between the cathode and anode to create a relatively strong electric field. Because of the electric field, each x-ray striking an atom of the gas can initiate a chain reaction resulting in an "avalanche" of hundreds or thousands of electrons, thereby producing a signal that can be detected. This is known as a gas electron-multiplier. Individual microwell detectors may be used to detect the presence and energy level of x-rays, and if arrays of microwell detectors are employed, an image of the x-ray source can be formed. Such arrays can be configured as 2-dimensional and/or 3-dimensional arrays.

Certain embodiments of the invention can enable arrays of complex 3-dimensional wells to be fabricated and bonded or coupled to other structures such as a cathode material and anode material. It is also possible to alter the surface condition of the vertical walls of the wells, which can enhance the laminar flow of electrons in the well. A number of possible materials can be used to best meet the needs of a particular application, enhancing parameters such as conductivity, dielectrical constant, and/or density. Certain embodiments of the invention can further enable the hybridizing of microelectronics to a well array, in particular because of accurate co-alignment between the micro-electronic feature(s), and/or the structural elements of the well.

Figure 52:
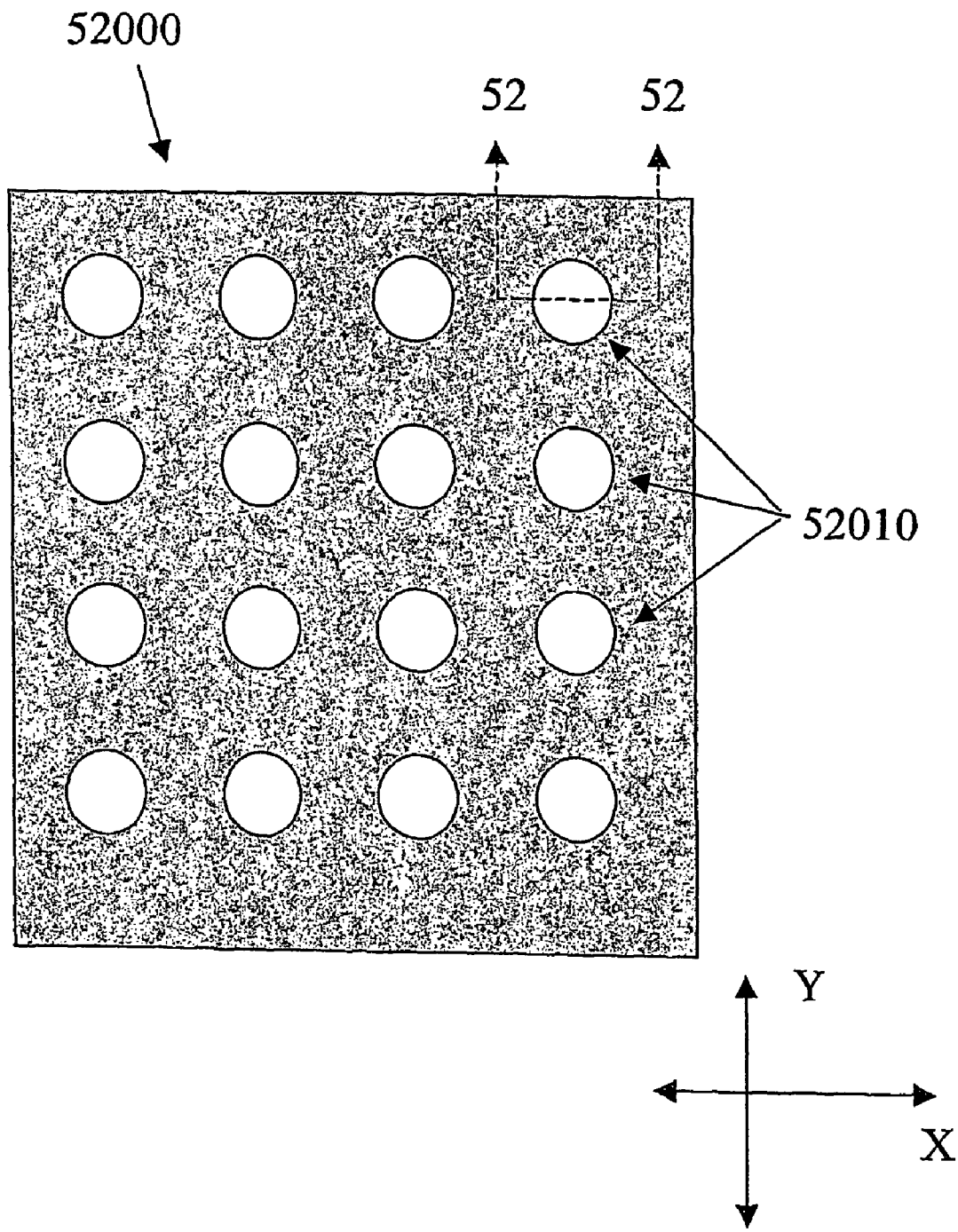
FIG. 52 is a top view of an exemplary microwell array of the present invention.

Typical Microwell Features, Specifications and Potential Performance Parameters:

FIG. 52 is a top view of an exemplary microwell array 52000, showing microwells 52010, and the X- and Y-axes. Array 52000 is shown as rectangle, but could be produced as a square, circle, or any other shape. Either of the array's dimensions as measured along the X-or Y-axes can range from 20 microns to 90 centimeters. Microwells 52010 are shown having circular perimeters, but could also be squares, rectangles, or any other shape. Array 52000 is shown having a redundant array of wells 52010, but could be produced to have non-redundant wells. The positional accuracy of wells 52010 can be accurate to the specifications described herein for producing lithographic masks. Wells can range in size from 0.5 microns to millimeters, with cross-sectional configurations as described herein.

Using certain embodiments of a method of the present invention, certain materials can be used to produce microwell arrays for specific uses. For example, a ceramic material can be used for high-temperature gas flow, a chemical resistant polymer can be used for chemical uses, and/or a bio-compatible polymer can be used for biological uses, to name a few. Specialty composite materials can enhance application specific functionality by being conductive, magnetic, flexible, hydrophilic, hydrophobic, piezoelectric, to name a few.

Using an embodiment of a method of the present invention, microwells with certain 3-dimensional cross-sectional shapes can be produced. FIG. 52 is a top view of an exemplary array 52000 of microwells 52010.

FIG. 53 is a cross-sectional view, taken at section lines 52-52 of FIG. 52, of an exemplary microwell 53000 having an entrance 53010. Entrance 53010 is shown having a tapered angle, which could be angled from 0 degrees to nearly 180 degrees. Entrance 53010 is also shown having a different surface than well area 53020. Well area 53020 can be square, round, rectangular, or any other shape. Well area 53020 can range in size from 0.5 microns to millimeters in width and can be dimensionally controlled in the Z-axis to have aspect ratios of from about 50:1 to about 100:1. As shown in FIG. 53, microwell 53000 defines microwell surfaces 53050, 53060, 53070, 53080, 53090, 53100, 53110. As also shown in FIG. 53, a cross-sectional surface 53030 is defined that intersects microwell surfaces 53050, 53060, 53070, 53080, 53090, 53100, 53110. As further shown in FIG. 53, a central area and/or layer-less volume 53040 of cross-sectional surface 53030 comprises a majority of cross-sectional surface 53030, yet does not include any of microwell surfaces 53050, 53060, 53070, 53080, 53090, 53100, 53110, which define a periphery 53120 of central area and/or layer-less volume 53040 of microwell 53000.

FIG. 54 is a cross-sectional view, taken at section lines 52-52 of FIG. 52, of an alternative exemplary microwell 54000 that defines an entrance 54010, a well 54020, and an exit 54030. Microwell 54000 can be used in applications that require fluids that are conveyed from below or above the entrance 54010 and/or exit 54030, and deposited in well 54020. Using an embodiment of a method of the present invention, microwell 54000 can be produced so that well 54020 is hydrophilic and entrance 54010 and exit 54030 are hydrophobic to, for example, enable the deposition of fluid into well 54020, and discourage the fluid deposition, retention, and/or accumulation on entrance 54010, on exit 54030, and/or on the chip's surface. For uses where microelectronic controls or chips are employed, the material surrounding and/or defining entrance 54010 and/or 54030 can be conductive or non-conductive, as required. Well 54020 can be dimensioned to accurately contain a pre-determined amount of fluid.

The shape and size of corner feature 54040 can be defined to encourage the discharge of a fluid material from a fluidic channel on a pin, when a pin is produced using any of certain embodiments of the invention. For example, pins can be produced having fluidic channels or undercuts that are positioned radially at the end of the pin. The undercuts can serve as reservoirs that increase surface area-to-volume ratios and/ or hold accurate amounts of fluids. If the undercuts are designed to be relatively flexible and larger than the opening dimension at feature 54040, fluid can be squeezed from the reservoir as the fluid passes by corner feature 54040. Entrance 54010 can have an angle that promotes the visibility of a material, such as a fluid, in well 54020. The material surrounding and/or defining well 54020 can be fabricated to have micro-surface features to increase the well's surface area-to-volume ratio.

FIG. 55 is a top view of an exemplary microwell 55000 showing a well area 55010 and sub-cavities 55020. FIG. 56 is a cross-sectional view, taken at section lines 56-56 of FIG. 55, of microwell 55000 showing well 55010 and sub-cavities 55020. Well 55010 can extend through the material that defines it, as shown in FIG. 56, or can be a closed well having a solid floor. Sub-cavities 55020 can be incorporated within a well to, for example, increase an area of the surface(s) bordering the well, a volume, and/or surface area-to-volume ratio of the well. Sub-cavities 55020 can be continuous rings as shown in FIG. 55. Alternatively, sub-cavities 55020 can be discrete pockets forming sub-wells within well 55010. Sub-cavities 55020 can be positioned on a horizontal floor or subfloor of well 55010 as shown in FIG. 55, on the vertical walls of well 55010, and/or on another surface. Sub-cavities 55020 can have circular, square, rectangular, and/or any of a variety of other cross-sectional shapes. Sub-cavities 55020 can also be positioned to provide an enhanced visual perspective of a deposited material from which could be angled from 0 degrees to nearly 180 degrees, such as an approximately perpendicular angle, so as to enhance scanning performance or resolution.

Filtration

Filtration can be an important element in many industries including medical products, food and beverage, pharmaceutical and biological, dairy, waste water treatment, chemical processing, textile, and/or water treatment, to name a few. Filters are generally classified in terms of the particle size that they can separate. Micro-filtration generally refers to separation of particles in the range of approximately 0.01 microns through 20 microns. Separation of larger particles than approximately 10-20 microns is typically referred to as particle separation. There are two common forms of filtration, cross-flow and dead-end. In cross-flow separation, a fluid stream runs parallel to a membrane of a filter while in dead-end separation, the filter is perpendicular to the fluid flow. There are a very large number of different shapes, sizes, and materials used for filtration depending on the particular application.

Certain embodiments of the invention can be filters suitable for micro-filtration and/or particle filtration applications. Certain embodiments of the invention allow fabrication of complex 2-dimensional and/or 3-dimensional filters offering redundant or non-redundant pore size, shape, and/or configuration. For example, a circular filter can have an array of redundant generally circular through-features, each through-feature having a diameter slightly smaller than a target particle size. Moreover, the through-feature can have a tapered, countersunk, and/or undercut entrance, thereby better trapping any target particle that encounters the through-feature. Further, the cylindrical walls defined by the through-feature can have channels defined therein that are designed to allow a continued and/or predetermined amount of fluid flow around a particle once the particle encounters the through-feature. The fluid flow around the particle can create eddys vortices, and/or other flow patterns that better trap the particle against the filter.

Certain embodiments of the filter can have features that allow the capture of particles of various sizes at various levels of the filter. For example, an outer layer of the filter can capture larger particles, a middle layer can capture mid-sized particles, and a final layer can capture smaller particles. There are numerous techniques for accomplishing such particle segregation, including providing through-features having tapered, stepped, and/or diminishing cross-sectional areas.

In certain embodiments, the filter can include means for detecting a pressure drop across the filter, and/or across any particular area, layer, and/or level of the filter. For example, in a filter designed to filter a gas such as air, micro pitot tubes can be fabricated into each layer of the filter (or into selected layers of the filter). Such pressure measurement devices can be used to determine the pressure drop across each layer, to detect the level of "clogging" of that layer, and/or to determine what size and/or concentration of particles are entrapped in the filter.

Further, certain embodiments of the invention allow for fabrication of filters in a wide range of materials including metals, polymers, plastics, ceramics, and/or composites thereof. In biomedical applications, for instance, a biocompatible material can be used that will allow filtration of blood or other body fluids. Using certain embodiments of the invention, filtration schemes can be engineered as planar or non-planar configurations.

Sorting

Sorting can be considered a special type of filtration in which particles, solids, and/or solids are separated by size. In biomedical applications for example, it may be desirable to sort blood or other types of cells by size and deliver different sizes to different locations. Certain embodiments of the invention can enable the fabrication of complex 3-dimensional structures that allow cells to be sorted by size (potentially in a manner similar to that discussed herein for filters) and/or for cells of different sizes to be delivered through different size micro-channels or between complex 3-dimensional structures. Structures can be material specific and on planar or non-planar surfaces.

Membranes

Membranes can offer filtration via pore sizes ranging from nanometers to a few microns in size. Membrane filtration can be used for particles in the ionic and molecular range, such as for reverse osmosis processes to desalinate water. Membranes are generally fabricated of polymers, metals, or ceramics. Micro-filtration membranes can be divided into two broad types based on their pore structure. Membranes having capillary-type pores are called screen membranes, and those having so-called tortuous-type pores are called depth membranes.

Screen membranes can have nearly perfectly round pores that can be dispersed randomly over the outer surface of the membrane. Screen membranes are generally fabricated using a nuclear track and etch process. Depth membranes offer a relatively rough surface where there appear to be openings larger than the rated size pore, however, the fluid must follow a random tortuous path deeper into the membrane to achieve their pore-size rating. Depth membranes can be fabricated of silver, various cellulosic compounds, nylon, and/or polymeric compounds.

Certain embodiments of the invention enable fabrication of membranes having complex 3-dimensional shapes, sizes, and/or configurations made of polymers, plastics, metals, and/or ceramics, etc. Furthermore, such membranes can embody redundant or non-redundant pores, and can be fabricated to be flexible, rigid, and/or non-planar depending upon the material and/or application requirements.

Although the invention has been described with reference to specific embodiments thereof, it will be understood that numerous variations, modifications and additional embodiments are possible, and accordingly, all such variations, modifications, and embodiments are to be regarded as being within the spirit and scope of the invention. Also, references specifically identified and discussed herein are incorporated by reference as if fully set forth herein.

What is claimed is:

1. A method of forming a casting, comprising:
   filling a mold having a stacked plurality of lithographically-derived micro-machined metallic foil layers with a first casting material to form a first cast product having an aspect ratio of greater than 10:1, the stacked plurality of lithographically-derived micro-machined metallic foil layers defining a protruding undercut; and demolding the first cast product from the mold, said first cast product comprising a plurality of product surfaces that define a periphery of a layer-less volume of said first cast product, a product surface from said plurality of product surfaces comprising a plurality of 3-dimensional micro-features that substantially spatially invertedly replicate a mold surface formed by said stacked plurality of metallic foil layers.

2. The method of claim 1, further comprising providing the mold.

3. The method of claim 1, further comprising, for each of the stacked plurality of lithographically-derived micro-machined layers, designing a feature associated with the layer.

4. The method of claim 1, further comprising designing a feature associated with all of the stacked plurality of lithographically-derived micro-machined layers of the mold.

5. The method of claim 1, further comprising micro-machining each of the stacked plurality of lithographically-derived micro-machined layers.

6. The method of claim 1, further comprising, for each of the stacked plurality of lithographically-derived micro-machined layers, micro-machining a feature associated with the layer.

7. The method of claim 1, further comprising micro-machining a feature associated with all of the stacked plurality of lithographically-derived micro-machined layers.

8. The method of claim 1, further comprising stacking the stacked plurality of lithographically-derived micro-machined layers.

9. The method of claim 1, further comprising aligning the stacked plurality of lithographically-derived micro-machined layers.

10. The method of claim 1, further comprising bonding the stacked plurality of lithographically-derived micro-machined layers.

11. The method of claim 1, further comprising clamping the stacked plurality of lithographically-derived micro-machined layers.

12. The method of claim 1, further comprising securing the stacked plurality of lithographically-derived micro-machined layers.

13. The method of claim 1, further comprising affixing the stacked plurality of lithographically-derived micro-machined layers.

14. The method of claim 1, further comprising fabricating the mold.

15. The method of claim 1, further comprising allowing the first casting material to solidify to form the first cast product.

16. The method of claim 1, further comprising surrounding the first cast product with a second casting material.

17. The method of claim 1, further comprising surrounding the first cast product with a second casting material and allowing the second casting material to solidify into a second cast product.

18. The method of claim 1, further comprising surrounding the first cast product with a second casting material and allowing the second casting material to solidify into a nonplanar second cast product.

19. The method of claim 1, further comprising forming the first cast product into a non-planar shape.

20. The method of claim 1, further comprising forming the first cast product into a non-planar shape and surrounding the formed first cast product with a second casting material and allowing the second casting material to solidify into a non-planar second cast product.

21. The method of claim 1, further comprising surrounding the first cast product with a second casting material and demolding a second cast product formed from the second casting material.

22. The method of claim 1, wherein the first casting material comprises a flexible polymer.

23. The method of claim 1, wherein the first casting material comprises an elastomer.

24. The method of claim 1, wherein the first casting material comprises silicone rubber.

25. The method of claim 1, wherein the stacked plurality of lithographically-derived micro-machined layers define a cavity having a protruding undercut.

26. The method of claim 1, wherein the stacked plurality of lithographically-derived micro-machined layers define a plurality of cavities therein.

27. The method of claim 1, further comprising positioning an insert into a cavity defined by the stacked plurality of lithographically-derived micro-machined layers.

28. The method of claim 1, further comprising positioning an insert into a cavity defined by the stacked plurality of lithographically-derived micro-machined layers, the insert occupying only a portion of the cavity.

29. The method of claim 1, further comprising positioning an insert into a cavity defined by the stacked plurality of lithographically-derived micro-machined layers prior to said filling the mold with the first casting material.

30. The method of claim 1, further comprising positioning a lithographically-derived micro-machined insert into a cavity defined by the stacked plurality of lithographically-derived micro-machined layers prior to said filling the mold with the first casting material.

31. The method of claim 1, wherein the first cast product has an aspect ratio greater than 100:1.

32. The method of claim 1, further comprising surrounding the first cast product with a second casting material and demolding a second cast product formed from the second casting material, the second cast product having an aspect ratio greater than 100:1.

33. The method of claim 1, wherein a cavity defined by the stacked plurality of lithographically-derived micro-machined layers has an aspect ratio greater than 100:1.

34. The method of claim 1, wherein the first cast product is an end product.

35. The method of claim 1, further comprising surrounding the first cast product with a second casting material and demolding a second cast product formed from the second casting material, the second cast product being an end product.

36. The method of claim 1, wherein the first cast product is attached to a substrate.

37. The method of claim 1, wherein the first cast product is a free-standing structure.

38. A method of forming a casting, comprising:
filling a mold having a stacked plurality of lithographically-derived micro-machined metallic foil layers with a first casting material to form a first cast product having an aspect ratio of greater than 10:1, the stacked plurality of lithographically-derived micro-machined metallic foil layers defining a protruding undercut; and demolding the first cast product from the mold, the first cast product reflecting the protruding undercut, said first cast product comprising a plurality of product surfaces that define a periphery of a layer-less volume of said first cast product, a product surface from said plurality of product surfaces comprising a plurality of 3-dimensional micro-features that substantially spatially invertedly replicate a mold surface formed by said stacked plurality of metallic foil layers.

39. A method of fabricating a stack lamination mold, comprising:
lithographically micro-machining each of a plurality of metallic foil layers; and
assembling the plurality of layers into a stack that defines a protruding undercut and an aspect of greater than 10:1.

40. A lithographically-derived micro-machined metallic foil stack lamination mold that defines a protruding undercut and that defines an aspect ratio of greater than 10:1.

41. The lithographically-derived micro-machined metallic foil stack lamination mold of claim 40, wherein said mold is a positive replication of a predetermined end product.

42. The lithographically-derived micro-machined metallic foil stack lamination mold of claim 40, wherein said mold is a negative replication of a predetermined end product.

43. The lithographically-derived micro-machined metallic foil stack lamination mold of claim 40, wherein said mold defines at least one feature having an aspect ratio of greater than 10:1.

44. The lithographically-derived micro-machined metallic foil stack lamination mold of claim 40, wherein said mold defines at least one feature having an aspect ratio of greater than 15:1.

45. The lithographically-derived micro-machined metallic foil stack lamination mold of claim 40, wherein said mold defines at least one feature having an aspect ratio of greater than 20:1.

46. The lithographically-derived micro-machined metallic foil stack lamination mold of claim 40, wherein said mold defines at least one feature having an aspect ratio of greater than 25:1.

47. The lithographically-derived micro-machined metallic foil stack lamination mold of claim 40, wherein said mold defines at least one feature having an aspect ratio of greater than 30:1.

48. The lithographically-derived micro-machined metallic foil stack lamination mold of claim 40, wherein said mold defines at least one feature having an aspect ratio of greater than 40:1.

49. The lithographically-derived micro-machined metallic foil stack lamination mold of claim 40, wherein said mold defines at least one feature having an aspect ratio of greater than 50:1.

50. The lithographically-derived micro-machined metallic foil stack lamination mold of claim 40, wherein said mold defines at least one feature having an aspect ratio of greater than 75:1.

51. The lithographically-derived micro-machined metallic foil stack lamination mold of claim 40, wherein said mold defines at least one feature having an aspect ratio of greater than 100:1.

52. The lithographically-derived micro-machined metallic foil stack lamination mold of claim 40, wherein said mold defines at least one feature having an aspect ratio of greater than 150:1.

53. The lithographically-derived micro-machined metallic foil stack lamination mold of claim 40, wherein said mold defines at least one feature having an aspect ratio of greater than 200:1.

54. The lithographically-derived micro-machined metallic foil stack lamination mold of claim 40, wherein said mold defines at least one feature having an aspect ratio of greater than 250:1.

55. The lithographically-derived micro-machined metallic foil stack lamination mold of claim 40, wherein said mold defines at least one feature having an aspect ratio of greater than 300:1.

56. The lithographically-derived micro-machined metallic foil stack lamination mold of claim 40, wherein said mold defines at least one feature having an aspect ratio of greater than 400:1.

57. A metallic foil stack lamination mold that defines a protruding undercut and an aspect ratio of greater than 10:1.

58. A metallic foil stack lamination mold that defines a cavity having a protruding undercut and an aspect ratio of greater than 10:1.

59. A mold derived from a metallic foil stack lamination mold, said derived mold defining a cavity therein, a protruding undercut, and a feature having an aspect ratio greater than 10:1, said derived mold comprising a plurality of surfaces that define a periphery of a layer-less volume of said derived mold, a surface from said plurality of surfaces comprising a plurality of 3-dimensional micro-features that substantially spatially invertedly replicate a stack lamination mold surface formed by a stacked plurality of metallic foil layers comprised by said stack lamination mold.

60. A mold derived from a metallic foil stack lamination mold, said derived mold defining a protruding undercut and an aspect ratio of greater than 10:1, said derived mold comprising a plurality of surfaces that define a periphery of a layer-less volume of said derived mold, a surface from said plurality of surfaces comprising a plurality of 3-dimensional micro-features that substantially spatially invertedly replicate a stack lamination mold surface formed by a stacked plurality of metallic foil layers comprised by said stack lamination mold.

61. A mold derived from a metallic foil stack lamination mold, said derived mold defining a cavity having a protruding undercut and an aspect ratio of greater than 10:1, said derived mold comprising a plurality of surfaces that define a periphery of a layer-less volume of said derived mold, a surface from said plurality of surfaces comprising a plurality of 3-dimensional micro-features that substantially spatially invertedly replicate a stack lamination mold surface formed by a stacked plurality of metallic foil layers comprised by said stack lamination mold.

62. A method of forming a casting, comprising:
filling a mold having a stacked plurality of lithographically-derived micro-machined layers with a first casting material to form a first cast product having an aspect ratio of greater than 10:1, the stacked plurality of lithographically-derived micro-machined layers defining a protruding undercut; and
demolding the first cast product from the mold, such that the mold is not substantially damaged, said first cast product comprising a plurality of component surfaces that define a periphery of a layer-less volume of said first cast product, a component surface from said plurality of component surfaces comprising a plurality of 3-dimensional micro-features that substantially spatially invertedly replicate a mold surface formed by said stacked plurality of layers.

63. A method of forming a casting, comprising:
filling a mold having a stacked plurality of lithographically-derived micro-machined layers with a first casting material to form a first cast product having an aspect ratio of greater than 10:1, the stacked plurality of lithographically-derived micro-machined layers defining a protruding undercut; and demolding the first cast product from the mold such that the mold is not substantially damaged, the first cast product reflecting the protruding undercut, said first cast product comprising a plurality of component surfaces that define a periphery of a layer-less volume of said first cast product, a component surface from said plurality of component surfaces comprising a plurality of 3-dimensional micro-features that substantially spatially invertedly replicate a mold surface formed by said stacked plurality of layers.

* * * * *